(12) United States Patent
Hurth et al.

(10) Patent No.: US 9,284,284 B2
(45) Date of Patent: Mar. 15, 2016

(54) OXAZINE DERIVATIVES AND THEIR USE IN THE TREATMENT OF DISEASE

(71) Applicants: Konstanze Hurth, Lorrach (DE); Sebastien Jacquier, Hegenheim (FR); Rainer Machauer, Freiburg (DE); Heinrich Rueeger, Flueh (CH); Marina Tintelnot-Blomley, Maulburg (DE); Siem Jacob Veenstra, Lorrach (DE); Markus Voegtle, Lorrach (DE)

(72) Inventors: Konstanze Hurth, Lorrach (DE); Sebastien Jacquier, Hegenheim (FR); Rainer Machauer, Freiburg (DE); Heinrich Rueeger, Flueh (CH); Marina Tintelnot-Blomley, Maulburg (DE); Siem Jacob Veenstra, Lorrach (DE); Markus Voegtle, Lorrach (DE)

(73) Assignee: NOVARTIS AG, Basel (CH)

( * ) Notice: Subject to any disclaimer, the term of this patent is extended or adjusted under 35 U.S.C. 154(b) by 44 days.

(21) Appl. No.: 14/350,938

(22) PCT Filed: Oct. 11, 2012

(86) PCT No.: PCT/IB2012/055521
§ 371 (c)(1),
(2) Date: Apr. 10, 2014

(87) PCT Pub. No.: WO2013/054291
PCT Pub. Date: Apr. 18, 2013

(65) Prior Publication Data
US 2014/0256715 A1 Sep. 11, 2014

Related U.S. Application Data

(60) Provisional application No. 61/695,329, filed on Aug. 31, 2012, provisional application No. 61/546,836, filed on Oct. 13, 2011.

(51) Int. Cl.
| | | |
|---|---|---|
| *C07D 265/30* | (2006.01) |
| *C07D 413/04* | (2006.01) |
| *C07D 413/12* | (2006.01) |
| *C07D 413/14* | (2006.01) |
| *C07D 417/12* | (2006.01) |
| *C07D 471/04* | (2006.01) |
| *C07D 487/04* | (2006.01) |
| *A61K 31/5375* | (2006.01) |
| *A61K 31/5377* | (2006.01) |

(52) U.S. Cl.
CPC .......... *C07D 265/30* (2013.01); *A61K 31/5375* (2013.01); *A61K 31/5377* (2013.01); *C07D 413/04* (2013.01); *C07D 413/12* (2013.01); *C07D 413/14* (2013.01); *C07D 417/12* (2013.01); *C07D 471/04* (2013.01); *C07D 487/04* (2013.01)

(58) Field of Classification Search
CPC .......... A61K 31/5375; A61K 31/5377; C07D 265/30; C07D 413/04; C07D 413/12; C07D 413/14; C07D 417/12; C07D 471/04; C07D 487/04
See application file for complete search history.

(56) References Cited

U.S. PATENT DOCUMENTS

| | | |
|---|---|---|
| 2012/0184540 A1 | 7/2012 | Andreini et al. |
| 2012/0196863 A1 | 8/2012 | Andreini et al. |

FOREIGN PATENT DOCUMENTS

| | | |
|---|---|---|
| WO | 2011/009943 | 1/2011 |
| WO | 2011/020806 | 2/2011 |
| WO | 2011/138293 | 11/2011 |
| WO | 2011/154431 | 12/2011 |
| WO | 2012/095463 | 7/2012 |
| WO | 2012/095469 | 7/2012 |
| WO | 2012/095521 | 7/2012 |
| WO | 2012/098064 | 7/2012 |

*Primary Examiner* — Rebecca Anderson
(74) *Attorney, Agent, or Firm* — Joshua Roth

(57) ABSTRACT

The invention relates to novel oxazine derivatives of formula (I), and pharmaceutically acceptable salts thereof, in which all of the variables are as defined in the specification, pharmaceutical compositions thereof, combinations thereof, and their use as medicaments, particularly for the treatment of Alzheimer's Disease or diabetes via inhibition of BACE-1 or BACE-2.

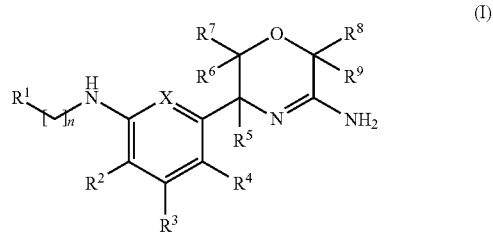

19 Claims, No Drawings

OXAZINE DERIVATIVES AND THEIR USE IN THE TREATMENT OF DISEASE

This application is a U.S. National Phase filing of International Application No. PCT/IB2012/055521 filed Oct. 11, 2012, which claims priority to U.S. Application Nos. 61/546,836 filed Oct. 13, 2011 and 61/695,329 filed Aug. 31, 2012.

BACKGROUND OF THE INVENTION

Alzheimer's Disease is a devastating neurodegenerative disorder. Its sporadic forms affect an elderly population (sharp increase in incidence at >75 years of age), in addition, there are various familial forms with an onset of the disease in the fourth or fifth decade of life. Pathologically, it is characterized by the presence of extracellular senile plaques, and intracellular neurofibrillar tangles in patient's brains. The core constituent of the senile plaques are small, 4 kDa amyloid peptides. They are generated by the proteolytic processing of a large transmembrane protein, amyloid precursor protein (APP). Cleavage of APP by beta-secretase (BACE-1) releases the soluble APP-beta fragment, while the 99-amino acid long C-terminus remains tethered to the membrane. This C-terminal fragment is subsequently proteolytically processed by gamma-secretase (an membrane multi-enzyme complex) to generate amyloid peptides of various length, predominantly 40 and 42 amino acids long (Hardy J, Selkoe D J (2002) Science; 297 (5580):353-356).

If, under pathologic conditions, the generation of these peptides occurs at an increased rate, or if their removal from the brain is disturbed, increased brain amyloid peptide concentrations leads to the formation of oligomers, fibrils and eventually plaques (Farris W, et al (2007) Am. J. Pathol.; 171 (1):241-251). It has been shown, that deposition of amyloid peptides and plaques in the brain is the first measurable event in the pathogenesis of Alzheimers Disease, and that it is the trigger for loss of synapses, synaptic contacts, and neurons (Grimmer T, et al (2009) Neurobiology of Aging; 30 (12): 1902-1909). Brain atrophy caused by massive neuron loss is followed by impairments in cognition, memory, orientation and the ability to perform the tasks of daily living, i.e. clinically manifest dementia (Okello A, et al (2009) Neurology; 73 (10):754-760).

BACE-1, also known as Asp2 or Memapsin 2, is a transmembrane aspartic protease highly expressed in neurons. It co-localizes with its substrate APP in Golgi and endocytic compartments (Willem M, Lammich S, Haass C (2009) Semin. Cell Dev. Biol; 20 (2):175-182). Knock-out studies in mice have demonstrated the absence of amyloid peptide formation, while the animals are healthy and fertile (Ohno M, et al (2007) Neurobiol. Dis.; 26 (1):134-145). Genetic ablation of BACE-1 in APP-overexpressing mice has demonstrated absence of plaque formation, and the reverse of cognitive deficits (Ohno M, et al (2004) Neuron; 41 (1):27-33). BACE-1 levels are elevated in the brains of sporadic Alzheimer's Disease patients (Hampel H, Shen Y (2009) Scand. J. Clin. Lab. Invest.; 69 (1):8-12).

Taken together, these findings suggest that the inhibition of BACE-1 may be a favourable therapeutic strategy for the treatment of Alzheimer's Disease.

Beta-site amyloid precursor protein cleaving enzyme 2 (BACE-2) is a transmembrane aspartic protease that is highly expressed in pancreatic β cells and other peripheral tissues (Bennett B, et al (2000) JJ. Biol. Chem. 275(27) 20647-20651). BACE-2 is closely related to BACE-1 or beta secretase. However, despite structural and sequence similarities the substrate specificity of BACE-1 and BACE-2 appear to be different. While Aβ or β-amyloid peptide is the main substrate of BACE-1, BACE-2 does not generate either form of Aβ (Vassar R, et al (1999) Science 286, 735-741).

Transmembrane protein 27 (TMEM27 or collectrin) plays an important role in β-cell proliferation and insulin secretion (Akpinar P, et al (2005) Tmem27: Cell Metabolism. 2(6) 385-397) and has been identified as a substrate for BACE-2 (WO 2010/063718). Tmem27 exists as a dimer and the extracellular domain is cleaved and shed from the plasma in a β cell-specific manner. Overexpression of full-length Tmem27, but not the truncated or soluble protein, increases β cell proliferation, suggesting that the full length protein is required for this biological function. Tcf1 (hepatocyte nuclear factor-1α, HNF-1α) controls the transcription of TMEM27. Mice with targeted deletion of Tcf1 exhibit decreased β cell mass, and knockdown of Tmem27 using RNAi results in a reduction of cell proliferation. Transgenic mice with increased expression of Tmem27 in pancreatic β cells exhibit increased β cell mass compared to their wild-type littermates. This data indicates that TMEM27 plays a role in control of β cell mass and that inhibition of BACE-2 which cleaves TMEM27 could be useful for treating loss of β cell mass and function, the underlying cause of diabetes.

Taken together, these findings suggest that the inhibition of BACE-2 may be a favourable therapeutic strategy for the treatment and prevention of metabolic disorders related to decreased β cell mass and/or function, such as type 2 diabetes.

FIELD OF THE INVENTION

The invention relates to novel oxazine derivatives and pharmaceutically acceptable salts thereof, pharmaceutical compositions thereof, pharmaceutical combinations thereof, and their use as medicaments, particularly for the treatment of neurodegeneration via inhibition of BACE-1 or diabetes via inhibition of BACE-2.

BRIEF SUMMARY OF THE INVENTION

The present invention relates to novel heterocyclic derivatives having BACE inhibitory activity, to their preparation, to their medical use and to medicaments comprising them.

More particularly, in a first aspect of the invention there is provided a compound of the formula (I), or a pharmaceutically acceptable salt thereof:

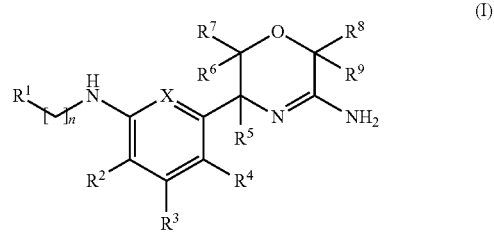

wherein
n represents 0 or 1;
X represents CH or N;
$R^1$ represents:
phenyl, optionally substituted by 1, 2 or 3 substituents independently selected from $R^{10}$;
a group $G_1$ selected from furan-2-yl, pyridin-2-yl, pyrimidin-2-yl, pyrimidin-4-yl and pyrazin-2-yl, wherein $G_1$ is optionally substituted by 1, 2 or 3 substituents independently selected from $R^{10}$; or a group $G_2$ selected from isothiazolo[4,5-b]pyridin-3-yl, isothiazolo[4,5-b]pyrazin-3-yl, benzo[d]isothiazol-3-yl, indazol-3-yl, benzo[d]isoxazol-3-yl, pyrido[3,2-d]pyrimidin-4-yl, [1,7]naphthyridin-8-yl and imidazol[1,2-a]pyrazin-8-yl, wherein $G_2$ is optionally substituted by 1, 2 or 3 substituents independently selected from $R^{11}$;

$R^2$, $R^3$ and $R^4$ independently represent hydrogen, halogen or $C_{1-3}$alkyl;

$R^5$ represents $C_{1-3}$alkyl, halogen-$C_{1-3}$alkyl or $C_{1-3}$alkoxy-$C_{1-3}$alkyl;

$R^6$ and $R^7$ independently represent hydrogen or $C_{1-3}$alkyl;

$R^8$ and $R^9$ independently represent hydrogen, $C_{1-3}$alkyl, halogen-$C_{1-3}$alkyl or $C_{1-3}$alkoxy; or $R^8$ and $R^9$ taken together are cyclopropyl;

$R^{10}$ represents halogen, cyano, hydroxy, halogen-$C_{1-3}$alkoxy, $C_{1-3}$alkoxy, $C_{1-3}$alkoxy-$C_{1-3}$alkoxy, nitro or amino; and $R^{11}$ represents halogen, cyano, hydroxy, $C_{1-3}$alkyl, halogen-$C_{1-3}$alkyl, halogen-$C_{1-3}$alkoxy, $C_{1-3}$ alkoxy, $C_{1-3}$alkoxy-$C_{1-3}$alkyl or $C_{1-3}$alkoxy-$C_{1-3}$alkoxy.

In a second aspect of the invention there is provided a compound of the formula (I), or a pharmaceutically acceptable salt thereof:

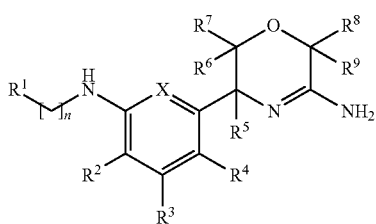

(I)

wherein n represents 0 or 1;

X represents CH or N;

$R^1$ represents:

phenyl, optionally substituted by 1, 2 or 3 substituents independently selected from $R^{10}$;

a group $G_1$ selected from furan-2-yl, pyridin-2-yl, pyrimidin-2-yl, pyrimidin-4-yl and pyrazin-2-yl, wherein $G_1$ is optionally substituted by 1, 2 or 3 substituents independently selected from $R^{10}$; or a group $G_2$ selected from isothiazolo[4,5-b]pyridin-3-yl, isothiazolo[4,5-b]pyrazin-3-yl, benzo[d]isothiazol-3-yl, indazol-3-yl, benzo[d]isoxazol-3-yl, pyrido[3,2-d]pyrimidin-4-yl, [1,7]naphthyridin-8-yl and imidazol[1,2-a]pyrazin-8-yl, wherein $G_2$ is optionally substituted by 1, 2 or 3 substituents independently selected from $R^{11}$;

$R^2$, $R^3$ and $R^4$ independently represent hydrogen, halogen or $C_{1-3}$alkyl;

$R^5$ represents $C_{1-3}$alkyl, halogen-$C_{1-3}$alkyl or $C_{1-3}$alkoxy-$C_{1-3}$alkyl;

$R^6$ and $R^7$ independently represent hydrogen or $C_{1-3}$alkyl;

$R^8$ and $R^9$ independently represent hydrogen, $C_{1-3}$alkyl, halogen-$C_{1-3}$alkyl or $C_{1-3}$alkoxy; or $R^8$ and $R^9$ taken together are cyclopropyl;

$R^{10}$ represents halogen, cyano, hydroxy, halogen-$C_{1-3}$ alkoxy, $C_{1-3}$alkoxy or $C_{1-3}$alkoxy-$C_{1-3}$alkoxy; and $R^{11}$ represents halogen, cyano, hydroxy, $C_{1-3}$alkyl, halogen-$C_{1-3}$alkyl, halogen-$C_{1-3}$alkoxy, $C_{1-3}$ alkoxy, $C_{1-3}$alkoxy-$C_{1-3}$alkyl or $C_{1-3}$alkoxy-$C_{1-3}$alkoxy.

DEFINITIONS

As used herein, the term "$C_{1-3}$alkyl" refers to a straight or branched hydrocarbon chain radical consisting solely of carbon and hydrogen atoms, containing no unsaturation, having from one to three carbon atoms, and which is attached to the rest of the molecule by a single bond. Examples of $C_{1-3}$alkyl include methyl, (R)-methyl, ethyl, n-propyl and 1-methylethyl(iso-propyl).

As used herein, the term "$C_{1-3}$alkoxy" refers to a radical of the formula —O—$R_a$ where $R_a$ is a $C_{1-3}$alkyl radical as generally defined above. Examples of $C_{1-3}$alkoxy include methoxy, ethoxy, propoxy and isopropoxy.

As used herein, the term "$C_{1-3}$alkoxy-$C_{1-3}$alkyl" refers to a radical of the formula —$R_a$—O—$R_a$ where each $R_a$ is independently a $C_{1-3}$alkyl radical as defined above. The oxygen atom may be bonded to any carbon atom in either alkyl radical. Examples of $C_{1-3}$alkoxy-$C_{1-3}$alkyl include methoxy-methyl, methoxy-ethyl, ethoxy-ethyl and 1-ethoxy-propyl.

As used herein, the term "$C_{1-3}$alkoxy-$C_{1-3}$alkoxy" refers to a radical of the formula —O—$R_a$—O—$R_a$ where each $R_a$ is independently a $C_{1-3}$alkyl radical as defined above. The oxygen atoms may be bonded to any alkyl radical carbon atom. Examples of $C_{1-3}$alkoxy-$C_{1-3}$alkoxy include methoxy-methoxy, methoxy-ethoxy, ethoxy-ethoxy and 1-ethoxy-propyloxy.

As used herein, the term "amino" refers to a radical of the formula —$NH_2$.

The term "halogen" refers to bromo, chloro, fluoro or iodo.

As used herein, the term "halogen-$C_{1-3}$alkyl" refers to a $C_{1-3}$alkyl radical, as defined above, substituted by one or more halo radicals, as defined above. Examples of halogen-$C_{1-3}$alkyl include trifluoromethyl, difluoromethyl, fluoromethyl, trichloromethyl, 2,2,2-trifluoroethyl, 1-fluoromethyl-2-fluoroethyl, 3-bromo-2-fluoropropyl and 1-bromomethyl-2-bromoethyl.

As used herein, the term "halogen-$C_{1-3}$alkoxy" refers to a $C_{1-3}$alkoxy radical, as defined above, substituted by one or more halo radicals, as defined above. Examples of halogen-$C_{1-3}$alkoxy include trifluoromethoxy, difluoromethoxy, fluoromethoxy, trichloromethoxy, 2,2,2-trifluoroethoxy, 1-fluoromethyl-2-fluoroethoxy, 3-bromo-2-fluoropropoxy and 1-bromomethyl-2-bromoethoxy.

As used herein, the term "a," "an," "the" and similar terms used in the context of the present invention (especially in the context of the claims) are to be construed to cover both the singular and plural unless otherwise indicated herein or clearly contradicted by the context. The use of any and all examples, or exemplary language (e.g. "such as") provided herein is intended merely to better illuminate the invention and does not pose a limitation on the scope of the invention otherwise claimed.

The term "compounds of the present invention" (unless specifically identified otherwise) refer to compounds of formula (I), (Ia), (Ib), (Ic) or (Id), compounds of the Examples, pharmaceutically acceptable salts of such compounds, and/or hydrates or solvates of such compounds, as well as, all stereoisomers (including diastereoisomers and enantiomers), tautomers and isotopically labeled compounds (including deuterium). The term "agents of the invention" is intended to have the same meaning as "compounds of the present invention".

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, unless the context dictates otherwise (for example in an embodiment of the invention clearly specifying a single enantiomer) the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

As used herein, the term "nitro" refers to a radical of the formula —$NO_2$.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

As used herein, the term "prevention" of any particular disease or disorder refers to the administration of a compound of the invention to a subject before any symptoms of that disease or disorder are apparent.

As used herein, the terms "salt" or "salts" refers to an acid addition salt of a compound of the invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, a subject is "in need of" a treatment if such subject would benefit biologically, medically or in quality of life from such treatment.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by BACE-1 or (ii) associated with BACE-1 activity, or (iii) characterized by activity (normal or abnormal) of BACE-1; or (2) reducing or inhibiting the activity of BACE-1. In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of BACE-1. The meaning of the term "a therapeutically effective amount" as illustrated in the above embodiments for BACE-1 also applies by the same means to any other relevant proteins/peptides/enzymes, such as BACE-2, or cathepsin D.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment, "treat", "treating" or "treatment" refers to modulating the disease or disorder, either physically, (e.g., stabilization of a discernible symptom), physiologically, (e.g., stabilization of a physical parameter), or both.

DETAILED DESCRIPTION OF THE INVENTION

The present invention provides compounds and pharmaceutical compositions thereof that may be useful in the treatment or prevention of diseases, conditions and/or disorders modulated by BACE inhibition.

Embodiment 1: a compound of formula (I), or a pharmaceutically acceptable salt thereof, as defined above in the first aspect of the invention.

Embodiment 2: a compound of formula (I), or a pharmaceutically acceptable salt thereof, as defined above in the second aspect of the invention.

Embodiment 3: a compound of formula (Ia), or a pharmaceutically acceptable salt thereof:

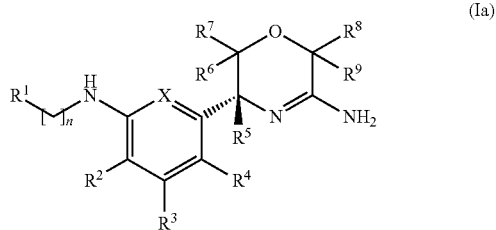

wherein
n represents 0 or 1;
X represents CH or N;
$R^1$ represents:
  phenyl, optionally substituted by 1, 2 or 3 substituents independently selected from $R^{10}$;
  a group $G_1$ selected from furan-2-yl, pyridin-2-yl, pyrimidin-2-yl, pyrimidin-4-yl and pyrazin-2-yl, wherein $G_1$ is optionally substituted by 1, 2 or 3 substituents independently selected from $R^{10}$;
  a group $G_2$ selected from isothiazolo[4,5-b]pyridin-3-yl, isothiazolo[4,5-b]pyrazin-3-yl, benzo[d]isothiazol-3-yl, indazol-3-yl, benzo[d]isoxazol-3-yl, pyrido[3,2-d]pyrimidin-4-yl, [1,7]naphthyridin-8-yl and imidazol[1,2-a]pyrazin-8-yl, wherein $G_2$ is optionally substituted by 1, 2 or 3 substituents independently selected from $R^{11}$;
$R^2$, $R^3$ and $R^4$ independently represent hydrogen, halogen or $C_{1-3}$alkyl;
$R^5$ represents $C_{1-3}$alkyl, halogen-$C_{1-3}$alkyl or $C_{1-3}$alkoxy-$C_{1-3}$alkyl;
$R^6$ and $R^7$ independently represent hydrogen or $C_{1-3}$alkyl;
$R^8$ and $R^9$ independently represent hydrogen, $C_{1-3}$alkyl, halogen-$C_{1-3}$alkyl or $C_{1-3}$alkoxy; or $R^8$ and $R^9$ taken together are cyclopropyl;
$R^{10}$ represents halogen, cyano, hydroxy, halogen-$C_{1-3}$alkoxy, $C_{1-3}$alkoxy or $C_{1-3}$alkoxy-$C_{1-3}$alkoxy; and
$R^{11}$ represents halogen, cyano, hydroxy, $C_{1-3}$alkyl, halogen-$C_{1-3}$alkyl, halogen-$C_{1-3}$alkoxy, $C_{1-3}$alkoxy, $C_{1-3}$alkoxy-$C_{1-3}$alkyl or $C_{1-3}$alkoxy-$C_{1-3}$alkoxy.

Embodiment 4: a compound according to any one of Embodiments 1 to 3, or a pharmaceutically acceptable salt thereof, wherein n represents 0.

Embodiment 5: a compound according to any one of Embodiments 1 to 3, or a pharmaceutically acceptable salt thereof, wherein n represents 1.

Embodiment 6: a compound according to any one of Embodiments 1 to 5, or a pharmaceutically acceptable salt thereof, wherein X represents CH.

Embodiment 7: a compound according to any one of Embodiments 1 to 5, or a pharmaceutically acceptable salt thereof, wherein X represents N.

Embodiment 8: a compound according to any one of Embodiments 1 to 7, or a pharmaceutically acceptable salt thereof, wherein $R^1$ represents phenyl optionally substituted by 1 or 2 substituents independently selected from $R^{10}$.

Embodiment 9: a compound according to any one of Embodiments 1 to 7, or a pharmaceutically acceptable salt thereof, wherein $R^1$ represents a group $G_1$ selected from furan-2-yl, pyridin-2-yl, pyrimidin-2-yl, pyrimidin-4-yl and pyrazin-2-yl, wherein $G_1$ is optionally substituted by 1, 2 or 3 substituents independently selected from $R^{10}$.

Embodiment 10: a compound according to any one of Embodiments 1 to 7, or a pharmaceutically acceptable salt thereof, wherein $R^1$ represents a group $G_1$ selected from pyridin-2-yl, pyrimidin-2-yl, pyrimidin-4-yl and pyrazin-2-yl, wherein $G_1$ is optionally substituted by 1 or 2 substituents independently selected from $R^{10}$.

Embodiment 11: a compound according to any one of Embodiments 1 to 7, or a pharmaceutically acceptable salt thereof, wherein $R^1$ represents a group $G_1$ selected from pyridin-2-yl, pyrimidin-4-yl and pyrazin-2-yl, wherein $G_1$ is substituted by a single substituent selected from $R^{10}$ positioned at the ortho carbon atom.

Embodiment 12: a compound according to anyone of Embodiments 9 to 11, or a pharmaceutically acceptable salt thereof, wherein $R^{10}$ represents methoxy, ethoxy, difluoromethoxy or difluoroethoxy.

Embodiment 13: a compound according to any one of Embodiments 1 to 7, or a pharmaceutically acceptable salt thereof, wherein $R^1$ represents a group $G_2$ selected from benzo[d]isothiazol-3-yl, indazol-3-yl, benzo[d]isoxazol-3-yl, pyrido[3,2-d]pyrimidin-4-yl, [1,7]naphthyridin-8-yl and imidazol[1,2-a]pyrazin-8-yl, wherein $G_2$ is optionally substituted by 1, 2 or 3 substituents independently selected from $R^{11}$.

Embodiment 14: a compound according to any one of Embodiments 1 to 7, or a pharmaceutically acceptable salt thereof, wherein $R^1$ represents a group $G_2$ selected from pyrido[3,2-d]pyrimidin-4-yl, [1,7]naphthyridin-8-yl and imidazol[1,2-a]pyrazin-8-yl, wherein $G_2$ is optionally substituted by 1 or 2 substituents independently selected from $R^{11}$.

Embodiment 15: a compound according to Embodiment 13 or Embodiment 14, or a pharmaceutically acceptable salt thereof, wherein $R^{11}$ represents halogen, cyano, methyl, ethyl, methoxy, ethoxy, 2-methoxy-ethoxy, 2-chloro-ethoxy, difluoromethyl or trifluoromethyl.

Embodiment 16: a compound according to any one of Embodiments 1 to 15, or a pharmaceutically acceptable salt thereof, wherein $R^2$ represents hydrogen.

Embodiment 17: a compound according to any one of Embodiments 1 to 16, or a pharmaceutically acceptable salt thereof, wherein $R^3$ represents hydrogen or halogen.

Embodiment 18: a compound according to any one of Embodiments 1 to 16, or a pharmaceutically acceptable salt thereof, wherein $R^3$ represents hydrogen or fluoro.

Embodiment 19: a compound according to any one of Embodiments 1 to 16, or a pharmaceutically acceptable salt thereof, wherein $R^3$ represents hydrogen.

Embodiment 20: a compound according to any one of Embodiments 1 to 19, or a pharmaceutically acceptable salt thereof, wherein $R^4$ represents hydrogen or halogen.

Embodiment 21: a compound according to any one of Embodiments 1 to 19, or a pharmaceutically acceptable salt thereof, wherein $R^4$ represents hydrogen or fluoro.

Embodiment 22: a compound according to any one of Embodiments 1 to 19, or a pharmaceutically acceptable salt thereof, wherein $R^4$ represents hydrogen.

Embodiment 23: a compound according to any one of Embodiments 1 to 19, or a pharmaceutically acceptable salt thereof, wherein $R^4$ represents fluoro.

Embodiment 24: a compound according to any one of Embodiments 1 to 23, or a pharmaceutically acceptable salt thereof, wherein $R^5$ represents methyl, fluoromethyl, difluoromethyl, methoxymethyl, methoxyethyl, ethoxymethyl or ethoxyethyl.

Embodiment 25: a compound according to any one of Embodiments 1 to 23, or a pharmaceutically acceptable salt thereof, wherein $R^5$ represents methyl, fluoromethyl or difluoromethyl.

Embodiment 26: a compound according to any one of Embodiments 1 to 25, or a pharmaceutically acceptable salt thereof, wherein $R^6$ and $R^7$ independently represent hydrogen, or methyl.

Embodiment 27: a compound according to any one of Embodiments 1 to 25, or a pharmaceutically acceptable salt thereof, wherein $R^6$ and $R^7$ both represent hydrogen.

Embodiment 28: a compound according to any one of Embodiments 1 to 27, or a pharmaceutically acceptable salt thereof, wherein $R^8$ and $R^9$ independently represent hydrogen, methyl, fluoromethyl, difluoromethyl or trifluoromethyl.

Embodiment 29: a compound according to any one of Embodiments 1 to 27, or a pharmaceutically acceptable salt thereof, wherein $R^8$ represents methyl and $R^9$ represents trifluoromethyl.

Embodiment 30: a compound according to any one of Embodiments 1 to 27, or a pharmaceutically acceptable salt thereof, wherein $R^8$ and $R^9$ both represent hydrogen.

Embodiment 31: a compound according to Embodiment 1 which is selected from:

[3-(5-Amino-3-methyl-3,6-dihydro-2H-[1,4]oxazin-3-yl)-phenyl]-(6-bromo-benzo[d]isothiazol-3-yl)-amine;
[3-(5-Amino-3-methyl-3,6-dihydro-2H-[1,4]oxazin-3-yl)-phenyl]-(6-bromo-1-methyl-1H-indazol-3-yl)-amine;
[3-(5-Amino-3-methyl-3,6-dihydro-2H-[1,4]oxazin-3-yl)-phenyl]-benzo[d]isoxazol-3-yl-amine;
5-{2-Fluoro-5-[(furan-2-ylmethyl)-amino]-phenyl}-5-methyl-5,6-dihydro-2H-[1,4]oxazin-3-ylamine;
5-[5-(4-Bromo-2-chloro-benzylamino)-2-fluoro-phenyl]-5-fluoromethyl-5,6-dihydro-2H-[1,4]oxazin-3-ylamine;
5-{5-[(4-Bromo-furan-2-ylmethyl)-amino]-2-fluoro-phenyl}-5-difluoromethyl-5,6-dihydro-2H-[1,4]oxazin-3-ylamine;
3-(5-Amino-3-difluoromethyl-3,6-dihydro-2H-[1,4]oxazin-3-yl)-4-fluoro-phenyl]-(7-chloropyrido[3,2-d]pyrimidin-4-yl)-amine;
[3-(5-Amino-3-difluoromethyl-3,6-dihydro-2H-[1,4]oxazin-3-yl)-4-fluoro-phenyl]-(3-bromo-[1,7]naphthyridin-8-yl)-amine;
8-[3-(5-Amino-3-difluoromethyl-3,6-dihydro-2H-[1,4]oxazin-3-yl)-4-fluoro-phenylamino]-[1,7]naphthyridine-3-carbonitrile;
[3-(5-Amino-3-difluoromethyl-3,6-dihydro-2H-[1,4]oxazin-3-yl)-4-fluoro-phenyl]-[3-(2-methoxy-ethoxy)-[1,7]naphthyridin-8-yl]-amine;
[3-(5-Amino-3-difluoromethyl-3,6-dihydro-2H-[1,4]oxazin-3-yl)-4-fluoro-phenyl]-[3-(2-chloro-ethoxy)-[1,7]naphthyridin-8-yl]-amine;
[3-(5-Amino-3-difluoromethyl-3,6-dihydro-2H-[1,4]oxazin-3-yl)-4-fluoro-phenyl]-(2-methyl-imidazo[1,2-a]pyrazin-8-yl)-amine;
[3-(5-Amino-3-difluoromethyl-3,6-dihydro-2H-[1,4]oxazin-3-yl)-4-fluoro-phenyl]-imidazo[1,2-a]pyrazin-8-yl-amine;
[3-(5-Amino-3-difluoromethyl-3,6-dihydro-2H-[1,4]oxazin-3-yl)-4-fluoro-phenyl]-(3-bromo-imidazo[1,2-a]pyrazin-8-yl)-amine;
5-Difluoromethyl-5-[2-fluoro-5-(3-methoxy-pyridin-2-ylamino)-phenyl]-5,6-dihydro-2H-[1,4]oxazin-3-ylamine;
5-Difluoromethyl-5-[2-fluoro-5-(pyrimidin-2-ylamino)-phenyl]-5,6-dihydro-2H-[1,4]oxazin-3-ylamine;
5-Difluoromethyl-5-[2-fluoro-5-(4-methoxy-pyrimidin-2-ylamino)-phenyl]-5,6-dihydro-2H-[1,4]oxazin-3-ylamine;
5-Difluoromethyl-5-[2-fluoro-5-(3-methoxy-pyrazin-2-ylamino)-phenyl]-5,6-dihydro-2H-[1,4]oxazin-3-ylamine;
5-Difluoromethyl-5-[5-(3-ethoxy-pyridin-2-ylamino)-2-fluoro-phenyl]-5,6-dihydro-2H-[1,4]oxazin-3-ylamine;
5-{5-[3-(2,2-Difluoro-ethoxy)-pyridin-2-ylamino]-2-fluoro-phenyl}-5-difluoromethyl-5,6-dihydro-2H-[1,4]oxazin-3-ylamine;
5-Difluoromethyl-5-[2-fluoro-5-(5-methoxy-pyrimidin-4-ylamino)-phenyl]-5,6-dihydro-2H-[1,4]oxazin-3-ylamine;
5-[5-(3-Difluoromethoxy-pyridin-2-ylamino)-2-fluoro-phenyl]-5-difluoromethyl-5,6-dihydro-2H-[1,4]oxazin-3-ylamine;
[3-(5-Amino-3,6-dimethyl-6-trifluoromethyl-3,6-dihydro-2H-[1,4]oxazin-3-yl)-4-fluoro-phenyl]-(7-chloro-pyrido[3,2-d]pyrimidin-4-yl)-amine;
[3-(5-Amino-3,6-dimethyl-6-trifluoromethyl-3,6-dihydro-2H-[1,4]oxazin-3-yl)-4-fluoro-phenyl]-(7-trifluoromethyl-pyrido[3,2-d]pyrimidin-4-yl)-amine;
5-[2-Fluoro-5-(3-methoxy-pyridin-2-ylamino)-phenyl]-2,5-di methyl-2-trifluoromethyl-5,6-dihydro-2H-[1,4]oxazin-3-ylamine;
5-Difluoromethyl-5-[2-fluoro-5-(3-methoxy-5-nitro-pyridin-2-ylamino)-phenyl]-5,6-dihydro-2H-[1,4]oxazin-3-ylamine;
N*2*-[3-(5-Amino-3-difluoromethyl-3,6-dihydro-2H-[1,4]oxazin-3-yl)-4-fluoro-phenyl]-3-methoxy-pyridine-2,5-diamine;
[6-(5-Amino-3,6-dimethyl-6-trifluoromethyl-3,6-dihydro-2H-[1,4]oxazin-3-yl)-5-fluoro-pyridin-2-yl]-(7-trifluoromethyl-pyrido[3,2-d]pyrimidin-4-yl)-amine;
5-[3-Fluoro-6-(2-methoxy-phenylamino)-pyridin-2-yl]-2,5-dimethyl-2-trifluoromethyl-5,6-dihydro-2H-[1,4]oxazin-3-ylamine;
2-[6-(5-Amino-3,6-dimethyl-6-trifluoromethyl-3,6-dihydro-2H-[1,4]oxazin-3-yl)-5-fluoro-pyridin-2-ylamino]-nicotinonitrile;
5-[3-Fluoro-6-(3-methoxy-pyridin-2-ylamino)-pyridin-2-yl]-2,5-dimethyl-2-trifluoromethyl-5,6-dihydro-2H-[1,4]oxazin-3-ylamine;
[3-(5-Amino-3-methyl-3,6-dihydro-2H-[1,4]oxazin-3-yl)-phenyl]-(1-methyl-1H-indazol-3-yl)-amine; and pharmaceutically acceptable salts thereof.

Embodiment 32: a compound according to Embodiment 1 which is selected from:

[3-(5-Amino-3-methyl-3,6-dihydro-2H-[1,4]oxazin-3-yl)-phenyl]-(6-bromo-benzo[d]isothiazol-3-yl)-amine;
[3-(5-Amino-3-methyl-3,6-dihydro-2H-[1,4]oxazin-3-yl)-phenyl]-(6-bromo-1-methyl-1H-indazol-3-yl)-amine;
[3-(5-Amino-3-methyl-3,6-dihydro-2H-[1,4]oxazin-3-yl)-phenyl]-benzo[d]isoxazol-3-yl-amine;
5-{2-Fluoro-5-[(furan-2-ylmethyl)-amino]-phenyl}-5-methyl-5,6-dihydro-2H-[1,4]oxazin-3-ylamine;
5-[5-(4-Bromo-2-chloro-benzylamino)-2-fluoro-phenyl]-5-fluoromethyl-5,6-dihydro-2H-[1,4]oxazin-3-ylamine;
5-{5-[(4-Bromo-furan-2-ylmethyl)-amino]-2-fluoro-phenyl}-5-difluoromethyl-5,6-dihydro-2H-[1,4]oxazin-3-ylamine;
3-((R)-5-Amino-3-difluoromethyl-3,6-dihydro-2H-[1,4]oxazin-3-yl)-4-fluoro-phenyl]-(7-chloropyrido[3,2-d]pyrimidin-4-yl)-amine;
[3-((R)-5-Amino-3-difluoromethyl-3,6-dihydro-2H-[1,4]oxazin-3-yl)-4-fluoro-phenyl]-(3-bromo-[1,7]naphthyridin-8-yl)-amine;
8-[3-((R)-5-Amino-3-difluoromethyl-3,6-dihydro-2H-[1,4]oxazin-3-yl)-4-fluoro-phenylamino]-[1,7]naphthyridine-3-carbonitrile;
[3-((R)-5-Amino-3-difluoromethyl-3,6-dihydro-2H-[1,4]oxazin-3-yl)-4-fluoro-phenyl]-[3-(2-methoxy-ethoxy)-[1,7]naphthyridin-8-yl]-amine;
[3-((R)-5-Amino-3-difluoromethyl-3,6-dihydro-2H-[1,4]oxazin-3-yl)-4-fluoro-phenyl]-[3-(2-chloro-ethoxy)-[1,7]naphthyridin-8-yl]-amine;
[3-((R)-5-Amino-3-difluoromethyl-3,6-dihydro-2H-[1,4]oxazin-3-yl)-4-fluoro-phenyl]-(2-methyl-imidazo[1,2-a]pyrazin-8-yl)-amine;

[3-((R)—S-Amino-3-difluoromethyl-3,6-dihydro-2H-[1,4]
oxazin-3-yl)-4-fluoro-phenyl]-imidazo[1,2-a]pyrazin-8-
yl-amine;

[3-((R)-5-Amino-3-difluoromethyl-3,6-dihydro-2H-[1,4]
oxazin-3-yl)-4-fluoro-phenyl]-(3-bromo-imidazo[1,2-a]
pyrazin-8-yl)-amine;

(R)-5-Difluoromethyl-5-[2-fluoro-5-(3-methoxy-pyridin-2-
ylamino)-phenyl]-5,6-dihydro-2H-[1,4]oxazin-3-
ylamine;

(R)-5-Difluoromethyl-5-[2-fluoro-5-(pyrimidin-2-
ylamino)-phenyl]-5,6-dihydro-2H-[1,4]oxazin-3-
ylamine;

(R)-5-Difluoromethyl-5-[2-fluoro-5-(4-methoxy-pyrimidin-
2-ylamino)-phenyl]-5,6-dihydro-2H-[1,4]oxazin-3-
ylamine;

(R)-5-Difluoromethyl-5-[2-fluoro-5-(3-methoxy-pyrazin-2-
ylamino)-phenyl]-5,6-dihydro-2H-[1,4]oxazin-3-
ylamine;

(R)-5-Difluoromethyl-5-[5-(3-ethoxy-pyridin-2-ylamino)-
2-fluoro-phenyl]-5,6-dihydro-2H-[1,4]oxazin-3-ylamine;

(R)-5-{5-[3-(2,2-Difluoro-ethoxy)-pyridin-2-ylamino]-2-
fluoro-phenyl}-5-difluoromethyl-5,6-dihydro-2H-[1,4]
oxazin-3-ylamine;

(R)-5-Difluoromethyl-5-[2-fluoro-5-(5-methoxy-pyrimidin-
4-ylamino)-phenyl]-5,6-dihydro-2H-[1,4]oxazin-3-
ylamine;

(R)-5-[5-(3-Difluoromethoxy-pyridin-2-ylamino)-2-fluoro-
phenyl]-5-difluoromethyl-5,6-dihydro-2H-[1,4]oxazin-3-
ylamine;

[3-((3R,6R)-5-Amino-3,6-dimethyl-6-trifluoromethyl-3,6-
dihydro-2H-[1,4]oxazin-3-yl)-4-fluoro-phenyl]-(7-
chloro-pyrido[3,2-d]pyrimidin-4-yl)-amine;

[3-((3R,6R)-5-Amino-3,6-dimethyl-6-trifluoromethyl-3,6-
dihydro-2H-[1,4]oxazin-3-yl)-4-fluoro-phenyl]-(7-trif-
luoromethyl-pyrido[3,2-d]pyrimidin-4-yl)-amine;

(2R,5R)-5-[2-Fluoro-5-(3-methoxy-pyridin-2-ylamino)-
phenyl]-2,5-dimethyl-2-trifluoromethyl-5,6-dihydro-2H-
[1,4]oxazin-3-ylamine;

(R)-5-Difluoromethyl-5-[2-fluoro-5-(3-methoxy-5-nitro-
pyridin-2-ylamino)-phenyl]-5,6-dihydro-2H-[1,4]oxazin-
3-ylamine;

N*2*-[3-((R)-5-Amino-3-difluoromethyl-3,6-dihydro-2H-
[1,4]oxazin-3-yl)-4-fluoro-phenyl]-3-methoxy-pyridine-
2,5-diamine;

[6-((3R,6R)-5-Amino-3,6-dimethyl-6-trifluoromethyl-3,6-
dihydro-2H-[1,4]oxazin-3-yl)-5-fluoro-pyridin-2-yl]-(7-
trifluoromethyl-pyrido[3,2-d]pyrimidin-4-yl)-amine;

(2R,5R)-5-[3-Fluoro-6-(2-methoxy-phenylamino)-pyridin-
2-yl]-2,5-dimethyl-2-trifluoromethyl-5,6-dihydro-2H-[1,
4]oxazin-3-ylamine;

2-[6-((3R,6R)-5-Amino-3,6-dimethyl-6-trifluoromethyl-3,
6-dihydro-2H-[1,4]oxazin-3-yl)-5-fluoro-pyridin-2-
ylamino]-nicotinonitrile;

(2R,5R)-5-[3-Fluoro-6-(3-methoxy-pyridin-2-ylamino)-py-
ridin-2-yl]-2,5-dimethyl-2-trifluoromethyl-5,6-dihydro-
2H-[1,4]oxazin-3-ylamine;

[3-((R)-5-Amino-3-methyl-3,6-dihydro-2H-[1,4]oxazin-3-
yl)-phenyl]-(1-methyl-1H-indazol-3-yl)-amine; and pharmaceutically acceptable salts thereof.

In another embodiment, there is provided a compound of the formula (Ib), or a pharmaceutically acceptable salt thereof:

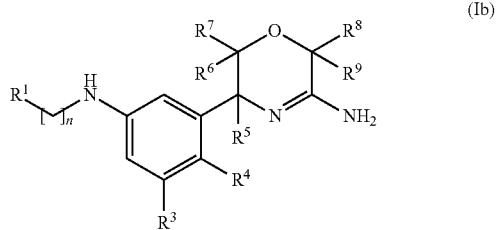

wherein n represents 0 or 1;

R$^1$ represents:

phenyl optionally substituted by 1 or 2 substituents independently selected from R$^{10}$;

a group G$_1$ selected from furan-2-yl, pyridin-2-yl, pyrimidin-2-yl, pyrimidin-4-yl and pyrazin-2-yl, wherein G$_1$ is optionally substituted by 1, 2 or 3 substituents independently selected from R$^{10}$;

a group G$_2$ selected from benzo[d]isothiazol-3-yl, indazol-3-yl, benzo[d]isoxazol-3-yl, pyrido[3,2-d]pyrimidin-4-yl, [1,7]naphthyridin-8-yl and imidazol[1,2-a]pyrazin-8-yl, wherein G$_2$ is optionally substituted by 1, 2 or 3 substituents independently selected from R$^{11}$;

R$^3$ and R$^4$ independently represent hydrogen or fluoro;

R$^5$ represents methyl, fluoromethyl, difluoromethyl, methoxymethyl, methoxyethyl, ethoxymethyl or ethoxyethyl;

R$^6$ and R$^7$ independently represent hydrogen or methyl;

R$^8$ and R$^9$ independently represent hydrogen, methyl, fluoromethyl, difluoromethyl or trifluoromethyl;

R$^{10}$ represents halogen, cyano, hydroxy, halogen-C$_{1-3}$alkoxy, C$_{1-3}$alkoxy or C$_{1-3}$alkoxy-C$_{1-3}$alkoxy; and R$^{11}$ represents halogen, cyano, hydroxy, C$_{1-3}$alkyl, halogen-C$_{1-3}$alkyl, halogen-C$_{1-3}$alkoxy, C$_{1-3}$alkoxy, C$_{1-3}$alkoxy-C$_{1-3}$alkyl or C$_{1-3}$alkoxy-C$_{1-3}$alkoxy.

In a further embodiment, there is provided a compound of the formula (Ic), or a pharmaceutically acceptable salt thereof:

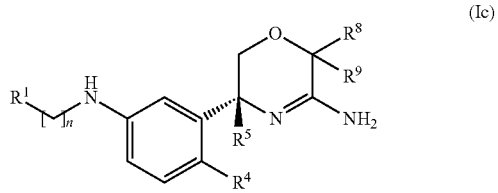

wherein n represents 0 or 1;

R$^1$ represents:

a group G$_1$ selected from pyridin-2-yl, pyrimidin-2-yl, pyrimidin-4-yl and pyrazin-2-yl, wherein G$_1$ is optionally substituted by 1 or 2 substituents independently selected from R$^{10}$;

a group G$_2$ selected from pyrido[3,2-d]pyrimidin-4-yl, [1,7]naphthyridin-8-yl and imidazol[1,2-a]pyrazin-8-yl, wherein G$_2$ is optionally substituted by 1 or 2 substituents independently selected from R$^{11}$;

R$^4$ represents hydrogen or fluoro;

R$^5$ represents methyl, fluoromethyl or difluoromethyl;

R$^8$ and R$^9$ independently represent hydrogen, methyl, fluoromethyl, difluoromethyl or trifluoromethyl;

$R^{10}$ represents halogen, cyano, hydroxy, halogen-$C_{1-3}$ alkoxy, $C_{1-3}$alkoxy or $C_{1-3}$alkoxy-$C_{1-3}$alkoxy; and $R^{11}$ represents halogen, cyano, hydroxy, $C_{1-3}$alkyl, halogen-$C_{1-3}$alkyl, halogen-$C_{1-3}$alkoxy, $C_{1-3}$alkoxy, $C_{1-3}$alkoxy-$C_{1-3}$alkyl or $C_{1-3}$alkoxy-$C_{1-3}$alkoxy.

In a further embodiment, there is provided a compound of the formula (Id), or a pharmaceutically acceptable salt thereof:

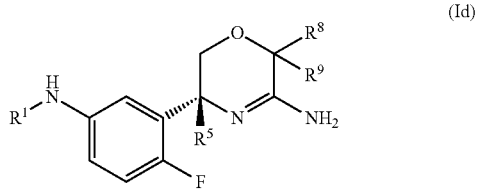

(Id)

wherein
$R^1$ represents:
a group $G_2$ selected from pyrido[3,2-d]pyrimidin-4-yl, [1,7]naphthyridin-8-yl and imidazol[1,2-a]pyrazin-8-yl, wherein $G_2$ is optionally substituted by 1 or 2 substituents independently selected from $R^{11}$;

$R^5$ represents methyl, fluoromethyl or difluoromethyl;

$R^8$ and $R^9$ independently represent hydrogen, methyl, fluoromethyl, difluoromethyl or trifluoromethyl; and $R^{11}$ represents halogen, cyano, methyl, ethyl, methoxy, ethoxy, 2-methoxy-ethoxy, 2-chloro-ethoxy, difluoromethyl or trifluoromethyl.

In one embodiment, there is provided a compound of the invention of formula (I), (Ia), (Ib), (Ic) or (Id) as defined herein, or a pharmaceutically acceptable salt thereof, wherein the compound is other than:

5-[3-(3-Chloro-benzylamino)-phenyl]-5-methyl-5,6-dihydro-2H-[1,4]oxazin-3-ylamine;
5-[3-(4-Chloro-benzylamino)-phenyl]-5-methyl-5,6-dihydro-2H-[1,4]oxazin-3-ylamine;
5-[3-(2,4-Dichloro-benzylamino)-phenyl]-5-methyl-5,6-dihydro-2H-[1,4]oxazin-3-ylamine;
(S)-5-(5-(6-chloro-1-methyl-1H-indazol-3-ylamino)-2-fluorophenyl)-5-methyl-5,6-dihydro-2H-1,4-oxazin-3-amine;
(R)-5-{5-[2-(2,2-Difluoro-ethoxy)-phenylamino]-2-fluorophenyl}-5-methyl-5,6-dihydro-2H-[1,4]oxazin-3-ylamine;
(R)-5-{5-[2-(2,2-Difluoro-ethoxy)-phenylamino]-2-fluorophenyl}-5-methyl-5,6-dihydro-2H-[1,4]oxazin-3-ylamine hydrochloride;
(R)-5-{2-Fluoro-5-[2-(2,2,2-trifluoro-ethoxy)-phenylamino]-phenyl}-5-methyl-5,6-dihydro-2H-[1,4]oxazin-3-ylamine;
(R)-5-{2-Fluoro-5-[2-(2,2,2-trifluoro-ethoxy)-phenylamino]-phenyl}-5-methyl-5,6-dihydro-2H-[1,4]oxazin-3-ylamine hydrochloride;
(R)-5-{2-Fluoro-5-[2-(2-fluoro-ethoxy)-phenylamino]-phenyl}-5-methyl-5,6-dihydro-2H-[1,4]oxazin-3-ylamine;
(R)-5-{2-Fluoro-5-[2-(2-fluoro-ethoxy)-phenylamino]-phenyl}-5-methyl-5,6-dihydro-2H-[1,4]oxazin-3-ylamine hydrochloride;
5-[3-(2-Difluoromethoxy-phenylamino)-phenyl]-5-methyl-5,6-dihydro-2H-[1,4]oxazin-3-ylamine; or
5-[3-(2-Difluoromethoxy-phenylamino)-phenyl]-5-methyl-5,6-dihydro-2H-[1,4]oxazin-3-ylamine hydrochloride.

On account of one or more than one asymmetrical carbon atom, which may be present in a compound of the formula (I), a corresponding compound of the formula (I) may exist in pure optically active form or in the form of a mixture of optical isomers, e. g. in the form of a racemic mixture. All of such pure optical isomers and all of their mixtures, including the racemic mixtures, are part of the present invention unless the context dictates otherwise (for example in an embodiment of the invention clearly specifying a single enantiomer).

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. Where a compound comprising one or more chiral centers is drawn herein with the stereochemistry indicated in the drawn structure, then the individual optical isomer is intended. Where a compound comprising one or more chiral centers is drawn herein without the stereochemistry indicated in the drawn structure, then no one specific optical isomer is intended and the drawn chemical structure may represent any optical isomer or mixture of isomers having that structure, for example a racemic or diasteriomeric mixture.

In one embodiment, there is provided a compound of the Examples as an isolated stereoisomer wherein the compound has one stereocenter and the stereoisomer is in the R configuration.

In one embodiment, there is provided a compound of the Examples as an isolated stereoisomer wherein the compound has one stereocenter and the stereoisomer is in the S configuration.

In one embodiment, there is provided a compound of the Examples as an isolated stereoisomer wherein the compound has two stereocenters and the stereoisomer is in the R R configuration.

In one embodiment, there is provided a compound of the Examples as an isolated stereoisomer wherein the compound has two stereocenters and the stereoisomer is in the R S configuration.

In one embodiment, there is provided a compound of the Examples as an isolated stereoisomer wherein the compound has two stereocenters and the stereoisomer is in the S R configuration.

In one embodiment, there is provided a compound of the Examples as an isolated stereoisomer wherein the compound has two stereocenters and the stereoisomer is in the S S configuration.

In one embodiment, there is provided a compound of the Examples, wherein the compound has one or two stereocenters, as a racemic mixture.

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons.

The compounds of the present invention may be capable of forming acid salts by virtue of the presence of amino groups or groups similar thereto.

In one embodiment, the invention relates to a compound of the formula (I), (Ia), (Ib), (Ic) or (Id) as defined herein, in free form. In another embodiment, the invention relates to a compound of the formula (I), (Ia), (Ib), (Ic) or (Id) as defined herein, in salt form. In another embodiment, the invention relates to a compound of the formula (I), (Ia), (Ib), (Ic) or (Id) as defined herein, in acid addition salt form. In a further embodiment, the invention relates to a compound of the formula (I), (Ia), (Ib), (Ic) or (Id) as defined herein, in pharmaceutically acceptable salt form. In yet a further embodiment, the invention relates to a compound of the formula (I), (Ia), (Ib), (Ic) or (Id) as defined herein, in pharmaceutically acceptable acid addition salt form. In yet a further embodiment, the invention relates to a compound of the formula (I), (Ia), (Ib), (Ic) or (Id) as defined herein, in hydrochloride salt form. In yet a further embodiment, the invention relates to any one of the compounds of the Examples in free form. In yet a further embodiment, the invention relates to any one of the compounds of the Examples in salt form. In yet a further embodiment, the invention relates to any one of the compounds of the Examples in acid addition salt form. In yet a further embodiment, the invention relates to any one of the compounds of the Examples in pharmaceutically acceptable salt form. In still another embodiment, the invention relates to any one of the compounds of the Examples in pharmaceutically acceptable acid addition salt form. In still another embodiment, the invention relates to any one of the compounds of the Examples in hydrochloride salt form.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts may be derived include, for example, hydrochloric acid, hydrobromic acid, sulfuric acid, nitric acid, phosphoric acid, and the like.

Organic acids from which salts may be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

The pharmaceutically acceptable salts of the present invention can be synthesized from an acidic moiety, by conventional chemical methods. Generally, such salts can be prepared by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Furthermore, the compounds of the present invention, including their salts, may also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

The compounds of the present invention, including salts, hydrates and solvates thereof, may inherently or by design form polymorphs.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the present invention may be synthesized by synthetic routes that include processes analogous to those well-known in the chemical arts, particularly in light of the description contained herein. The starting materials are generally available from commercial sources such as Sigma-Aldrich or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), or Beilsteins Handbuch der organischen Chemie, 4, Aufl. ed. Springer-Verlag, Berlin, including supplements (also available via the Beilstein online database)).

For illustrative purposes, the reaction scheme 1 depicted below provides potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

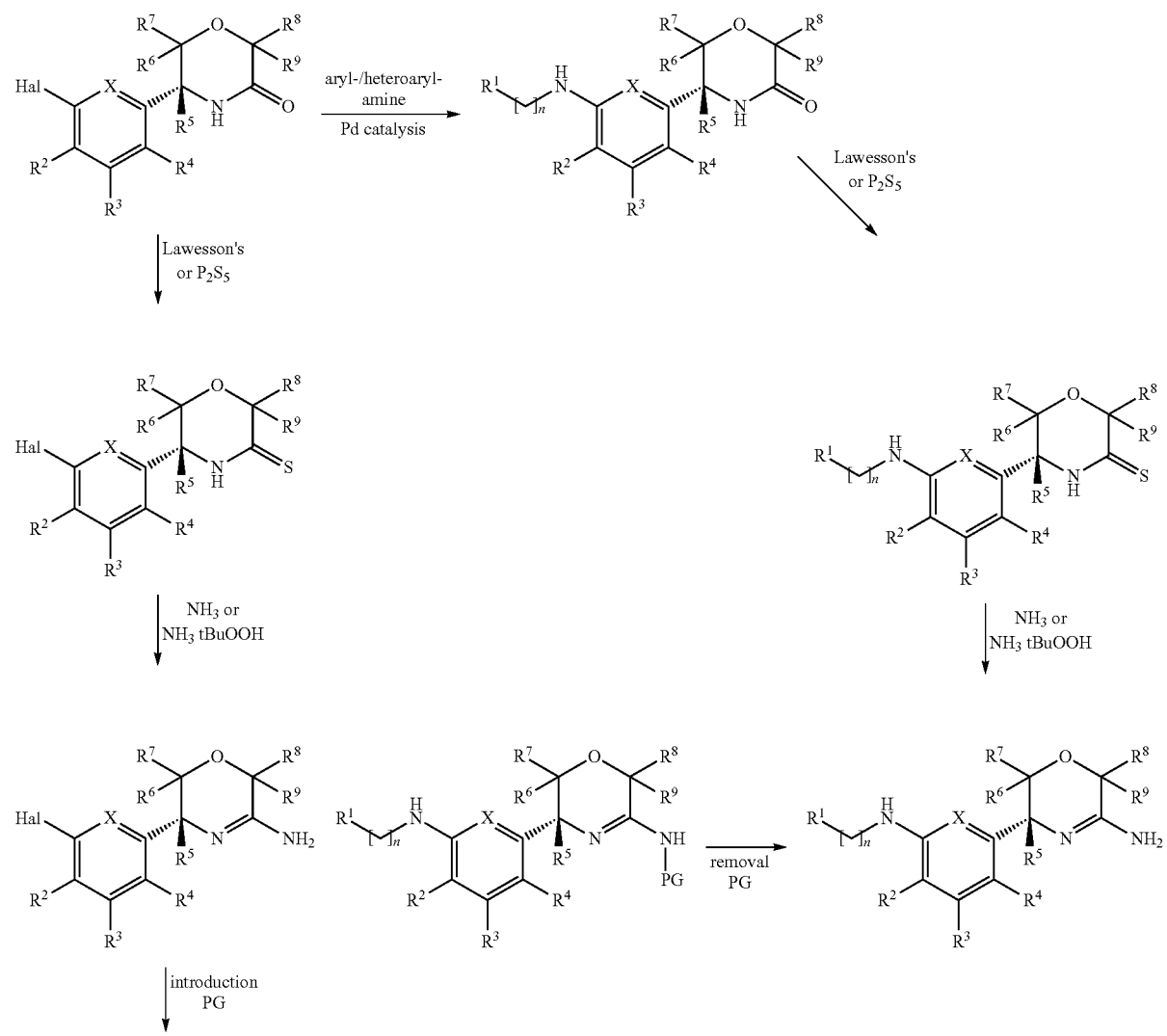

Scheme 1

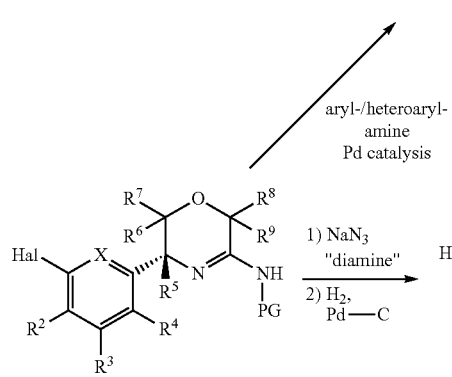
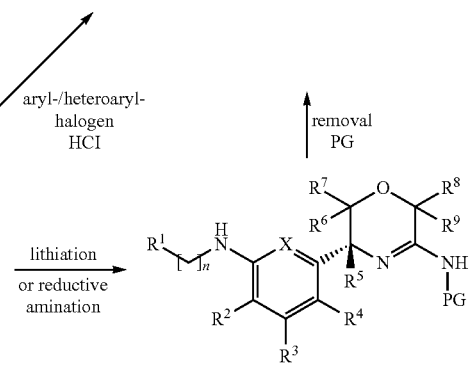

In a further aspect, the invention relates to a process for the preparation of a compound of the formula (I), in free form or in pharmaceutically acceptable salt form, comprising a) where n is 0, the reaction of a compound of the formula

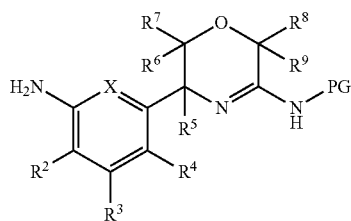
(II)

in free form or in salt form, in which X, $R^2$, $R^3$, $R^4$, $R^5$, $R^6$, $R^7$, $R^8$ and $R^9$ are as defined for the formula I and PG is a protecting group, for example N-tert-butoxycarbonyl, with a compound of the formula

(III)

in free form or in salt form, in which $R^1$ is as defined for the formula I and Hal is halogen, for example chloro, b) where n is 1, the reaction of a compound of the formula

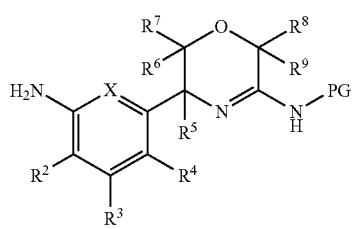
(II)

in free form or in salt form, in which X, $R^2$, $R^3$, $R^4$, $R^5$, $R^6$, $R^7$, $R^8$ and $R^9$ are as defined for the formula I and PG is a protecting group, for example N-tert-butoxycarbonyl, with a compound of the formula $$\underset{O}{\overset{R^1}{\diagdown}}\hspace{-1.5em}\diagup\hspace{-0.5em}H \quad (IV)$$

in free form or in salt form, in which $R^1$ is as defined for the formula I, c) the reaction of a compound of the formula

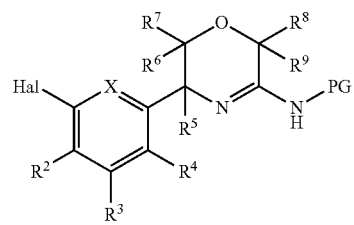
(V)

in free form or in salt form, in which X, $R^2$, $R^3$, $R^4$, $R^5$, $R^6$, $R^7$, $R^8$ and $R^9$ are as defined for the formula I, Hal is halogen, for example bromine, and PG is a protecting group, for example N-tert-butoxycarbonyl, with a compound of the formula $$R^1 \diagdown \hspace{-0.5em} NH_2 \quad (VI)$$

in free form or in salt form, in which $R^1$ and n are as defined for the formula I, or d) the reaction of a compound of the formula

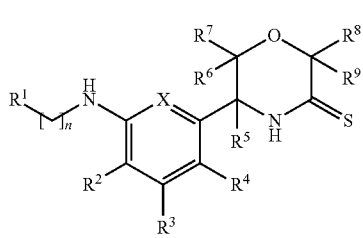
(VII)

in which X, $R^1$, $R^2$, $R^3$, $R^4$, $R^5$, $R^6$, $R^7$, $R^8$, $R^9$ and n are as defined for the formula I, in free form or in salt form, with ammonia, and thereafter e) the optional reduction, oxidation or other functionalisation of the resulting compound, f) the cleavage of any protecting group(s) optionally present, g) the recovery of the so obtainable compound of the formula I in free form or in salt form, and/or h) the optional separation of a mixture of optical isomers into their individual optical isomers.

The above reactions can be effected according to conventional methods. For example, the reaction described in step (a) may be carried out in the presence of a suitable solvent, for example tert-butanol, and at a suitable temperature, for example 0 to 150° C., more suitably 80 to 120° C.

The reaction described in step (b) may be carried out in the presence of a suitable solvent, for example methanol or THF, a suitable reducing agent, for example sodium borohydride or LiAlH$_4$, and at a suitable temperature, for example −80 to 150° C., more suitably 0 to 80° C.

The reaction described in step (c) may be carried out in the presence of, a suitable catalyst, for example tris(dibenzylidene-acetone)di palladium, a suitable ligand, for example Xanthphos, a suitable base, for example cesium carbonate, a suitable solvent, for example 1,4-dioxane, and at a suitable temperature, for example 10 to 100° C., more suitably 30 to 85° C.

The reaction described in step (d) may be carried out in the presence of a suitable solvent, for example methanol, and at a suitable temperature, for example 0 to 50° C., more suitably 0 to 30° C.

The compounds of the formulae (II), (III), (IV), (V), (VI) and (VII) are known or may be prepared according to conventional procedures starting from known compounds, may be prepared from known compounds as described in the Examples, or may be prepared using procedures analogous to those described in the Examples.

The further optional reduction, oxidation or other functionalisation of compounds of formula (I) may be carried out according to methods well know to those skilled in the art.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/1, Georg Thieme Verlag, Stuttgart 1974, and in H.- D. Jakubke and H. Jeschkeit, "Aminosauren, Peptide, Proteine" (Amino acids, Peptides, Proteins), Verlag Chemie, Weinheim, Deerfield Beach, and Basel 1982. A characteristic of protecting groups is that they can be removed readily (i.e. without the occurrence of undesired secondary reactions) for example by solvolysis, reduction, photolysis or alternatively under physiological conditions (e.g. by enzymatic cleavage). Salts of compounds of the present invention having at least one salt-forming group may be prepared in a manner known to those skilled in the art. For example, acid addition salts of compounds of the present invention are obtained in customary manner, e.g. by treating the compounds with an acid or a suitable anion exchange reagent.

Salts can be converted into the free compounds in accordance with methods known to those skilled in the art. Acid addition salts can be converted, for example, by treatment with a suitable basic agent.

Any resulting mixtures of isomers can be separated on the basis of the physicochemical differences of the constituents, into the pure or substantially pure geometric or optical isomers, diastereomers, racemates, for example, by chromatography and/or fractional crystallization.

For those compounds containing an asymmetric carbon atom, the compounds exist in individual optically active isomeric forms or as mixtures thereof, e.g. as racemic or diastereomeric mixtures. Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Enantiomers can also be separated by use of a commercially available chiral HPLC column.

The invention further includes any variant of the present processes, in which the reaction components are used in the form of their salts or optically pure material. Compounds of the invention and intermediates can also be converted into each other according to methods generally known to those skilled in the art.

Compounds of the formula (I), in free form or in pharmaceutically acceptable salt form, hereinafter often referred to as "agents of the invention", exhibit valuable pharmacological properties, when tested in vitro, and may, therefore, be useful in medicaments, in therapy or for use as research chemicals, for example as tool compounds.

For example, agents of the invention are inhibitors of BACE-1 and BACE-2 and may be used for the treatment or prevention of a condition, disease or disorder involving processing by such enzymes, particularly the generation of beta-amyloid and the subsequent aggregation into oligomers and fibrils, and loss of β cell mass and/or function.

The inhibiting properties of an agent of the invention towards proteases can be evaluated in the tests as described hereinafter.

Test 1: Inhibition of Human BACE-1

Recombinant BACE-1 (extracellular domain, expressed in baculovirus and purified using standard methods) at 0.1 to 1 nM concentrations is incubated with the test compound at various concentrations for 1 hour at room temperature in 100 mM acetate buffer, pH 4.5, containing 0.1% CHAPS. Activity was measured using a final concentration of 3 μM of the fluorescence-quenched substrate Q-C(HSO$_3$)-Ile-Asp-Leu-Ala-Val-Leu-Asp-HN—CH$_2$—CH$_2$-Mca, where Q=2-nitro-5-amino benzoic acid and Mca=7-methoxy-4-coumarinyl acetic acid. Catalytic turnover was monitored in a Spectramax Gemini fluorescence plate reader (Molecular Devices) in black 96-well microplates using excitation/emission wavelength of 325 nm and 400 nm, respectively. Fluorescence increase was followed for 15 min, in 1 minute's intervals. The fluorescence/time slopes were calculated from duplicate wells and from wells without inhibitor and the IC$_{50}$ values were calculated using a logistic 4-parameter model.

Test 2: Inhibition of Human BACE-2

Recombinant BACE-2 (extracellular domain, expressed in baculovirus and purified using standard methods) at 0.1 to 1 nM concentrations is incubated with the test compound at various concentrations for 1 hour at room temperature in 100 mM acetate buffer, pH 4.5, containing 0.1% CHAPS. Activity was measured using a final concentration of 3 µM of the fluorescence-quenched substrate Q-C(HSO$_3$)-Ile-Asp-Leu-Ala-Val-Leu-Asp-HN—CH$_2$—CH$_2$-Mca, where Q=2-nitro-5-amino benzoic acid and Mca=7-methoxy-4-coumarinyl acetic acid. Catalytic turnover was monitored in a Spectramax Gemini fluorescence plate reader (Molecular Devices) in black 96-well microplates using excitation/emission wavelength of 325 nm and 400 nm, respectively. Fluorescence increase was followed for 15 min, in 1 minute's intervals. The fluorescence/time slopes were calculated from duplicate wells and from wells without inhibitor and the IC$_{50}$ values were calculated using a logistic 4-parameter model.

Test 3: Inhibition of Human Cathepsin D

Recombinant cathepsin D (expressed as procathepsin D in baculovirus, purified using standard methods and activated by incubation in sodium formate buffer pH 3.7) is incubated with the test compound at various concentrations for 1 hour at room temperature in sodium formate or sodium acetate buffer at a suitable pH within the range of pH 3.0 to 5.0. Synthetic peptide substrate Mca-Gly-Lys-Pro-Ile-Leu-Phe-Phe-Arg-Leu-Lys(DNP)-D-Arg-NH$_2$ is added to a final concentration of 1 to 5 µM, and the increase in fluorescence is recorded at excitation of 325 nm and emission at 400 nm in a microplate spectro-fluorimeter for 5 to 30 minutes in 1-minute intervals. IC$_{50}$ values are calculated from the percentage of inhibition of cathepsin D-activity as a function of the test compound concentration.

Test 4: Inhibition of Cellular Release of Amyloid Peptide 1-40

Chinese hamster ovary cells are transfected with the human gene for amyloid precursor protein. The cells are plated at a density of 8000 cells/well into 96-well microtiter plates and cultivated for 24 hours in DMEM cell culture medium containing 10% FCS. The test compound is added to the cells at various concentrations, and the cells are cultivated for 24 hours in the presence of the test compound. The supernatants are collected, and the concentration of amyloid peptide 1-40 is determined using state of the art immunoassay techniques, for example sandwich ELISA, homogenous time-resolved fluorescence (HTRF) immunoassay, or electro-chemiluminescence immunoassay. The potency of the compound is calculated from the percentage of inhibition of amyloid peptide release as a function of the test compound concentration.

Agents of the invention were tested in at least one of the above-described tests.

The compounds of the Examples show the IC$_{50}$ values presented in Table 1 below when tested in Test 1 as described hereinbefore.

TABLE 1

| Example | BACE-1 IC$_{50}$ [µM] |
|---------|-----------------------|
| 1 | 1.5 |
| 2 | 5.2 |
| 3 | 8.9 |
| 4 | 1.9 |
| 5 | 3.6 |
| 6 | 6.2 |
| 7 | 0.036 |
| 8 | 0.021 |
| 9 | 0.018 |
| 10 | 0.6 |
| 11 | 1.9 |
| 12 | 0.35 |
| 13 | 1.4 |
| 14 | 0.57 |
| 15 | 0.3 |
| 16 | 8.6 |
| 17 | 1.8 |
| 18 | 2.4 |
| 19 | 1.3 |
| 20 | 1.3 |
| 21 | 1.5 |
| 22 | 0.97 |
| 23 | 0.04 |
| 24 | 0.083 |
| 25 | 0.21 |
| 26 | 2.9 |
| 27 | 3.0 |
| 28 | 0.068 |
| 29 | >10 |
| 30 | 1.5 |
| 31 | 6.4 |
| 32 | >10 |

The compounds of the Examples show the IC$_{50}$ values presented in Table 2 below when tested in Test 2 as described hereinbefore.

TABLE 2

| Example | BACE-2 IC$_{50}$ [µM] |
|---------|-----------------------|
| 1 | 1.9 |
| 2 | >10 |
| 3 | 3.2 |
| 4 | 2.4 |
| 5 | 5.3 |
| 6 | 8.3 |
| 7 | 0.032 |
| 8 | 0.011 |
| 9 | 0.03 |
| 10 | 8.2 |
| 11 | 5.6 |
| 12 | 0.072 |
| 13 | 0.41 |
| 14 | 1.4 |
| 15 | 0.089 |
| 16 | >10 |
| 17 | 0.67 |
| 18 | 1.3 |
| 19 | 0.16 |
| 20 | 0.22 |
| 21 | 0.56 |
| 22 | 0.34 |
| 23 | 0.011 |
| 24 | 0.28 |
| 25 | 0.027 |
| 26 | 1.4 |
| 27 | 0.66 |
| 28 | 0.2 |
| 29 | 4.2 |
| 30 | 1.6 |
| 31 | 1.7 |
| 32 | >10 |

The compounds of the Examples show the IC$_{50}$ values presented in Table 3 below when tested in Test 4 as described hereinbefore.

TABLE 3

| Example | Amyloid-β1-40 release IC$_{50}$ [μM] |
|---|---|
| 1 | 2.9 |
| 2 | 3.5 |
| 3 | 7.1 |
| 4 | 0.38 |
| 5 | 1.4 |
| 6 | 0.74 |
| 7 | 0.022 |
| 8 | 0.033 |
| 9 | 0.005 |
| 10 | 0.024 |
| 11 | 0.25 |
| 12 | 0.086 |
| 13 | 0.26 |
| 14 | 0.22 |
| 15 | 0.056 |
| 16 | 2.3 |
| 17 | 0.4 |
| 18 | 0.67 |
| 19 | 0.31 |
| 20 | 0.53 |
| 21 | 0.43 |
| 22 | 0.24 |
| 23 | 0.051 |
| 24 | 0.046 |
| 25 | 0.22 |
| 26 | 0.69 |
| 27 | 2.0 |
| 28 | 0.15 |
| 29 | 2.3 |
| 30 | 0.15 |
| 31 | 1.0 |
| 32 | 8.3 |

The compounds [3-((R)-5-amino-3-methyl-3,6-dihydro-2H-[1,4]oxazin-3-yl)-phenyl]-(1H-indazol-3-yl)-amine and N*4*-[3-((R)-5-amino-3-difluoromethyl-3,6-dihydro-2H-[1,4]oxazin-3-yl)-4-fluoro-phenyl]-5-methoxy-pyrimidine-2,4-diamine were also tested and found to have IC$_{50}$ values greater than 10 μM in Tests 1, 2 and 4. N-[3-((R)-5-amino-3-difluoromethyl-3,6-dihydro-2H-[1,4]oxazin-3-yl)-4-fluoro-phenyl]-5-methoxy-pyrimidine-4,6-diamine was tested in Tests 1 and 2 and found to have an IC$_{50}$ value greater than 10 μM in both tests.

Due to their inhibiting properties towards proteases, and BACE-1 in particular, agents of the invention may be useful, e. g., in the treatment or prevention of a variety of disabilitating psychiatric, psychotic, neurological or vascular states, e. g. of a condition, disease or disorder of the vascular system or of the nervous system, in which beta-amyloid generation or aggregation plays a role. Based on the inhibition of BACE-2 (beta-site APP-cleaving enzyme 2) or cathepsin D, which are close homologues of the pepsin-type aspartyl proteases and beta-secretase, and the correlation of BACE-2 or cathepsin D expression with a more tumorigenic or metastatic potential of tumor cells, the agents of the invention may also be useful as anti-cancer medicaments, e. g. in the suppression of the metastasis process associated with tumor cells. Furthermore, based on the inhibition of BACE-2 and the correlation of BACE-2 activity with TME27 cleavage and β cell mass, the agents of the invention may also be useful for treating or preventing loss of β cell mass and/or function, e.g. in the treatment of diabetes.

The said condition, disease or disorder of the vascular system or of the nervous system is exemplified by, and includes, without limitation, an anxiety disorder, such as panic disorder with or without agoraphobia, agoraphobia without history of panic disorder, an animal or other specific phobia, including a social phobia, social anxiety disorder, anxiety, obsessive-compulsive disorder, a stress disorder, including post-traumatic or acute stress disorder, or a generalized or substance-induced anxiety disorder; a neurosis; seizures; epilepsy, especially partial seizures, simple, complex or partial seizures evolving to secondarily generalized seizures or generalized seizures [absence (typical or atypical), myoclonic, clonic, tonic, tonic-clonic or atonic seizures]; convulsions; migraine; an affective disorder, including a depressive or bipolar disorder, e. g. single-episode or recurrent major depressive disorder, major depression, a dysthymic disorder, dysthymia, depressive disorder NOS, bipolar I or bipolar II manic disorder or cyclothymic disorder; a psychotic disorder, including schizophrenia or depression; neurodegeneration, e. g. neurodegeneration arising from cerebral ischemia; an acute, traumatic or chronic degenerative process of the nervous system, such as Parkinson's disease, Down's syndrome, dementia, e. g. senile dementia, dementia with Lewy bodies or a fronto-temporal dementia, a cognitive disorder, cognitive impairment, e. g. mild cognitive impairment, memory impairment, an amyloid neuropathy, a peripheral neuropathy, Alzheimer's disease, Gerstmann-Straeussler-Scheinker syndrome, Niemann-Pick disease, e. g. Niemann-Pick type C disease, brain inflammation, a brain, spinal cord or nerve injury, e. g. traumatic brain injury (TBI), a nerve trauma or a brain trauma, vascular amyloidosis, cerebral haemorrhage with amyloidosis, Huntington's chorea, amyotrophic lateral sclerosis, multiple sclerosis or fragile X syndrome; scrapie; cerebral amyloid angiopathy; an encephalopathy, e. g. transmissible spongiform encephalopathy; stroke; an attention disorder, e. g. attention deficit hyperactivity disorder; Tourette's syndrome; a speech disorder, including stuttering; a disorder of the circadian rhythm, e. g. in subjects suffering from the effects of jet lag or shift work; pain; nociception; itch; emesis, including acute, delayed or anticipatory emesis, such as emesis induced by chemotherapy or radiation, motion sickness, or post-operative nausea or vomiting; an eating disorder, including anorexia nervosa or bulimia nervosa; premenstrual syndrome; a muscle spasm or spasticity, e. g. in paraplegic patients; a hearing disorder, e. g. tinnitus or age-related hearing impairment; urinary incontinence; glaucoma; inclusion-body myositis; or a substance-related disorder, including substance abuse or dependency, including a substance, such as alcohol, withdrawal disorder. Agents of the invention may also be useful in enhancing cognition, e. g. in a subject suffering from a dementing condition, such as Alzheimer's disease; as premedication prior to anaesthesia or a minor medical intervention, such as endoscopy, including gastric endoscopy; or as ligands, e. g. radioligands or positron emission tomography (PET) ligands.

Due to their inhibiting properties towards BACE-2, compounds of the invention may be useful in the treatment or prevention a disease or disorder mediated by BACE-2. Diseases and disorders associated with BACE-2 include: metabolic syndrome (such as dyslipidemia, obesity, insulin resistance, hypertension, microalbuminemia, hyperuricaemia, and hypercoagulability), insulin resistance, glucose intolerance (also known as impaired glucose tolerance or impaired glucose tolerance, IGT), obesity, hypertension, or diabetic complications (such as retinopathy, nephropathy, diabetic foot, ulcers, macroangiopathies, metabolic acidosis or ketosis, reactive hypoglycaemia, hyperinsulinaemia), glucose metabolic disorder, dyslipidaemias of different origins, atherosclerosis and related diseases, high blood pressure, chronic heart failure, Syndrome X, diabetes, non-insulindependent diabetes mellitus, type 2 diabetes, Type 1 diabetes, body weight disorders, weight loss, body mass index and leptin related diseases.

Compounds of the invention may be suitable for preventing beta-cell degeneration such as apoptosis or necrosis of pancreatic beta cells, for improving or restoring the functionality of pancreatic cells, and/or increasing the number and/or size of pancreatic beta cells.

As used herein a patient is suffering from "obesity" if the patient exhibits at least one of:
- a body mass index (BMI), i.e. the patient's mass (in kg) divided by the square of the patient's height (in m), of 30 or more;
- an absolute waist circumference of >102 cm in men or >88 cm in women;
- a waist-to-hip ratio >0.9 in men or >0.85 in women; or
- a percent body fat >25% in men or >30% in women.

As used herein a patient is suffering from "type 2 diabetes" if they meet the World Health Organisation criteria for Diabetes diagnosis (Definition and diagnosis of diabetes mellitus and intermediate hyperglycaemia, WHO, 2006), i.e. the patient exhibits at least one of:
- a fasting plasma glucose ≥7.0 mmol/l (126 mg/dl); or
- a venous plasma glucose ≥11.1 mmol/l (200 mg/dl) 2 hours after ingestion of 75 g oral glucose load.

As used herein a patient is suffering from "IGT" if they meet the World Health Organisation criteria for IGT diagnosis (Definition and diagnosis of diabetes mellitus and intermediate hyperglycaemia, WHO, 2006), i.e. the patient exhibits both of:
- a fasting plasma glucose <7.0 mmol/l (126 mg/dl); and
- a venous plasma glucose ≥7.8 and <11.1 mmol/l (200 mg/dl) 2 hours after ingestion of 75 g oral glucose load.

As used herein, the term "metabolic syndrome" is a recognized clinical term used to describe a condition comprising combinations of Type II diabetes, impaired glucose tolerance, insulin resistance, hypertension, obesity, increased abdominal girth, hypertriglyceridemia, low HDL, hyperuricaemia, hypercoagulability and/or microalbuminemia. The American Heart Association has published guidelines for the diagnosis of metabolic syndrome, Grundy, S., et. al., (2006) *Cardiol. Rev.* Vol. 13, No. 6, pp. 322-327.

For the above-mentioned indications, the appropriate dosage will vary depending on, e. g., the compound employed as active pharmaceutical ingredient, the host, the mode of administration, the nature and severity of the condition, disease or disorder or the effect desired. However, in general, satisfactory results in animals are indicated to be obtained at a daily dosage of from about 0.1 to about 100, preferably from about 1 to about 50, mg/kg of animal body weight. In larger mammals, for example humans, an indicated daily dosage is in the range of from about 0.5 to about 2000, preferably from about 2 to about 200, mg of an agent of the invention conveniently administered, for example, in divided doses up to four times a day or in sustained release form.

An agent of the invention may be administered by any conventional route, in particular enterally, preferably orally, e. g. in the form of a tablet or capsule, or parenterally, e. g. in the form of an injectable solution or suspension.

In a further aspect, the invention relates to a pharmaceutical composition comprising an agent of the invention as active pharmaceutical ingredient in association with at least one pharmaceutically acceptable carrier or diluent and optionally in association with other auxiliary substances, such as inhibitors of cytochrome P450 enzymes, agents preventing the degradation of active pharmaceutical ingredients by cytochrome P450, agents improving or enhancing the pharmacokinetics of active pharmaceutical ingredients, agents improving or enhancing the bioavailability of active pharmaceutical ingredients, and so on, e. g. grapefruit juice, ketoconazole or, preferably, ritonavir. Such a composition may be manufactured in conventional manner, e. g. by mixing its components. Unit dosage forms contain, e. g., from about 0.1 to about 1000, preferably from about 1 to about 500, mg of an agent of the invention.

In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

In accordance with the foregoing, in a further aspect, the invention relates to an agent of the invention for use as a medicament, for example for the treatment or prevention of a neurological or vascular condition, disease or disorder, in which beta-amyloid generation or aggregation plays a role, or for the suppression of the metastasis process associated with tumor cells, or for the treatment or prevention of loss of β cell mass and/or function. In one embodiment, the invention relates to an agent of the invention for use in the treatment of a disease or disorder mediated by BACE-1, BACE-2 or cathepsin D activity. In another embodiment, the invention relates to an agent of the invention for use in the treatment or prevention of Alzheimer's Disease or mild cognitive impairment. In a further embodiment, the invention relates to an agent of the invention for use in the treatment or prevention of insulin resistance, glucose intolerance, type 2 diabetes, obesity, hypertension, or diabetic complications. In yet another embodiment, the invention relates to an agent of the invention for use in the treatment of impaired glucose tolerance or type 2 diabetes.

In a further aspect, the invention relates to the use of an agent of the invention as an active pharmaceutical ingredient in a medicament, for example for the treatment or prevention of a neurological or vascular condition, disease or disorder, in which beta-amyloid generation or aggregation plays a role, or for the suppression of the metastasis process associated with tumor cells, or for the treatment or prevention of loss of β cell mass and/or function. In a further embodiment, the invention relates to the use of an agent of the invention as an active pharmaceutical ingredient in a medicament for the treatment or prevention of a disease or disorder mediated by BACE-1, BACE-2 or cathepsin D activity. In one embodiment, the invention relates to the use of an agent of the invention as an active pharmaceutical ingredient in a medicament for the treatment or prevention of Alzheimer's Disease or mild cognitive impairment. In a further embodiment, the invention relates to the use of an agent of the invention as an active pharmaceutical ingredient in a medicament for the treatment or prevention of insulin resistance, glucose intolerance, type 2 diabetes, obesity, hypertension, or diabetic complications. In yet a further embodiment, the invention relates to the use of an agent of the invention as an active pharmaceutical ingredient in a medicament for the treatment or prevention of impaired glucose tolerance or type 2 diabetes.

In a further aspect, the invention relates to the use of an agent of the invention for the manufacture of a medicament for the treatment or prevention of a neurological or vascular condition, disease or disorder, in which beta-amyloid generation or aggregation plays a role, or for the suppression of the metastasis process associated with tumor cells, or for the treatment or prevention of loss of β cell mass and/or function. In a further embodiment, the invention relates to the use of an agent of the invention for the manufacture of a medicament for the treatment or prevention of a disease or disorder mediated by BACE-1, BACE-2 or cathepsin D activity. In one embodiment, the invention relates to the use of an agent of the invention for the manufacture of a medicament for the treatment or prevention of Alzheimer's Disease or mild cognitive impairment. In a further embodiment, the invention relates to the use of an agent of the invention for the manufacture of a medicament for the treatment or prevention of insulin resistance, glucose intolerance, type 2 diabetes, obesity, hypertension, or diabetic complications. In yet a further embodiment, the invention relates to the use of an agent of the invention for the manufacture of a medicament for the treatment or prevention of impaired glucose tolerance or type 2 diabetes.

In a further aspect, the invention relates to a method for the treatment or prevention of a neurological or vascular condition, disease or disorder, in which beta-amyloid generation or aggregation plays a role, or for the suppression of the metastasis process associated with tumor cells, or for the treatment or prevention of loss of β cell mass and/or function, in a subject in need of such treatment, prevention or suppression, which method comprises administering to such subject an effective amount of an agent of the invention. In one embodiment, the invention relates to a method of modulating BACE-1, BACE-2 or cathepsin D activity in a subject, wherein the method comprises administering to the subject a therapeutically effective amount of an agent of the invention. In another embodiment, the invention relates to a method for the treatment or prevention of a disease mediated by BACE-1, BACE-2 or cathepsin D activity, in a subject in need of such treatment or prevention, which method comprises administering to such subject an effective amount of an agent of the invention. In yet another embodiment, the invention relates to a method for the treatment or prevention of Alzheimer's Disease or mild cognitive impairment, in a subject in need of such treatment or prevention, which method comprises administering to such subject an effective amount of an agent of the invention. In a further embodiment, the invention relates to a method for the treatment or prevention of insulin resistance, glucose intolerance, type 2 diabetes, obesity, hypertension, or diabetic complications, in a subject in need of such treatment or prevention, which method comprises administering to such subject a therapeutically effective amount of an agent of the invention. In yet a further embodiment, the invention relates to a method for the treatment or prevention of impaired glucose tolerance or type 2 diabetes, in a subject in need of such treatment or prevention, which method comprises administering to such subject a therapeutically effective amount of an agent of the invention.

An agent of the invention can be administered as sole active pharmaceutical ingredient or as a combination with at least one other active pharmaceutical ingredient effective, e. g., in the treatment or prevention of a neurological or vascular condition, disease or disorder, in which beta-amyloid generation or aggregation plays a role, or in the suppression of the metastasis process associated with tumor cells, or in the treatment or prevention of loss of β cell mass and/or function. Such a pharmaceutical combination may be in the form of a unit dosage form, which unit dosage form comprises a predetermined quantity of each of the at least two active components in association with at least one pharmaceutically acceptable carrier or diluent. Alternatively, the pharmaceutical combination may be in the form of a package comprising the at least two active components separately, e. g. a pack or dispenser-device adapted for the concomitant or separate administration of the at least two active components, in which these active components are separately arranged. In a further aspect, the invention relates to such pharmaceutical combinations.

In a further aspect, the invention therefore relates to a combination comprising a therapeutically effective amount of an agent of the invention and a second drug substance, for simultaneous or sequential administration.

In one embodiment, the invention provides a product comprising an agent of the invention and at least one other therapeutic agent as a combined preparation for simultaneous, separate or sequential use in therapy. In one embodiment, the therapy is the treatment of a disease or condition mediated by BACE-1, BACE-2 or cathepsin D activity, such as Alzheimer's Disease, mild cognitive impairment, impaired glucose tolerance or type 2 diabetes.

In one embodiment, the invention provides a pharmaceutical composition comprising an agent of the invention and another therapeutic agent(s), in association with at least one pharmaceutically acceptable carrier or diluent.

In one embodiment, the invention provides a kit comprising two or more separate pharmaceutical compositions, at least one of which contains an agent of the invention. In one embodiment, the kit comprises means for separately retaining said compositions, such as a container, divided bottle, or divided foil packet. An example of such a kit is a blister pack, as typically used for the packaging of tablets, capsules and the like. The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the agent of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent. Accordingly, the invention provides an agent of the invention for use in the treatment of a disease or condition mediated by BACE-1, BACE-2 or cathepsin D activity, such as Alzheimer's Disease, impaired glucose tolerance or type 2 diabetes, wherein the medicament is prepared for administration with another therapeutic agent. The invention also provides the use of another therapeutic agent for treating a disease or condition mediated by BACE-1, BACE-2 or cathepsin D activity, such as Alzheimer's Disease, impaired glucose tolerance or type 2 diabetes, wherein the medicament is administered with an agent of the invention.

The invention also provides an agent of the invention for use in a method of treating a disease or condition mediated by BACE-1, BACE-2 or cathepsin D activity, such as Alzheimer's Disease, impaired glucose tolerance or type 2 diabetes, wherein the agent of the invention is prepared for administration with another therapeutic agent. The invention also provides another therapeutic agent for use in a method of treating a disease or condition mediated by BACE-1, BACE-2 or cathepsin D activity, such as Alzheimer's Disease, impaired glucose tolerance or type 2 diabetes, wherein the other therapeutic agent is prepared for administration with an agent of the invention. The invention also provides an agent of the invention for use in a method of treating a disease or condition mediated by BACE-1, BACE-2 or cathepsin D activity, such as Alzheimer's Disease, impaired glucose tolerance or type 2 diabetes, wherein the agent of the invention is administered with another therapeutic agent. The invention also provides another therapeutic agent for use in a method of treating a disease or condition mediated by BACE-1, BACE-2 or cathepsin D activity, such as Alzheimer's Disease, impaired glucose tolerance or type 2 diabetes, wherein the other therapeutic agent is administered with an agent of the invention.

The invention also provides the use of an agent of the invention for treating a disease or condition mediated by BACE-1, BACE-2 or cathepsin D activity, such as Alzheimer's Disease, impaired glucose tolerance or type 2 diabetes, wherein the patient has previously (e.g. within 24 hours) been treated with another therapeutic agent. The invention also provides the use of another therapeutic agent for treating a disease or condition mediated by BACE-1, BACE-2 or cathepsin D activity, such as Alzheimer's Disease, impaired glucose tolerance or type 2 diabetes, wherein the patient has previously (e.g. within 24 hours) been treated with an agent of the invention.

In one embodiment, the invention relates to a compound of the invention, or a pharmaceutically acceptable salt thereof, in combination with another therapeutic agent wherein the other therapeutic agent is selected from:

(a) acetylcholinesterase inhibitors, such as donepezil (Aricept™), rivastigmine (Exelon™) and galantamine (Razadyne™);

(b) glutamate antagonists, such as memantine (Namenda™);

(c) antidepressant medications for low mood and irritability, such as citalopram (Celexa™), fluoxetine (Prozac™), paroxeine (Paxil™), sertraline (Zoloft™) and trazodone (Desyrel™);

(d) anxiolytics for anxiety, restlessness, verbally disruptive behavior and resistance, such as lorazepam (Ativan™) and oxazepam (Serax™);

(e) antipsychotic medications for hallucinations, delusions, aggression, agitation, hostility and uncooperativeness, such as aripiprazole (Abilify™), clozapine (Clozaril™), haloperidol (Haldol™), olanzapine (Zyprexa™), quetiapine (Seroquel™), risperidone (Risperdal™) and ziprasidone (Geodon™);

(f) mood stabilizers, such as carbamazepine (Tegretol™) and divalproex (Depakote™);

(g) nicotinic apha-7 agonists;

(h) mGluR5 antagonists;

(i) H3 agonists; and (j) amyloid therapy vaccines.

Thus, in one embodiment, the invention provides a pharmaceutical composition comprising;

i) a compound of the invention, or a pharmaceutically acceptable salt thereof, and ii) at least one compound selected from
a) acetylcholinesterase inhibitors,
b) glutamate antagonists,
c) antidepressant medications,
d) anxiolytics,
e) antipsychotic medications,
f) mood stabilizers,
g) nicotinic apha-7 agonists,
h) mGluR5 antagonists,
i) H3 agonists,
j) amyloid therapy vaccines, and ii) one or more pharmaceutically acceptable carrier or diluent.

In another embodiment, the invention relates to a compound of the invention, or a pharmaceutically acceptable salt thereof, in combination with another therapeutic agent wherein the other therapeutic agent is selected from:

a) antidiabetic agents, such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; protein tyrosine phosphatase-1B (PTP-1B) inhibitors such as PTP-112; GSK3 (glycogen synthase kinase-3) inhibitors such as SB-517955, SB-4195052, SB-216763, NN-57-05441 and NN-57-05445; RXR ligands such as GW-0791 and AGN-194204; sodium-dependent glucose cotransporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; and DPPIV (dipeptidyl peptidase IV) inhibitors such as vildagliptin;

b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid bile acid binding resins such as cholestyramine; fibrates; nicotinic acid and other GPR109 agonists; cholesterol absorption inhibitors such as ezetimibe; CETP inhibitors (cholesterol-ester-transfer-protein inhibitors), and aspirin;

c) anti-obesity agents such as orlistat, sibutramine and Cannabinoid Receptor 1 (CB1) antagonists e.g. rimonabant; and d) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na-K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors.

e) agonists of peroxisome proliferator-activator receptors, such as fenofibrate, pioglitazone, rosiglitazone, tesaglitazar, BMS-298585, L-796449, the compounds specifically described in the patent application WO 2004/103995 i.e. compounds of examples 1 to 35 or compounds specifically listed in claim 21, or the compounds specifically described in the patent application WO 03/043985 i.e. compounds of examples 1 to 7 or compounds specifically listed in claim 19 and especially (R)-1-{4-[5-methyl-2-(4-trifluoromethylphenyl)-oxazol-4-ylmethoxy]-benzenesulfonyl}-2,3-dihydro-1H-indole-2-carboxylic or a salt thereof.

Thus, in one embodiment, the invention provides a pharmaceutical composition comprising;

i) a compound of the invention, or a pharmaceutically acceptable salt thereof, and ii) at least one compound selected from
a) antidiabetic agents,
b) hypolipidemic agents,
c) anti-obesity agents,
d) anti-hypertensive agents,
e) agonists of peroxisome proliferator-activator receptors, and ii) one or more pharmaceutically acceptable carrier or diluent.

Other specific anti-diabetic compounds are described by Patel Mona in *Expert Opin Investig Drugs,* 2003, 12(4), 623-633, in the FIGS. 1 to 7.

The structure of the therapeutic agents identified by code numbers, generic or trade names may be taken from the actual edition of the standard compendium "The Merck Index" or from databases, e.g., Patents International (e.g. IMS World Publications).

EXAMPLES

Abbreviations

ACN acetonitrile
aq aqueous

Boc tert-butoxycarbonyl
DCM dichloromethane
DIPEA diisopropylethylamine
DMSO dimethylsulfoxide
DMTr 4,4'-dimethoxytrityl
EDC 1-(3-dimethylaminopropyl)-3-ethylcarbodiimide
eq equivalent(s)
ESIMS electrospray ionization mass spectrometry
Et ethyl
FC flash chromatography
h hour(s)
HPLC high performance liquid chromatography
HOAt 1-hydroxy-7-azabenzotriazole
Me methyl
min minute(s)
NMR nuclear magnetic resonance spectrometry
rt room temperature
$R_f$ retention factor (TLC)
Rt retention time
TBME tert-butyl-methyl-ether
TFA trifluoroacetic acid
THF tetrahydrofuran
NMR Methods Proton spectra are recorded on a Bruker ultrashield spectrometer unless otherwise noted. Chemical shifts are reported in ppm relative to methanol (δ 3.31), dimethyl sulfoxide (δ 2.50), or chloroform (δ 7.29). A small amount of the dry sample (1-5 mg) is dissolved in an appropriate deuterated solvent (0.7 mL). The shimming is automated and the spectra obtained in accordance with normal procedure.

General Chromatography Information

HPLC Method H1 ($Rt_{H1}$):
  HPLC-column dimensions: 3.0×30 mm
  HPLC-column type: Zorbax SB-C18, 1.8 μm
  HPLC-eluent: A) water+0.05 Vol.-% TFA, B) ACN+0.05 Vol.-% TFA
  HPLC-gradient: 0-100% B in 3.25 min, flow=0.7 ml/min
HPLC Method H2 ($Rt_{H2}$):
  HPLC-column dimensions: 3.0×30 mm
  HPLC-column type: Zorbax SB-C18, 1.8 μm
  HPLC-eluent: A) water+0.05 Vol.-% TFA, B) ACN+0.05 Vol.-% TFA
  HPLC-gradient: 10-100% B in 3.25 min, flow=0.7 ml/min
HPLC Method H3 ($Rt_{H3}$):
  HPLC-column dimensions: 3.0×30 mm
  HPLC-column type: Zorbax SB-C18, 1.8 μm
  HPLC-eluent: A) water+0.05 Vol.-% TFA, B) ACN+0.05 Vol.-% TFA
  HPLC-gradient: 30-100% B in 3.25 min, flow=0.7 ml/min
HPLC Method H4 ($Rt_{H4}$):
  HPLC-column dimensions: 3.0×30 mm
  HPLC-column type: Zorbax SB-C18, 1.8 μm
  HPLC-eluent: A) water+0.05 Vol.-% TFA, B) ACN+0.05 Vol.-% TFA
  HPLC-gradient: 40-100% B in 3.25 min, flow=0.7 ml/min
LCMS Method H5 ($Rt_{H5}$):
HPLC-column dimensions: 3.0×30 mm
HPLC-column type: Zorbax SB-C8, 1.8 μm
HPLC-eluent: A) water+0.05 Vol.-% TFA, B) ACN+0.05 Vol.-% TFA
HPLC-gradient: 10-95% B in 2.00 min, 95% B 2.00 min, flow=0.7 ml/min
UPLC Method H6 ($Rt_{H6}$):
  HPLC-column dimensions: 2.1×50 mm
  HPLC-column type: Acquity UPLC HSS T3 C18, 1.7 μm
  HPLC-eluent: A) water+0.1 Vol.-% TFA, B) ACN+0.1 Vol.-% TFA
  HPLC-gradient: 5-100% B in 1.5 min, flow=1.0 ml/min
UPLC method H8 ($Rt_{H8}$):
  HPLC-column dimensions: 2.1×50 mm
  HPLC-column type: Acquity UPLC HSS T3, 1.8 μm
  HPLC-eluent: A) water+0.05 Vol.-% formic acid+3.75 mM ammonium acetate, B) ACN+0.04 Vol.-% formic acid
  HPLC-gradient: 10-95% B in 1.5 min, 1.0 min 95% B, flow=1.2 ml/min
  HPLC-column temperature: 50° C.
UPLC Method H9 ($Rt_{H9}$):
  HPLC-column dimensions: 2.1×50 mm
  HPLC-column type: Acquity UPLC HSS T3, 1.8 μm
  HPLC-eluent: A) water+0.05 Vol.-% formic acid+3.75 mM ammonium acetate, B) ACN+0.04 Vol.-% formic acid
  HPLC-gradient: 2-98% B in 1.4 min, 98% B 0.75 min, flow=1.2 ml/min
  HPLC-column temperature: 50° C.
UPLC Method H10 ($Rt_{H10}$):
  HPLC-column dimensions: 2.1×50 mm
  HPLC-column type: Acquity UPLC HSS T3, 1.8 μm
  HPLC-eluent: A) water+0.05 Vol.-% formic acid+3.75 mM ammonium acetate, B) ACN+0.04 Vol.-% formic acid
  HPLC-gradient: 5-98% B in 1.4 min, 98% B 0.4 min, flow=1.0 ml/min
  HPLC-column temperature: 50° C.

Example 1

[3-(5-Amino-3-methyl-3,6-dihydro-2H-[1,4]oxazin-3-yl)-phenyl]-(6-bromo-benzo[d]isothiazol-3-yl)-amine

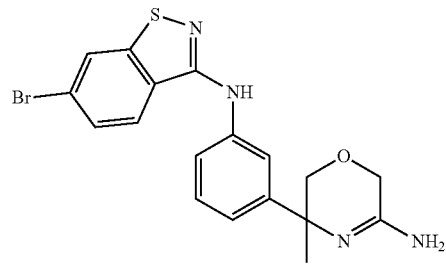 [SMILES: CC1(c2cccc(Nc3nsc4cc(Br)ccc34)c2)COCC(N)=N1]

a) 2-Amino-2-(3-bromo-phenyl)-propionitrile

A mixture of 1-(3-bromo-phenyl)-ethanone (10 g, 50 mmol), NH$_4$Cl (6.4 g, 100 mmol) and KCN (6.5 g, 100 mmol) was dissolved in ammonia (200 ml). The solution was stirred at room temperature for 3 days. The mixture was extracted with diethylether (3×300 ml). The organic phase was washed with water and brine, dried with Na$_2$SO$_4$ and concentrated in vacuo to yield the title compound (also containing some unreacted starting material).

$^1$H-NMR (400 MHz, CDCl$_3$): δ 7.84 (s, 1H), 7.59 (d, 1H), 7.48 (d, 1H), 7.28 (m, 1H), 1.75 (s, 3H).

b) 2-Amino-2-(3-bromo-phenyl)-propionic acid hydrochloride

2-Amino-2-(3-bromo-phenyl)-propionitrile (10 g, 44 mmol) was added to concentrated hydrochloric acid (100 ml) at room temperature. The mixture was refluxed overnight and then concentrated in vacuo to give a crude product, which was washed with EtOAc to yield the pure title compound.

¹H-NMR (400 MHz, CD₃OD): δ 7.62 (m, 2H), 7.48 (m, 2H), 1.82 (s, 3H).

c) 2-Amino-2-(3-bromo-phenyl)-propan-1-ol

NaBH₄ (38 g, 1.125 mol) was added at room temperature to a slurry of 2-amino-2-(3-bromo-phenyl)-propionic acid hydrochloride (105 g, 375 mmol) in dry THF. At 0° C. BF₃—O(C₂H₅)₂ (158 g, 1.125 mol) was added dropwise. The mixture was allowed to warm to room temperature, stirred for three days, quenched with 1M aqueous NaOH solution, concentrated in vacuo to remove the THF and extracted with EtOAc (3×300 ml). The organic phase was washed with 1M aqueous NaOH solution, dried with sodium sulfate and concentrated in vacuo to yield the title compound, which was used in the next reaction step without further purification.
¹H-NMR (400 MHz, CDCl₃): δ 7.61 (s, 1H), 7.35 (m, 2H), 7.21 (m, 1H), 3.58 (q, 2H), 1.42 (s, 3H).

d) N-[1-(3-Bromo-phenyl)-2-hydroxy-1-methyl-ethyl]-2-chloro-acetamide

2-Chloroacetyl chloride (2.24 g, 19.8 mmol) was added dropwise at 0° C. to a suspension of N-[1-(3-bromo-phenyl)-2-hydroxy-1-methyl-ethyl]-2-chloro-acetamide (3.8 g, 16.5 mmol), K₂CO₃ (4.55 g, 33 mmol) and dichloromethane (40 ml). The mixture was allowed to warm to room temperature over a period of approximately 3 h, washed with 1N hydrochloric acid and brine, dried with Na₂SO₄ and evaporated in vacuo to yield the crude title compound.
¹H-NMR (400 MHz, CDCl₃): δ 7.43 (m, 2H), 7.23 (m, 2H), 4.10-4.03 (m, 4H), 1.71 (s, 3H).

e) 5-(3-Bromo-phenyl)-5-methyl-morpholin-3-one

The crude N-[1-(3-bromo-phenyl)-2-hydroxy-1-methyl-ethyl]-2-chloro-acetamide (70 g, 230 mmol) was dissolved in tert-butanol (1 l). The solution was treated with portions of potassium tert-butoxide (52 g, 460 mmol). The mixture was refluxed for 30 min, after cooling quenched with water and evaporated. The residue was dissolved in EtOAc (500 ml) and washed with water and brine. The organic phase was dried with Na₂SO₄ and concentrated in vacuo to yield the crude title compound. The crude product was purified by chromatography on silica gel (PE/EtOAc=20:1 to 1:1) to give the title compound in the form of a grey solid.
¹H-NMR (400 MHz, DMSO-d₆): δ 8.66 (s, 1H), 7.60 (s, 1H), 7.48 (d, 1H), 7.44 (d, 1H), 7.34 (t, 1H), 4.02 (s, 2H), 3.92 (d, 1H), 3.68 (d, 1H), 1.38 (s, 3H).

f) 5-(3-Bromo-phenyl)-5-methyl-morpholine-3-thione

A solution of 5-(3-bromo-phenyl)-5-methyl-morpholin-3-one (18 g, 67 mmol) in dry THF was treated with Lawesson's reagent (27 g, 67 mmol) in one portion at room temperature. The mixture was refluxed for 2 h. The title compound was obtained by chromatography on silica gel (PE/EtOAc=30:1 to 10:1).
¹H-NMR (400 MHz, DMSO-d₆): δ 11.08 (s, 1H), 7.50 (m, 2H), 7.35 (m, 2H), 4.36 (s, 2H), 4.00 (m, 1H), 3.73 (m, 1H), 1.51 (s, 3H).

g) 5-(3-Bromo-phenyl)-5-methyl-5,6-dihydro-2H-[1,4]oxazin-3-ylamine

To a solution of 5-(3-bromo-phenyl)-5-methyl-morpholine-3-thione (5 g, 17.5 mmol) in MeOH/NH₃ (110 ml) were added at room temperature t-BuOOH (28 ml, 65%) and NH₄OH (47 ml, 25%). The mixture was stirred overnight, quenched with aqueous Na₂S₂O₃ solution, concentrated in vacuo to remove the methanol solution and extracted with EtOAc (3×30 ml). The organic phase was dried with Na₂SO₄ and concentrated in vacuo to give the crude product, which was purified by preparative HPLC [column: Venusil XBP-C18, 250×21.2 mm, 10 μm; injection volume: 10 ml/injection; mobile phase: CH₃CN/H₂O=10 to 35% (0.1% formic acid) gradient for 15 min, washed with 95% CH₃CN for 4 min, back to 10% balance for 4 min] to give the title compound in the form of a formic acid salt.
¹H-NMR (300 MHz, DMSO-d₆): δ 9.99 (s, 1H), 8.39 (s, 1H), 7.65 (s, 1H), 7.55 (d, 1H), 7.47 (d, 1H), 7.39 (t, 1H), 4.46 (s, 2H), 4.05 (d, 1H), 3.85 (d, 1H), 1.55 (s, 3H).

h) [5-(3-Bromo-phenyl)-5-methyl-5,6-dihydro-2H-[1,4]oxazin-3-yl]-carbamic acid tert-butyl ester A mixture of 5-(3-bromo-phenyl)-5-methyl-5,6-dihydro-2H-[1,4]oxazin-3-ylamine (4.73 g, 15 mmol) and dichloromethane was cooled to 0° C., treated with (Boc)₂O (4.26 g, 19.5 mmol) and DIPEA (2.91 g, 22.5 mmol) and stirred for 17 h at room temperature. 300 ml of water were added dropwise, the phases were separated, the aqueous phase was extracted twice with dichloromethane, and the combined organic phases were washed with 1M aqueous HCl solution and water, dried with Na₂SO₄ and evaporated under reduced pressure to yield the title compound.
MS: 369, 371 [(M+H)⁺];
¹H-NMR (500 MHz, DMSO-d₆): δ 9.58 (br, 1H), 7.62 (s, 1H), 7.40-7.25 (m, 3H), 4.50-4.30 (m, 2H), 3.75-3.35 (m, 2H), 1.45 (s, 3H), 1.41 (s, 9H).

i) [5-(3-Azido-phenyl)-5-methyl-5,6-dihydro-2H-[1,4]oxazin-3-yl]-carbamic acid tert-butyl ester

[5-(3-Bromo-phenyl)-5-methyl-5,6-dihydro-2H-[1,4]oxazin-3-yl]-carbamic acid tert-butyl ester (1.647 g, 25.3 mmol), sodium ascorbate (0.125 g, 0.63 mmol), copper iodide (0.241 g, 1.27 mmol) and (1R,2R)—N,N'-dimethyl-cyclohexane-1,2-diamine (0.270 g, 1.90 mmol) were dissolved in ethanol (17.7 ml) and water (7.6 ml). The mixture was stirred under N₂ at 90° C. for 4 h and then poured into 1M aqueous KHCO₃ solution. The mixture was extracted with EtOAc, and the organic phase was washed with brine, dried with Na₂SO₄ and evaporated under reduced pressure. The residue was purified by chromatography on silica gel (cyclohexane/EtOAc=7:3) to yield the title compound.
MS: 332 [(M+H)⁺];
¹H-NMR (500 MHz, DMSO-d₆): δ 9.57 (br, 1H), 7.38 (m, 1H), 7.24 (d, 1H), 7.18 (br, 1H), 7.0 (br, 1H), 4.50-4.30 (m, 2H), 3.75-3.35 (m, 2H), 1.41 (s, 9H), 1.36 (s, 3H).

j) [5-(3-Amino-phenyl)-5-methyl-5,6-dihydro-2H-[1,4]oxazin-3-yl]-carbamic acid tert-butyl ester A solution of [5-(3-azido-phenyl)-5-methyl-5,6-dihydro-2H-[1,4]oxazin-3-yl]-carbamic acid tert-butyl ester (497 mg, 1.50 mmol) in EtOAc (37 ml) was hydrogenated using Lindlar catalyst (10 h, room temperature). The mixture was filtered through Celite, and the filtrate was evaporated under reduced pressure yielding the title compound in the form of a colourless solid.
MS: 306 [(M+H)⁺];

¹H-NMR (500 MHz, DMSO-d₆): δ 9.57 (br, 1H), 6.97 (br, 1H), 6.55 (s, 1H), 6.52 (d, 1H), 6.45 (br, 1H), 5.08 (br, 2H), 4.40-4.30 (m, 2H), 3.75-3.45 (m, 2H), 1.47 (s, 3H), 1.39 (s, 9H).

k) {5-[3-(6-Bromo-benzo[d]isothiazol-3-ylamino)-phenyl]-5-methyl-5,6-dihydro-2H-[1,4]oxazin-3-yl}-carbamic acid tert-butyl ester A solution of [5-(3-amino-phenyl)-5-methyl-5,6-dihydro-2H-[1,4]oxazin-3-yl]-carbamic acid tert-butyl ester (51 mg, 0.167 mmol) in THF (2 ml) was stirred at −78° C. under nitrogen. Butyllithium (1.6 M solution in hexanes, 0.26 ml, 0.418 mmol) was added at once. After 10 minutes a solution of 6-bromo-3-chloro-benzo[d]isothiazole (WO 2006091858, page 132; 52 mg, 0.209 mmol) in 0.4 ml THF was added rapidly. After stirring for 30 minutes the mixture was quenched with 5% aq. NH₄Cl and warmed to rt. The mixture was extracted with EtOAc, and the organic phase was washed with brine, dried with Na₂SO₄ and evaporated under reduced pressure. The residue was purified by chromatography on silica gel (hexanes/20-35% EtOAc) to yield the title compound.

HPLC: $Rt_{H4}$=2.143 min; ESIMS: 517, 519 [(M+H)⁺, 1Br];
¹H-NMR (400 MHz, CDCl₃): δ 7.55 (s, 1H), 7.45 (d, 1H, 7.37 (d, 1H), 7.30 (t, 1H), 7.01 (d, 1H), 6.94 (d, 1H), 5.45-5.30 (br, NH), 4.10-3.78 (m, 4H), 1.69 (s, 3H), 1.50 (br s, 9H).

l) [3-(5-Amino-3-methyl-3,6-dihydro-2H-[1,4]oxazin-3-yl)-phenyl]-(6-bromo-benzo[d]isothiazol-3-yl)-amine To a solution of {5-[3-(6-Bromo-benzo[d]isothiazol-3-ylamino)-phenyl]-5-methyl-5,6-dihydro-2H-[1,4]oxazin-3-yl}-carbamic acid tert-butyl ester (36 mg, 0.07 mmol) in DCM (1 ml) was added at +5° C. 1 ml TFA. After 20 minutes the mixture was quenched with water and EtOH and evaporated. The residue was taken up in EtOAc/THF and washed with soda, dried with K₂CO₃ and purified by chromatography on silica gel (DCM/5% MeOH, then DCM/5-10% MeOH containing aq NH3) to yield the title compound.

HPLC: $Rt_{H2}$=3.260 min; ESIMS: 417, 919 [(M+H)⁺, 1Br];
¹H-NMR (600 MHz, DMSO-d₆): δ 9.65 (s, NH), 8.44 (d, 1H), 8.38 (s, 1H), 7.94 (d, 1H), 7.77 (s, 1H, 7.68 (d, 1H), 7.28 (br, NH), 7.25 (t, 1H), 7.04 (d, 1H), 6.70 (br, NH), 4.1-3.9 (m, 2H), 3.68-3.48 (m, 2H), 1.76 (s, 3H).

Example 2

[3-(5-Amino-3-methyl-3,6-dihydro-2H-[1,4]oxazin-3-yl)-phenyl]-(6-bromo-1-methyl-1H-indazol-3-yl)-amine

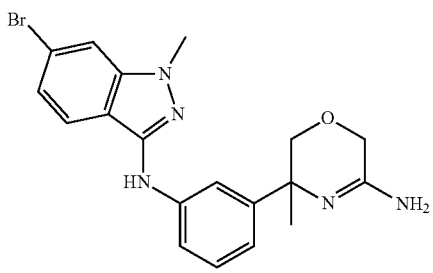 [SMILES: Cn1nc(Nc2cccc(C3(C)COCC(N)=N3)c2)c2ccc(Br)cc21]

a) 5-[3-(6-Bromo-1-methyl-1H-indazol-3-ylamino)-phenyl]-5-methyl-morpholin-3-one A mixture of 5-(3-bromo-phenyl)-5-methyl-morpholin-3-one [Example 1, step f)] (CAS registry 1262858-67-2) (138.5 mg, 0.513 mmol), 6-bromo-1-methyl-1H-indazol-3-ylamine (CAS registry 1214899-85-0) (116 mg, 0.513 mmol), X-phos (78 mg, 0.164 mmol) and K₃PO₄ (218 mg, 1.025 mmol) in toluene (2.5 ml) and water (0.250 ml) was degassed with argon (5 min), then Pd₂(dba)₃ (37.6 mg, 0.041 mmol) was added and the reaction mixture was stirred at 120° C. for 20 h. The reaction mixture was diluted with water, sat. aq. NaHCO₃ soln. and EtOAc. The layers were separated and the aq. layer was twice reextracted with EtOAc. The combined organic layers were washed with brine, dried over Na₂SO₄, filtered and concentrated. The resulting crude product was purified by RP-HPLC (Waters SunFire C18 column, 5 μM, 19×150 mm, gradient 10 to 70% ACN+0.1% TFA) to yield the title compound as a pale yellow powder.

HPLC: $Rt_{H9}$=1.16 min; ESIMS [M+H]⁺=415/417 (1Br).

b) 5-[3-(6-Bromo-1-methyl-1H-indazol-3-ylamino)-phenyl]-5-methyl-morpholine-3-thione To a suspension of 5-[3-(6-bromo-1-methyl-1H-indazol-3-ylamino)-phenyl]-5-methyl-morpholin-3-one (52.6 mg, 0.127 mmol) in toluene (3 ml) was added Lawesson's reagent (51.2 mg, 0.127 mmol) and the reaction mixture was heated at 120° C. for 2 h. The solvent was evaporated and the title compound was purified by FC (cyclohexane:EtOAc 100:0 to 80:20).

HPLC: $Rt_{H9}$=1.31 min; ESIMS [M+H]⁺=431/433 (1Br);
¹H-NMR (400 MHz, CDCl₃): δ 8.32 (br s, 1H), 7.52 (s, 1H), 7.49 (s, 1H), 7.43 (d, 1H), 7.32 (d, 2H), 7.18 (d, 1H), 6.88-6.86 (m, 1H), 6.36 (s, 1H), 4.70-4.55 (m, 2H), 3.94 (s, 3H), 3.88-3.78 (m, 2H), 1.73 (s, 3H).

c) [3-(5-Amino-3-methyl-3,6-dihydro-2H-[1,4]oxazin-3-yl)-phenyl]-(6-bromo-1-methyl-1H-indazol-3-yl)-amine To a suspension of 5-[3-(6-bromo-1-methyl-1H-indazol-3-ylamino)-phenyl]-5-methyl-morpholine-3-thione (21 mg, 0.049 mmol) in MeOH (1.5 ml) were added NH₄OH (0.303 ml of a 25% aq. soln., 273 mg, 1.947 mmol) and tBuOOH (0.101 ml of a 70% aq. soln., 94 mg, 0.730 mmol) and the reaction mixture was allowed to stir at rt for 20 h, quenched with sat. aq. NaHCO₃ soln. and diluted with EtOAc. The layers were separated and the aq. layer was twice reextracted with EtOAc. The combined organic layers were dried over Na₂SO₄, filtered and concentrated to leave the crude title compound that was purified by RP-HPLC (Waters SunFire C18 column, 5 μM, 19×150 mm, gradient 10 to 90% ACN+0.1% TFA).

HPLC: $Rt_{H9}$=0.97 min; ESIMS [M+H]⁺=414/416 (1Br);
¹H-NMR (400 MHz, CDCl₃): δ 7.47 (d, 1H), 7.41 (d, 1H), 7.31 (s, 2H), 7.29-7.23 (m, 4H), 7.13 (dd, 1H), 6.95 (d, 1H), 6.29 (br s, 1H), 4.13 (d, 2H), 3.75-3.67 (m, 1H), 3.67-3.57 (m, 1H), 1.54 (s, 3H).

Example 3 was prepared by a procedure analogous to that used in Example 1.

TABLE 4

| Example | Compound | $^1$H-NMR (δ; CDCl$_3$) | MS [m/z; (M + H)$^+$] |
|---|---|---|---|
| 3 | ![structure] [3-(5-Amino-3-methyl-3,6-dihydro-2H-[1,4]oxazin-3-yl)-phenyl]-benzo[d]isoxazol-3-yl-amine | 7.63 (d, 2H), 7.57-7.46 (m, 3H), 7.35 (t, 1H), 7.26 (t, 2H), 7.06 (d, 1H), 4.18-4.05 (m, 2H), 3.76-3.68 (m, 1H), 3.68-3.60 (m, 1H), 3.11 (br s, 2H), 1.55 (s, 3H) | 323 |

Example 4

5-{2-Fluoro-5-[(furan-2-ylmethyl)-amino]-phenyl}-5-methyl-5,6-dihydro-2H-[1,4]oxazin-3-ylamine

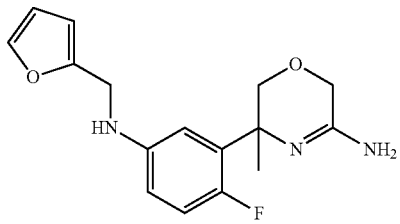 [SMILES: CC1(c2cc(NCc3ccco3)ccc2F)COCC(N)=N1]

a) 5-(5-Bromo-2-fluoro-phenyl)-5-methyl-morpholine-3-thione

To a solution of 5-(5-bromo-2-fluoro-phenyl)-5-methyl-morpholin-3-one (CAS registry 1266784-13-7) (26.0 g, 82 mmol) in THF (520 ml) was added Lawesson's reagent (33.91 g, 82 mmol) and the reaction was heated for 2 h at reflux, then stirred for 14 h at rt. The solvent was evaporated and the title compound was prepurified by FC (toluene). Remaining impurities were removed by washing the toluene fractions with sat. aq. NaHCO$_3$ soln. and water, the combined organic layers were dried over Na$_2$SO$_4$ and concentrated. Crude product was washed with MTBE and used in the next step without further purification.

b) 5-(5-Bromo-2-fluoro-phenyl)-5-methyl-5,6-dihydro-2H-[1,4]oxazin-3-ylamine To a suspension of 5-(5-bromo-2-fluoro-phenyl)-5-methyl-morpholine-3-thione (14.0 g, 46 mmol) in 7N NH$_3$/MeOH (308 ml) was added tBuOOH (72.8 ml of a 70% aq. soln.) and NH$_4$OH (131.6 ml of a 25% aq. soln.). The reaction mixture was stirred over night at rt, quenched with aq. Na$_2$S$_2$O$_3$ soln., concentrated and extracted with EtOAc to give the title compound that was used in the next step without further purification.

c) [5-(5-Bromo-2-fluoro-phenyl)-5-methyl-5,6-dihydro-2H-[1,4]oxazin-3-yl]-carbamic acid tert-butyl ester To a solution of 5-(5-bromo-2-fluoro-phenyl)-5-methyl-5,6-dihydro-2H-[1,4]oxazin-3-ylamine (13.50 g, 47 mmol) in DCM (203 ml) was added Boc$_2$O (13.34 g, 61 mmol) and DIPEA (11.99 ml, 71 mmol) at 0° C. The reaction mixture was allowed to warm to rt over night, then quenched at 10° C. with water. The aq. layer was twice reextracted with EtOAc. The combined org. layers were washed with cold 1N aq. HCl, 2% aq. NaHCO$_3$ soln. and water, dried over Na$_2$SO$_4$ and concentrated to yield the crude title compound that was purified by FC (heptane/EtOAc 9:1).

d) [5-(5-Azido-2-fluoro-phenyl)-5-methyl-5,6-dihydro-2H-[1,4]oxazin-3-yl]-carbamic acid tert-butyl ester A mixture of [5-(5-bromo-2-fluoro-phenyl)-5-methyl-5,6-dihydro-2H-[1,4]oxazin-3-yl]-carbamic acid tert-butyl ester (5.0 g, 12.91 mmol) in EtOH (50 ml) was homogenized in an ultrasound bath for 10 min. To this suspension was added water (22 ml), cyclohexane dimethyldiamine (0.611 ml, 0.551 g, 3.87 mmol), sodium ascorbate (0.512 g, 2.58 mmol), sodium azide (3.36 g, 51.6 mmol) and CuI (0.492 g, 2.58 mmol). The reaction mixture was degassed with Ar and heated for 1 h at 70° C., then cooled to rt, filtered through silica gel and concentrated. The resulting title compound was purified by FC (cyclohexane:EtOAc 100.0 to 80:20).

HPLC: Rt$_{H8}$=0.82 min; ESIMS [M+H]$^+$=350.

e) [5-(5-Amino-2-fluoro-phenyl)-5-methyl-5,6-dihydro-2H-[1,4]oxazin-3-yl]-carbamic acid tert-butyl ester A solution of [5-(5-azido-2-fluoro-phenyl)-5-methyl-5,6-dihydro-2H-[1,4]oxazin-3-yl]-carbamic acid tert-butyl ester (2.18 g, 6.24 mmol) in EtOAc:EtOH 1:1 (150 ml) was hydrogenated over 10% Pd/C (0.21 g) and Lindlar catalyst (0.21 g) with 0.1 bar H$_2$ for 4.5 h at rt. The reaction mixture was filtered through celite and concentrated to leave the title compound that was used in the next step without further purification.

HPLC: Rt$_{H9}$=0.81 min; ESIMS [M+H]$^+$=324.

f) (5-{2-Fluoro-5-[(furan-2-ylmethyl)-amino]-phenyl}-5-methyl-5,6-dihydro-2H-[1,4]oxazin-3-yl)-carbamic acid tert-butyl ester To a solution of [5-(5-amino-2-fluoro-phenyl)-5-methyl-5,6-dihydro-2H-[1,4]oxazin-3-yl]-carbamic acid tert-butyl ester (77.5 mg, 0.240 mmol) and NaOAc (59.0 mg, 0.719 mmol) in MeOH (1 ml) was added 2-furaldehyde (0.020 ml, 23.0 mg, 0.240 mmol). The reaction mixture was degassed with Ar and stirred for 15 min at 100° C. in a microwave. After cooling to 0° C., NaBH₄ (10.02 mg, 0.252 mmol) was added portionwise and stirring was continued at rt for 1 h. The reaction mixture was quenched with water and diluted with EtOAc. The phases were separated and the aq. layer was twice reextracted with EtOAc. The combined organic layers were washed with brine, dried over Na₂SO₄, filtered and concentrated. The resulting title compound was purified by FC (cyclohexane:EtOAc 100:0 to 80:20).

HPLC: $Rt_{H9}$=1.15 min; ESIMS [M+H]⁺=404.

g) 5-{2-Fluoro-5-[(furan-2-ylmethyl)-amino]-phenyl}-5-methyl-5,6-dihydro-2H-[1,4]oxazin-3-ylamine A solution of (5-{2-fluoro-5-[(furan-2-ylmethyl)-amino]-phenyl}-5-methyl-5,6-dihydro-2H-[1,4]oxazin-3-yl)-carbamic acid tert-butyl ester (29 mg, 0.072 mmol) in 4M HCl/dioxane (0.719 ml, 2.88 mmol) was stirred at rt for 2 h, then heated at 50° C. for 2 h. TFA (0.005 ml, 0.072 mmol) was added and stirring at 50° C. was continued for 7 h. The reaction mixture was quenched with water and diluted with EtOAc. The phases were separated and the aq. layer was twice reextracted with EtOAc. The combined organic layers were washed with brine, dried over Na₂SO₄ and concentrated to leave the crude title compound that was purified by RP-HPLC (Waters SunFire C18 column, 5 µM, 19×150 mm, gradient 10 to 90% ACN+0.1% TFA) and obtained as a free base after filtration over an SCX cartridge.

HPLC: $Rt_{H9}$=0.74 min; ESIMS [M+H]⁺=304;
¹H-NMR (400 MHz, CDCl₃): δ 7.36 (s, 1H), 6.96-6.79 (m, 2H), 6.49 (d, 1H), 6.32 (br s, 1H), 4.28 (d, 1H), 4.18-4.07 (m, 1H), 4.04 (s, 1H), 3.98 (d, 1H), 3.83 (s, 2H), 1.54 (s, 3H).

Example 5

5-[5-(4-Bromo-2-chloro-benzylamino)-2-fluoro-phenyl]-5-fluoromethyl-5,6-dihydro-2H-[1,4]oxazin-3-ylamine

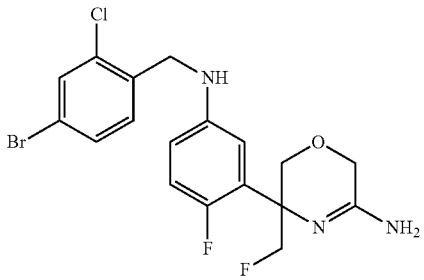 [SMILES: NC1=NC(CF)(c2cc(NCc3ccc(Br)cc3Cl)ccc2F)COC1]

a) 4-Bromo-1-fluoro-2-nitromethyl-benzene

A mixture of 4-bromo-1-fluoro-2-bromomethyl-benzene (5 g, 18.66 mmol) and AgNO₂ (3.45 g, 22.39 mmol) were stirred in 62 ml TBME for 7 h. The dark mixture was filtered over celite, washed with TBME and evaporated. The crude product was purified by chromatography on silica gel (heptane/EtOAc 20/1) to provide the title compound as a yellow oil.

TLC (Hex: EE/9:1): $R_f$=0.3;
HPLC: $Rt_{H4}$=2.449 min;
¹H-NMR (360 MHz, CDCl₃): δ 7.64-7.58 (m, 2H), 7.12 (t, 1H), 5.50 (s, 2H).

b) 2-(5-Bromo-2-fluoro-phenyl)-2-nitro-propane-1,3-diol

A solution of 4-bromo-1-fluoro-2-nitromethyl-benzene (7.75 g, 33.1 mmol), formaldehyde (35%, aqueous) (5.47 ml, 69.5 mmol) and Et₃N (2.3 ml, 16.56 mmol) were stirred in 66 ml dioxane for 3 h. The solution was diluted with brine and extracted with TBME. The organic layer was washed with brine, dried with Na₂SO₄ and evaporated. The crude product was purified by chromatography on silica gel (heptane/EtOAc 3/1) to provide the title compound as a white solid.

TLC (Hex: EE/2:1): $R_f$=0.24;
HPLC: $Rt_{H4}$=2.070 min; ESIMS [M+Na]⁺=316, 318 (1 Br);
¹H-NMR (360 MHz, DMSO): δ 7.65-7.60 (m, 1H), 7.55 (dd, 1H), 7.75 (dd, 1H), 5.50 (s, 2H), 4.20 (br t, 4H).

c) 2-Amino-2-(5-bromo-2-fluoro-phenyl)-propane-1,3-diol

A solution of 2-(5-bromo-2-fluoro-phenyl)-2-nitro-propane-1,3-diol (7 g, 23.8 mmol) in 35 ml AcOH was added dropwise to a mixture of zinc (9.34 g, 143 mmol) in 35 ml AcOH while the temperature did not rise above 40° C. The mixture was stirred for 1 h, filtered over celite and washed with MeOH. The filtrate was evaporated, diluted with water and washed with TBME. The aqueous layer was basified with 2 N NaOH and NH₃ (25%, aqueous), saturated with NaCl and extracted with EtOAc. The organic layer was washed with brine, dried with Na₂SO₄ and evaporated to provide the title compound as an off-white solid.

TLC (EE: MeOH/19:1+1% NH3 (25%, aqueous)): $R_f$=0.38;
HPLC: $Rt_{H2}$=2.332 min; ESIMS [M+H]⁺=246, 266 (1 Br);
¹H-NMR (360 MHz, DMSO): δ 7.82 (dd, 1H), 7.50-7.42 (m, 1H), 7.09 (dd, 1H), 4.71 (br s, 2H), 3.36 (dd, 4H), 2.20 (br s, 2H).

d) N-[1-(5-Bromo-2-fluoro-phenyl)-2-hydroxy-1-hydroxymethyl-ethyl]-2-chloro-acetamide A solution of chloroacetyl chloride (6.39 ml, 80 mmol) in 10 ml ACN was added dropwise to a mixture of 2-amino-2-(5-bromo-2-fluoro-phenyl)-propane-1,3-diol (5.3 g, 20 mmol) and K₂CO₃ (11.1 g, 80 mmol) in 90 ml ACN while the temperature did not rise above 35° C. The mixture was stirred for 2 h. MeOH (40 ml, 99 mmol) were added and after 5 min stirring the mixture was filtered over Celite and washed with MeOH. The filtrate was acidified with citric acid solution (10%, aqueous) (pH 4-5) and partly evaporated. The remaining aqueous layer was extracted with EtOAc. The organic layer was washed with NaHCO₃ solution (10%, aqueous) and brine, dried with Na₂SO₄ and evaporated to provide the title compound as an off-white solid.

TLC (Hex: EE/1:1): $R_f$=0.23;
HPLC: $Rt_{H4}$=1.966 min; ESIMS [M+H]⁺=340, 342 (1 Br);
¹H-NMR (360 MHz, DMSO): δ 8.19 (s, 1H), 7.47 (dd, 1H), 7.10 (dd, 1H), 5.00 (t, 2H), 4.19 (s, 2H), 3.98-3.81 (m, 4H).

e) 5-(5-Bromo-2-fluoro-phenyl)-5-hydroxymethyl-morpholin-3-one

A mixture of N-[1-(5-bromo-2-fluoro-phenyl)-2-hydroxy-1-hydroxymethyl-ethyl]-2-chloro-acetamide (6.34 g, 18.62 mmol) and potassium tert.-butoxide (2.09 g, 18.62 mmol) in 62 ml tBuOH was refluxed for 30 min. 19 ml 1 N HCl and water were added and the aqueous layer was extracted with EtOAc. The organic layer was washed with brine, dried with MgSO$_4$ and evaporated. The crude product was recrystallized in Hex/EtOAc to provide the title compound as an off-white solid.

TLC (Hex: EE/1:2): R$_f$=0.25;
HPLC: Rt$_{H4}$=1.885 min; ESIMS [M+H]$^+$=304, 306 (1 Br);
$^1$H-NMR (360 MHz, DMSO): δ 8.49 (s, 1H), 7.62-7.56 (m, 2H), 7.21 (dd, 1H), 5.25 (t, 1H), 4.15 (d, 1H), 4.02 (s, 2H), 3.91 (d, 1H), 3.79-3.62 (m, 2H).

f) 5-(5-Bromo-2-fluoro-phenyl)-5-fluoromethyl-morpholin-3-one

To a solution of 5-(5-bromo-2-fluoro-phenyl)-5-hydroxymethyl-morpholin-3-one (1.6 g, 5.26 mmol) in 30 ml THF was added dropwise diethylaminosulfur trifluoride (0.97 ml, 7.34 mmol) and stirred for 2 h. The colorless solution was slowly added to an ice cooled Na$_2$CO$_3$ solution (10%, aqueous) and extracted with TBME. The organic layer was washed with brine, dried with MgSO$_4$ and evaporated. The crude product was purified by chromatography on silica gel (heptane/EtOAc 3/1) to provide the title compound as a slightly yellow solid.

TLC (Hex: EE/1:1): R$_f$=0.43;
HPLC: Rt$_{H4}$=2.136 min; ESIMS [M+H]$^+$=306, 308 (1 Br);
$^1$H-NMR (360 MHz, CDCl$_3$): δ 7.50-7.40 (m, 2H), 6.95 (dd, 1H), 6.55 (s, 1H), 4.86-4.58 (m, 2H), 4.22-4.11 (m, 2H), 4.07-3.98 (m, 2H).

g) 5-(5-Bromo-2-fluoro-phenyl)-5-fluoromethyl-morpholine-3-thione

A mixture of 7.34 g (22.65 mmol) 5-(5-bromo-2-fluoro-phenyl)-5-fluoromethyl-morpholin-3-one and 5.19 g (12.46 mmol) Lawesson's reagent in 73 ml of THF was refluxed for 1 h. The mixture was concentrated and crystallized from DCM/hexane and recrystallized from EtOH to yield the desired product as colorless crystals.

HPLC: Rt$_{H5}$=2.410 min; ESIMS [M+H]$^+$=322, 324 (1Br);
$^1$H-NMR (360 MHz, DMSO-d6): δ 8.46 (br s, 1H), 7.57 (ddd, 1H), 7.49 (dd, 1H), 7.08 (dd, 1H), 5.01 (d, 1H), 4.88 (d, 1H), 4.85 (d, 1H), 4.72 (d, 1H), 4.69 (d, 1H), 4.59 (d, 1H), 4.21 (d, 1H), 4.12 (d, 1H).

h) 5-(5-Bromo-2-fluoro-phenyl)-5-fluoromethyl-5,6-dihydro-2H-[1,4]oxazin-3-ylamine A solution of 6.14 g (18.05 mmol) 5-(5-bromo-2-fluoro-phenyl)-5-fluoromethyl-morpholine-3-thione in 77 ml 7M NH3/MeOH was stirred at rt for 15 h. The mixture was evaporated and purified chromatographed on silica gel (DCM/1-5% MeOH followed by DCM/MeOH/aqueous NH3 95:4.5:0.5) to give the desired product as yellowish resin.

TLC (DCM/MeOH 9:1 containing 0.5% aq NH3 (25%)): R$_f$=0.4;
HPLC: Rt$_{H5}$=1.913 min; ESIMS [M+H]$^+$=305, 307 (1Br);
$^1$H-NMR (360 MHz, DMSO-d6): δ 8.0-7.4 (br 2H), 7.77 (dd, 1H), 7.64 (ddd, 1H), 7.27 (dd, 1H), 4.83-4.58 (m, 12H), 4.31 (s, 2H), 4.11 (d, 1H), 3.96 (d, 1H).

i) [5-(5-Bromo-2-fluoro-phenyl)-5-fluoromethyl-5,6-dihydro-2H-[1,4]oxazin-3-yl]-carbamic acid tert-butyl ester To an ice-cold solution of 1.30 g (4.26 mmol) 5-(5-bromo-2-fluoro-phenyl)-5-fluoromethyl-5,6-dihydro-2H-[1,4]oxazin-3-ylamine in 21 ml THF were added 1.40 g (6.39 mmol) Boc2O and 1.26 ml (7.24 mmol) DIPEA. The mixture was stirred for 4 h at rt. Then the mixture was diluted with TBME and washed with 5% aqueous NaHCO3. The organic phase was dried with MgSO4.H2O, filtered and concentrated. Purification by chromatography on silica gel (hexane/15% EtOAc) gave the desired product as a pale yellow resin.

HPLC: Rt$_{H1}$=2.418 min; ESIMS [M+H]$^+$=405, 407 (1Br);
$^1$H-NMR (360 MHz, CDCl$_3$, broad signals due to rotamers): δ 7.72 (m, 1H), 7.44 (m, 1H), 6.98 (m, 1H), 4.8-3.9 (m, 6H), 1.53 (br s, 9H).

j) [5-(5-Amino-2-fluoro-phenyl)-5-fluoromethyl-5,6-dihydro-2H-[1,4]oxazin-3-yl]-carbamic acid tert-butyl ester To a solution of 0.69 g (1.703 mmol) [5-(5-bromo-2-fluoro-phenyl)-5-fluoromethyl-5,6-dihydro-2H-[1,4]oxazin-3-yl]-carbamic acid tert-butyl ester and 72.7 mg (0.511 mmol) trans-N,N'-dimethylcyclohexane-1,2-diamine in 7.5 ml EtOH was added a solution of 443 mg (6.81 mmol) sodium azide and 67.5 g (0.341 mmol) sodium-ascorbate in 3 ml water. The mixture was degassed and brought under nitrogen atmosphere. CuI (64.9 mg, 0.341 mmol) was added and the mixture was heated at 70° C. The initially formed suspension turned into a homogeneous blue solution. The mixture was cooled to rt, diluted with water and TBME. The organic phase was washed with brine and dried with MgSO4.H2O. The crude product, consisting of a mixture of aryl azide and aniline, was dissolved in 3 ml EtOH and 3 ml THF and treated with 20 mg 10% Pd—C and stirred under an atmosphere of hydrogen until all azide had been consumed. The mixture was diluted with DCM and filtered over celite. The product was purified by chromatography on silica gel (heptane/30% EtOAc) to give the desired product as colorless foam.

TLC (Hex: EE/1:1): R$_f$=0.38;
HPLC: Rt$_{H5}$=1.895 min; ESIMS [M+H]$^+$=342;
$^1$H-NMR (360 MHz, DMSO, broad signals due to rotamers): δ 9.79 (s, 1H), 6.82 (br t, 1H), 6.70-6.62 (m, 1H), 6.51-6.43 (m, 1H), 4.92 (s, 2H), 4.70-4.38 (m, 4H), 3.95-3.81 (m, 2H), 1.43 (s, 9H).

k) {5-[5-(4-Bromo-2-chloro-benzylamino)-2-fluoro-phenyl]-5-fluoromethyl-5,6-dihydro-2H-[1,4]oxazin-3-yl}-carbamic acid tert-butyl ester A mixture of [5-(5-amino-2-fluoro-phenyl)-5-fluoromethyl-5,6-dihydro-2H-[1,4]oxazin-3-yl]-carbamic acid tert-butyl ester (60 mg, 0.176 mmol) and 4-bromo-2-chloro-benzaldehyde (39 mg, 0.176 mmol) in 2 ml DCM were stirred overnight in the presence of 42 mg anhydrous MgSO$_4$. An NMR probe showed incomplete conversion. 4-Bromo-2-chloro-benzaldehyde (39 mg, 0.176 mmol) was added and stirring was continued for 16 h. The mixture was diluted with toluene and filtered. A few drops of acetic acid were added and the mixture was evaporated.

The residue was dissolved in toluene and evaporated (2×). The residue was dissolved in 1.5 ml EtOH and treated with NaBH$_4$ (13.3 mg, 0.352 mmol) and stirred for 5 h. The rm was partitioned between water and EtOAc. The organic layer was dried with Na$_2$SO$_4$ and evaporated. The product was purified with column chromatography on silica gel [Hex/10-15% (5% MeOH in EtOAc)].

TLC [Hex/(EE:MeOH 95:5) 6/1]: R$_f$=0.31;
HPLC: Rt$_{H3}$=3.209 min; ESIMS [M+H]$^+$=544, 546 (1 Br).

l) 5-[5-(4-Bromo-2-chloro-benzylamino)-2-fluoro-phenyl]-5-fluoromethyl-5,6-dihydro-2H-[1,4]oxazin-3-ylamine {5-[5-(4-Bromo-2-chloro-benzylamino)-2-fluoro-phenyl]-5-fluoromethyl-5,6-dihydro-2H-[1,4]oxazin-3-yl}-carbamic acid tert-butyl ester (82 mg, 0.151 mmol) were suspended in 1.1 ml HCl/Dioxane (4M). A few drops HCl/MeOH (3M) were added and the mixture was stirred at 50° C. for 2 h. The mixture was evaporated, taken up in 10% aq soda, extracted with DCM and dried with $Na_2SO_4$. The title compound was purified via chromatography on silica gel [DCM/1-5%(MeOH/DCM 10:90)]. The product was dissolved in $Et_2O$ and precipitated as its hydrochloride salt by adding 1N HCl/$Et_2O$.

HPLC: $Rt_{H2}$=3.232 min; ESIMS [M+H]$^+$=444, 446 (1 Br);
$^1$H-NMR (600 MHz, DMSO-d6): δ 10.76 (m, 1H), 9.38 (d, 1H), 8.63 (d, 1H), 7.74 (s, 1H), 7.54 (d, 1H), 7.33 (d, 1H), 7.02 (dd, 1H), 6.59 (m, 1H), 6.49 (m, 1H), 4.91-4.80 (m, 2H), 4.60 (d, 1H), 4.50 (d, 1H), 4.25 (s, 2H), 4.08 (s, 2H).

Example 6

5-{5-[(4-Bromo-furan-2-ylmethyl)-amino]-2-fluoro-phenyl}-5-difluoromethyl-5,6-dihydro-2H-[1,4]oxazin-3-ylamine

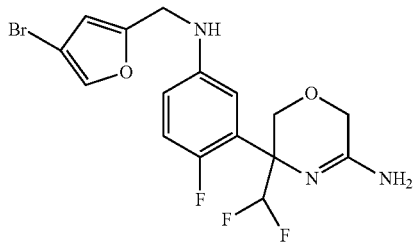 [SMILES: NC1=NC(c2cc(NCc3cc(Br)co3)ccc2F)(C(F)F)COC1]

The compound was prepared by a procedure analogous to that described in example 5 [steps k) to l)] using [5-(5-amino-2-fluoro-phenyl)-5-difluoromethyl-5,6-dihydro-2H-[1,4]oxazin-3-yl]-carbamic acid tert-butyl ester (CAS 1262859-07-3) and 4-bromo-furan-2-carbaldehyde (CAS 21921-76-6).
The title compound was obtained as a yellow foam.
TLC (DCM/MeOH/aq NH3 95:5:0.5): $R_f$=0.29;
HPLC: $Rt_{H3}$=2.888 min; ESIMS [M+H]$^+$=418, 420 (1Br);
$^1$H-NMR (600 MHz, DMSO-d6): δ 11.10 (s, 1H), 9.70 (s, 1H), 9.00 (s, 1H), 7.82 (s, 1H), 7.06 (dd, 1H), 6.75 (m, 1H), 6.70 (m, 1H), 6.66 (t, J=40 Hz, 1H), 6.57 (s, 1H), 4.68 (d, 1H), 4.55 (d, 1H), 4.33 (d, 1H), 4.27 (s, 2H), 4.05 (d, 1H).

Example 7

3-((R)-5-Amino-3-difluoromethyl-3,6-dihydro-2H-[1,4]oxazin-3-yl)-4-fluoro-phenyl]-(7-chloropyrido[3,2-d]pyrimidin-4-yl)-amine di-hydrochloride

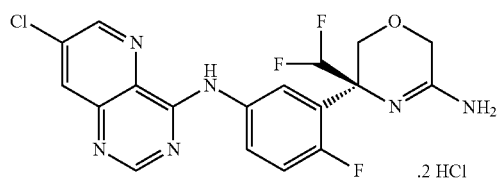 [SMILES: NC1=N[C@@](c2cc(Nc3ncnc4cc(Cl)cnc34)ccc2F)(C(F)F)COC1]

To a solution of [(R)-5-(5-Amino-2-fluoro-phenyl)-5-difluoromethyl-5,6-dihydro-2H-[1,4]oxazin-3-yl]-carbamic acid tert-butyl ester (CAS registry 1262859-09-5) (98 mg, 0.273 mmol) and 4,7-dichloro-pyrido[3,2-d]pyrimidine (CAS registry 917757-12-1) (61 mg, 0.30 mmol) in tBuOH (2 ml) was added 0.08 mL 4N HCl in dioxane and the reaction mixture was heated in a microwave oven for 1 h at 100° C. The reaction mixture was basified with saturated $NaHCO_3$ solution and the product was extracted with EtOAc. Combined extracts were washed with brine, dried over $MgSO_4$, filtered and concentrated. The crude product was dissolved in THF, acidified with 1N HCl in $Et_2O$, and concentrated. The remaining yellow solid was two times triturated with $Et_2O$ and subsequently dried to afford the title compound as light yellow amorphous solid.

TLC (EtOAc/MeOH 9:1): Rf=0.43;
UPLC: $Rt_{H6}$=0.770 min; ESIMS: 423 [(M+H)$^+$];
$^1$H-NMR (600 MHz, DMSO-d6): δ 9.92 (s, 1H), 9.18 (s, 1H), 9.03 (s, 1H), 8.81 (s, 1H), 8.51 (d, 1H), 8.20 (m, 2H), 7.46 (dd, 1H), 6.79 (t, 1H), 4.72 (m, 2H), 4.32 (d, 1H), 4.24 (d, 1H).

Example 8

[3-((R)-5-Amino-3-difluoromethyl-3,6-dihydro-2H-[1,4]oxazin-3-yl)-4-fluoro-phenyl]-(3-bromo-[1,7]naphthyridin-8-yl)-amine

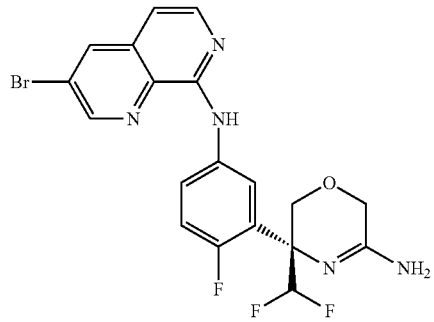 [SMILES: NC1=N[C@@](c2cc(Nc3nccc4cc(Br)cnc34)ccc2F)(C(F)F)COC1]

[(R)-5-(5-Amino-2-fluoro-phenyl)-5-difluoromethyl-5,6-dihydro-2H-[1,4]oxazin-3-yl]carbamic acid tert-butyl ester (CAS registry 1262859-09-5) (250 mg, 0.696 mmol) and 3-bromo-8-chloro-[1,7]naphthyridine [Heteroaryl 1] (186 mg, 0.765 mmol) were dissolved in tert-Butanol (4 ml) in a microwave vial and HCl (0.174 ml of a 4M solution in dioxane) was added. The vial was sealed and heated to 100° C. for 1 h. The reaction mixture was cooled to rt and added to a saturated $NaHCO_3$ solution (20 ml) and stirred at rt for 10 min.

The solution was extracted with DCM (2×30 ml). The combined organic layer was washed with $NaHCO_3$ solution and brine, treated with $MgSO_4$, filtered and to give the desired product.

HPLC: $Rt_{H9}$=0.90 min; ESIMS [M+H]$^+$=465.9/467.9 (1 Br);
$^1$H-NMR (400 MHz, CDCl$_3$): δ 8.90 (s, 1H), 8.64 (m, 1H), 8.27 (m, 1H), 8.08 (d, 1H), 7.90 (dd, 1H), 7.10 (dd, 1H), 6.82

(d, 1H), 6.34-6.06 (t, 1H), 4.35 (dd, 1H), 4.18 (d, 1H), 4.07 (d, 1H), 3.96 (d, 1H).

$^{19}$F-NMR (376 MHz, CDCl$_3$): δ −119.6 (s), (−126.53)-(−129.20) (dq).

Example 9

8-[3-((R)-5-Amino-3-difluoromethyl-3,6-dihydro-2H-[1,4]oxazin-3-yl)-4-fluoro-phenylamino]-[1,7]naphthyridine-3-carbonitrile

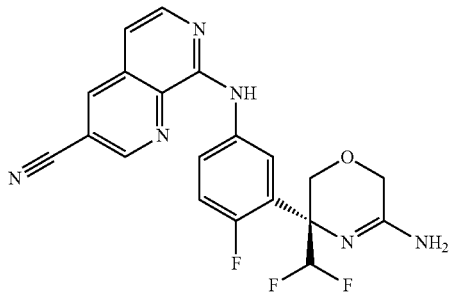 [SMILES: N#Cc1cnc2c(Nc3ccc(F)c([C@]4(C(F)F)COCC(N)=N4)c3)nccc2c1]

[3-((R)-5-Amino-3-difluoromethyl-3,6-dihydro-2H-[1,4]oxazin-3-yl)-4-fluoro-phenyl]-(3-bromo-[1,7]naphthyridin-8-yl)-amine (150 mg, 0.32 mmol), Zn powder (0.842 mg, 0.013 mmol), Zn(CN)$_2$ (22.7 mg, 0.193 mmol), Zn(OAc)$_2$ (2.36 mg 0.013 mmol), 1,1'-Bis-(diphenylphosphino)-ferrocene (0.54 mg, 0.001 mmol) and Tris(dibenzylideneacetone)-dipalladium (0) (0.29 mg 0.0003 mmol) were dissolved in DMF (4 ml) and water (0.04 ml) and heated under inert conditions to 95° C. for 2 h and then allowed to cool to rt. The reaction was quenched with water (10 ml) and NH$_3$ (25%, 1 ml) and extracted with EtOAc (25 ml). The aq phase was extracted another 3× with EtOAc. The combined organic layer was washed with NaHCO$_3$ solution and brine, treated with MgSO$_4$ and filtered. The filtrated was concentrated and purified by column chromatography (silica gel; hexane/0-15% EtOAc) to give the desired product as a yellow solid.

HPLC: Rt$_{H9}$=0.78 min; ESIMS [M+H]$^+$=413.0;

$^1$H-NMR (400 MHz, CDCl$_3$): δ 8.86 (s, 1H), 8.63 (m, 1H), 8.24 (m, 1H), 8.05 (d, 1H), 7.93 (dd, 1H), 7.09 (dd, 1H), 6.85 (d, 1H), 6.35-6.07 (t, 1H), 4.32 (dd, 1H), 4.18 (d, 1H), 4.07 (d, 1H), 4.00 (d, 1H).

$^{19}$F-NMR (376 MHz, CDCl$_3$): δ −118.9 (s), (−127.35)-(−129.18) (dq).

Example 10

[3-((R)-5-Amino-3-difluoromethyl-3,6-dihydro-2H-[1,4]oxazin-3-yl)-4-fluoro-phenyl]-[3-(2-methoxy-ethoxy)-[1,7]naphthyridin-8-yl]-amine

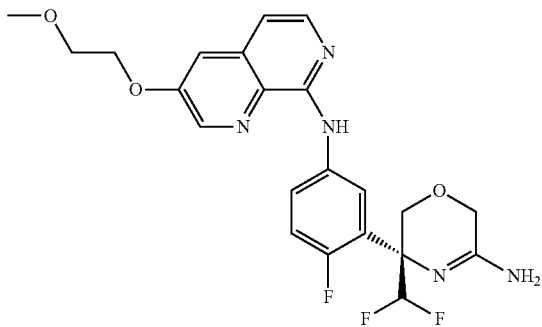 [SMILES: COCCOc1cnc2c(Nc3ccc(F)c([C@]4(C(F)F)COCC(N)=N4)c3)nccc2c1]

Example 11

[3-((R)-5-Amino-3-difluoromethyl-3,6-dihydro-2H-[1,4]oxazin-3-yl)-4-fluoro-phenyl]3-(2-chloro-ethoxy)-[1,7]naphthyridin-8-yl]-amine

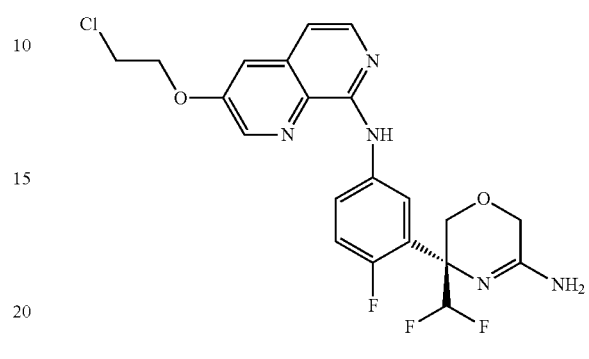

3-(2-Methoxy-ethoxy)-7H-[1,7]naphthyridin-8-one [Heteroaryl 2] (330 mg, 1.498 mmol) was suspended in toluene (15 ml). DIPEA (1.309 ml, 7.49 mmol) and POCl$_3$ (0.419 ml, 4.50 mmol) were added and the reaction mixture was heated to 125° C. for 48 h.

The reaction mixture was cooled to rt and partitioned between water (10 ml) and EtOAc (50 ml). The phases were separated and the aq phase was extracted twice with EtOAc (25 ml). The combined organic layer was washed with NaHCO$_3$ solution and brine, treated with MgSO$_4$, filtered and concentrated. 66 mg of the beige solid thus obtained were dissolved in tBuOH (4 ml) in a microwave vial, [(R)-5-(5-amino-2-fluoro-phenyl)-5-difluoromethyl-5,6-dihydro-2H-[1,4]oxazin-3-yl]-carbamic acid tert-butyl ester (CAS registry 1262859-09-5) (100 mg, 0.278 mmol) and HCl (4 M in Dioxane, 69.6 µL, 0.278 mmol) were added. The microwave vial was sealed and heated to 100° C. for 1 h. The reaction mixture was cooled to rt and added to a saturated NaHCO$_3$ solution (20 ml) and stirred at rt for 10 min. The solution was extracted twice with EtOAc (30 ml). The combined organic layer was washed with NaHCO$_3$ solution and brine, treated with MgSO$_4$, filtered, concentrated, separated and purified by chromatography (silica gel; DCM/MeOH 3%):

[3-((R)-5-Amino-3-difluoromethyl-3,6-dihydro-2H-[1,4]oxazin-3-yl)-4-fluoro-phenyl]-[3-(2-methoxy-ethoxy)-[1,7]naphthyridin-8-yl]-amine (yellow resin)

HPLC: Rt$_{H9}$=0.71 min; ESIMS [M+H]$^+$=462.3;

$^1$H-NMR (400 MHz, CDCl$_3$): δ 8.86 (s, 1H), 8.40 (d, 1H), 8.21 (m, 1H), 7.97 (d, 1H), 7.90 (dd, 1H), 7.15 (d, 1H), 7.07 (dd, 1H), 6.82 (d, 1H), 6.36-6.08 (t, 1H), 4.32 (dd, 1H), 4.23-4.05 (m, 3H), 3.96 (d, 1H), 3.82 (m, 2H), 3.48 (s, 3H).

$^{19}$F-NMR (376 MHz, CDCl$_3$): δ −120.37 (s), (−126.49)-(−128.95) (dq).

[3-((R)-5-Amino-3-difluoromethyl-3,6-dihydro-2H-[1,4]oxazin-3-yl)-4-fluoro-phenyl]-[3-(2-chloro-ethoxy)-[1,7]naphthyridin-8-yl]-amine (off white solid)

HPLC: Rt$_{H9}$=0.82 min; ESIMS [M+H]$^+$=466.2/468.2 (1Cl);

$^1$H-NMR (400 MHz, CDCl$_3$): δ 8.90 (s, 1H), 8.44 (d, 1H), 8.26 (m, 1H), 8.02 (m, 1H), 7.90 (m, 1H), 7.17 (m, 1H), 7.09 (m, 1H), 6.86 (m, 1H), 6.36-6.08 (t, 1H), 4.36-3.96 (m, 4H), 3.90 (t, 2H), 3.64 (m, 2H).

$^{19}$F-NMR (376 MHz, CDCl$_3$): δ −120.29 (s), (−126.50)-(−128.82) (dq).

Examples 12 to 22

The compounds listed in Table 5 were prepared by procedures analogous to those used for Examples 7 and 8, applying reaction times of 1 h and up to 6 days and purification by column chromatography or preparative TLC. Example 20 was prepared using Heteroaryl 4.

TABLE 5

| Example | Compound | $^1$H-NMR (δ; CDCl$_3$ or DMSO-d6) | MS [m/z; (M + H)$^+$] |
|---|---|---|---|
| 12 | [3-((R)-5-Amino-3-difluoromethyl-3,6-dihydro-2H-[1,4]oxazin-3-yl)-4-fluoro-phenyl]-(2-methyl-imidazo[1,2-a]pyrazin-yl)-amine | 9.33 (s, 1H), 8.29 (m, 1H), 7.93 (m, 1H), 7.91 (m, 1H), 7.87 (d, 1H), 7.70 (s, 1H), 7.33 (d, 1H), 6.09 (t, 1H), 4.08 (d, 1H), 4.01 (d, 1H), 3.90 (d, 1H), 3.82 (d, 1H), 2.38 (s, 3H). | 391 |
| 13 | [3-((R)-5-Amino-3-difluoromethyl-3,6-dihydro-2H-[1,4]oxazin-3-yl)-4-fluoro-phenyl]-imidazo[1,2-a]pyrazin-8-yl-amine | 8.20-8.13 (m, 2H), 8.29 (m, 1H), 7.83 (m, 1H), 7.53 (3, 1H), 7.40 (d, 1H), 7.07 (m, 1H), 6.19 (t, 1H), 4.30 (d, 1H), 4.16 (d, 1H), 4.06 (d, 1H), 3.96 (d, 1H). | 377 |
| 14 | [3-((R)-5-Amino-3-difluoromethyl-3,6-dihydro-2H-[1,4]oxazin-3-yl)-4-fluoro-phenyl]-(3-bromo-imidazo[1,2-a]pyrazin-8-yl)-amine | 8.18 (m, 1H), 8.02 (s, 1H), 7.84 (m, 1H), 7.50 (m, 3H), 7.07 (m, 1H), 6.18 (t, 1H), 4.30 (d, 1H), 4.16 (d, 1H), 4.04 (d, 1H), 3.96 (d, 1H). | 455, 457 |

TABLE 5-continued

| Example | Compound | ¹H-NMR (δ; CDCl₃ or DMSO-d6) | MS [m/z; (M + H)⁺] |
|---|---|---|---|
| 15 | 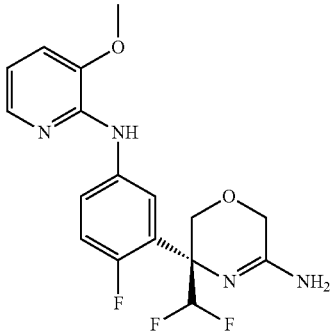<br>(R)-5-Difluoromethyl-5-[2-fluoro-5-(3-methoxy-pyridin-2-ylamino)-phenyl]-5,6-dihydro-2H-[1,4]oxazin-3-ylamine | 8.07 (m, 1H), 7.75 (dd, 1H), 7.62 (dd, 1H), 7.03 (m, 1H), 6.91 (dd, 1H), 6.66 (dd, 1H), 6.19 (t, 1H), 4.31 (dd, 1H), 4.16 (d, 1H), 4.04 (d, 1H), 3.93 (d, 1H), 3.82 (s, 3H). | 367 |
| 16 | 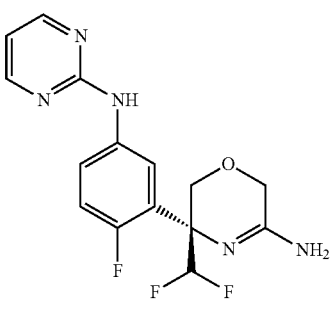<br>(R)-5-Difluoromethyl-5-[2-fluoro-5-(pyrimidin-2-ylamino)-phenyl]-5,6-dihydro-2H-[1,4]oxazin-3-ylamine | 8.39 (d, 2H), 8.14 (s, 1H), 7.82 (m, 1H), 7.03 (m, 1H), 7.59 (dd, 1H), 7.01 (dd, 1H), 6.61 (t, 1H), 6.21 (t, 1H), 4.24 (dd, 1H), 4.14 (d, 1H), 3.99 (d, 1H), 3.92 (d, 1H). | 338 |
| 17 | 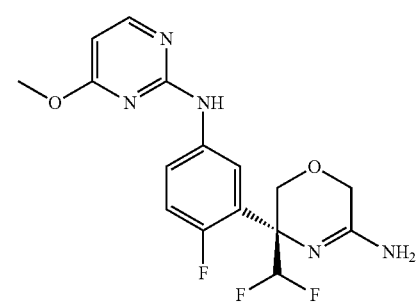<br>(R)-5-Difluoromethyl-5-[2-fluoro-5-(4-methoxy-pyrimidin-2-ylamino)-phenyl]-5,6-dihydro-2H-[1,4]oxazin-3-ylamine | 8.09 (d, 1H), 7.81 (m, 1H), 7.65 (m, 1H), 7.03 (m, 1H), 7.41 (s, 1H), 7.02 (dd, 1H), 6.31-6.03 (m, 2H), 4.30 (dd, 1H), 4.15 (d, 1H), 4.03 (d, 1H), 3.92 (m, 4H). | 368 |

TABLE 5-continued

| Example | Compound | ¹H-NMR (δ; CDCl₃ or DMSO-d6) | MS [m/z; (M + H)⁺] |
|---|---|---|---|
| 18 | 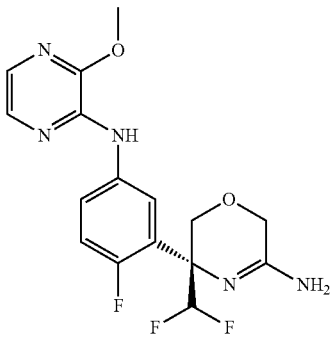<br>(R)-5-Difluoromethyl-5-[2-fluoro-5-(3-methoxy-pyrazin-2-ylamino)-phenyl]-5,6-dihydro-2H-[1,4]oxazin-3-ylamine | 8.06 (m, 1H), 7.68 (dd, 1H), 7.65 (d, 1H), 7.46 (d, 1H), 7.18 (s, 1H), 7.06 (dd, 1H), 6.21 (t, 1H), 4.34 (dd, 1H), 4.24 (d, 1H), 4.12 (d, 1H), 4.03 (s, 3H), 3.96 (d, 1H). | 368 |
| 19 | 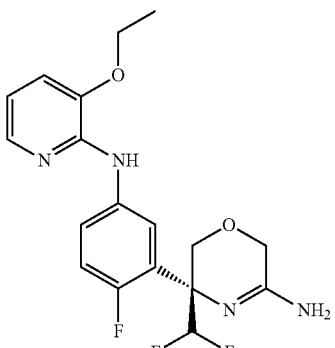<br>(R)-5-Difluoromethyl-5-[5-(3-ethoxy-pyridin-2-ylamino)-2-fluoro-phenyl]-5,6-dihydro-2H-[1,4]oxazin-3-ylamine | 8.08 (m, 1H), 7.75 (d, 1H), 7.60 (dd, 1H), 7.03 (m, 2H), 6.90 (d, 1H), 6.65 (dd, 1H), 6.19 (t, 1H), 4.33 (dd, 1H), 4.14 (d, 1H), 4.07 (m, 3H), 3.89 (d, 1H), 1.45 (t, 3H). | 381 |
| 20 | 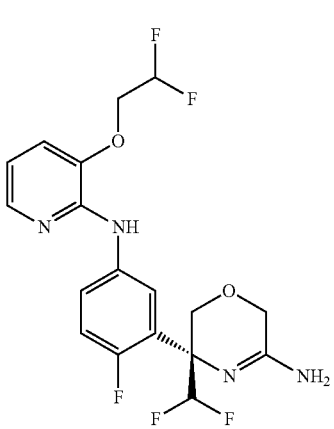<br>(R)-5-{5-[3-(2,2-Difluoro-ethoxy)-pyridin-2-ylamino]-2-fluoro-phenyl}-5-difluoromethyl-5,6-dihydro-2H-[1,4]oxazin-3-ylamine | 8.06 (m, 1H), 7.80 (d, 1H), 7.04 (dd, 1H), 7.03 (m, 2H), 6.93 (s, 1H), 6.88 (d, 1H), 6.63 (d, 1H), 6.18 (t, 1H), 5.99 (tt, 1H), 4.33 (dd, 1H), 4.16 (m, 3H), 4.03 (d, 1H), 3.90 (d, 1H). | 417 |

TABLE 5-continued

| Example | Compound | ¹H-NMR (δ; CDCl₃ or DMSO-d6) | MS [m/z; (M + H)⁺] |
|---|---|---|---|
| 21 | (R)-5-Difluoromethyl-5-[2-fluoro-5-(5-methoxy-pyrimidin-4-ylamino)-phenyl]-5,6-dihydro-2H-[1,4]oxazin-3-ylamine | 8.89 (s, 1H), 8.20-8.01 (m, 3H), 7.71 (m, 1H), 7.09 (m, 1H), 6.11 (t, 1H), 6.07 (br s, 2H), 4.16-3.35 (m, 7H). | 368 |
| 22 | (R)-5-[5-(3-(Difluoromethoxy-pyridin-2-ylamino)-2-fluoro-phenyl]-5-dufluoromethyl-5,6-dihydro-2H-[1,4]oxazin-3-ylamine | 8.02 (m, 1H), 7.97 (m, 1H), 7.62 (dd, 1H), 7.31 (d, 1H), 7.05 (dd, 1H), 6.88 (m, 1H), 6.71 (dd, 1H), 6.55 (t, 1H), 6.18 (t, 1H), 4.33 (dd, 1H), 4.17 (d, 3H), 4.05 (d, 1H), 3.91 (m, 1H). | 403 |

Example 23

[3-((3R,6R)-5-Amino-3,6-dimethyl-6-trifluoromethyl-3,6-dihydro-2H-[1,4]oxazin-3-yl)-4-fluoro-phenyl]-(7-chloro-pyrido[3,2-d]pyrimidin-4-yl)-amine di-hydrochloride

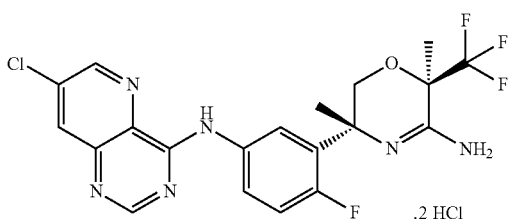 [SMILES: C[C@@]1(c2cc(Nc3ncnc4cc(Cl)cnc34)ccc2F)CO[C@@](C)(C(F)(F)F)C(N)=N1]

To a solution of [(2R,5R)-5-(5-amino-2-fluoro-phenyl)-2,5-dimethyl-2-trifluoromethyl-5,6-dihydro-2H-[1,4]oxazin-3-yl]-carbamic acid tert-butyl ester (CAS registry 1262859-70-0) (138 mg, 0.34 mmol) and 4,7-dichloro-pyrido[3,2-d]pyrimidine (CAS registry 917757-12-1) (75 mg, 0.374 mmol) in tBuOH (2 ml) was added 0.1 ml 4N HCl in dioxane and the reaction mixture was heated in a microwave oven for 1 h at 100° C. The reaction mixture was basified with saturated NaHCO₃ solution and the product was extracted with EtOAc. Combined extracts were washed with brine, dried over MgSO₄, filtered and concentrated. The crude product was dissolved in THF, acidified with 1N HCl in Et₂O, and concentrated. The remaining yellow solid was two times triturated with Et₂O and subsequently dried to afford the title compound as light yellow amorphous solid.

TLC (EtOAc/MeOH 9:1): Rf=0.57;

UPLC: Rt$_{H6}$=1.122 min; ESIMS: 469 [(M+H)⁺];

¹H-NMR (600 MHz, DMSO-d6): δ 9.76 (s, 2H), 9.03 (s, 1H), 8.79 (s, 1H), 8.49 (d, 1H), 8.15 (m, 1H), 8.06 (m, 1H), 7.39 (dd, 1H), 4.42 (d, 1H), 4.16 (d, 1H), 1.79 (s, 3H), 1.71 (s, 3H).

Examples 24 to 25

The compounds listed in Table 6 were prepared by procedures analogous to those used for Examples 7, 8 and 23, applying reaction times of 1 h and up to 6 days and purification by column chromatography or preparative TLC. Example 24 was prepared using Heteroaryl 3.

TABLE 6

| Example | Compound | ¹H-NMR (δ; CDCl₃ or DMSO-d6) | MS [m/z; (M + H)⁺] |
|---|---|---|---|
| 24 | [3-((3R,6R)-5-Amino-3,6-dimethyl-6-trifluoromethyl-3,6-dihydro-2H-[1,4]oxazin-3-yl)-4-fluoro-phenyl]-(7-trifluoromethyl-pyrido[3,2-d]pyrimidin-4-yl)-amine hydrochloride | 11.98 (s, 2H), 11.21 (s, 1H), 9.74 (s, 1H), 9.27 (s, 1H), 8.83 (s, 1H), 8.73 (s, 1H), 8.17 (d, 1H), 8.09 (d, 1H), 7.39 (t, 1H), 4.39 (d, 1H), 4.09 (d, 1H), 1.80 (s, 3H), 1.71 (s, 3H). | 503 |
| 25 | (2R,5R)-5-[2-Fluoro-5-(3-methoxy-pyridin-2-ylamino)-phenyl]-2,5-dimethyl-2-trifluoromethyl-5,6-dihydro-2H-[1,4]oxazin-3-ylamine | 7.80-7.75 (m, 2H), 7.57 (dd, 1H), 7.01-6.93 (m, 3H), 6.67 (dd, 1H), 4.06 (d, 1H), 3.96 (d, 1H), 3.89 (s, 3H), 1.56 (s, 3H), 1.53 (s, 3H). | 413 |

Example 26

(R)-5-Difluoromethyl-5-[2-fluoro-5-(3-methoxy-5-nitro-pyridin-2-ylamino)-phenyl]-5,6-dihydro-2H-[1,4]oxazin-3-ylamine

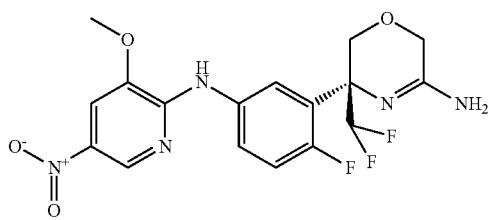 [SMILES: COc1cc([N+](=O)[O-])cnc1Nc1ccc(F)c([C@]2(C(F)F)COCC(N)=N2)c1]

The compound was prepared by a procedure analogous to those used for Examples 7 and 8, using 2-chloro-3-methoxy-5-nitro-pyridine (CAS registry 75711-00-1) and applying a reaction time of 24 h. The title compound was precipitated by addition of TBME and after filtration and drying obtained as grey-yellow solid.

UPLC: Rt$_{H9}$=0.73 min; ESIMS: 412.2 [(M+H)⁺];

¹H-NMR (600 MHz, DMSO-d6): δ 11.02 (s, 1H), 9.72 (br. s, 1H), 9.55 (s, 1H), 8.79 (br. s, 1H), 8.75-8.69 (m, 1H), 8.11 (d, 1H), 7.94 (d, 1H), 7.84 (s, 1H), 7.40-7.28 (m, 1H), 6.77 (t, 1H), 4.71 (d, 1H), 4.63 (d, 1H), 4.33 (d, 1H), 4.18 (d, 1H), 4.04 (s, 3H).

Example 27

N*2*-[3-((R)-5-Amino-3-difluoromethyl-3,6-dihydro-2H-[1,4]oxazin-3-yl)-4-fluoro-phenyl]-3-methoxy-pyridine-2,5-diamine

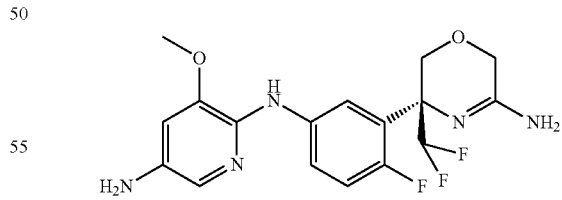

To a solution of (R)-5-difluoromethyl-5-[2-fluoro-5-(3-methoxy-5-nitro-pyridin-2-ylamino)-phenyl]-5,6-dihydro-2H-[1,4]oxazin-3-ylamine (80 mg, 0.179 mmol) in EtOH (10 ml) was added Pd—C (10%, 50 mg) the mixture was set under an atmosphere of hydrogen and stirred for 1 h. The catalyst was filtered off, the mixture diluted with DCM (20 ml) aq. sat. Na₂CO₃ (5 ml) was added and stirred for 5 min. The layers were separated, the aq. phase extracted with DCM (20 ml), the combined organic layers were washed with aq. sat.

Na$_2$CO$_3$ (5 ml), dried with MgSO$_4$ and the solvent removed under reduced pressure. The residue was purified by prep. TLC on silica gel (DCM/MeOH 9:1) to afford the title compound as purple semi-solid.

UPLC: Rt$_{H9}$=0.51 min; ESIMS: 382.2 [(M+H)$^+$];

$^1$H-NMR (400 MHz, CD3OD): δ7.59 (dd, 1H), 7.53 (dt, 1H), 7.27 (d, 1H), 6.99 (dd, 1H), 6.78 (d, 1H), 6.34 (t, 1H), 4.25 (d, 2H), 4.16 (d, 1H), 4.01 (d, 1H), 3.86 (s, 3H), 3.20 (s, 2H).

Example 28

[6-((3R,6R)-5-Amino-3,6-dimethyl-6-trifluoromethyl-3,6-dihydro-2H-[1,4]oxazin-3-yl)-5-fluoropyridin-2-yl]-(7-trifluoromethyl-pyrido[3,2-d]pyrimidin-4-yl)-amine

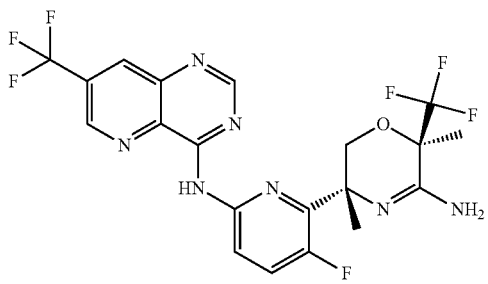 [SMILES: C[C@@]1(c2nc(Nc3ncnc4cc(C(F)(F)F)cnc34)ccc2F)CO[C@@](C)(C(F)(F)F)C(N)=N1]

The compound was prepared by a procedure analogous to those used for Example 23 using [(2R,5R)-5-(6-amino-3-fluoro-pyridin-2-yl)-2,5-dimethyl-2-trifluoromethyl-5,6-dihydro-2H-[1,4]oxazin-3-yl]-carbamic acid tert-butyl ester (CAS registry: 1337561-59-2, WO 2012/095469) and heteroaryl 3.

UPLC: Rt$_{H9}$=0.90 min; ESIMS: 504.3 [(M+H)$^+$];

$^1$H-NMR (400 MHz, DMSO-d6): δ 9.82 (br. s, 1H, NH), 9.35 (d, 1H), 8.94 (s, 1H), 8.79 (d, 1H), 8.55 (dd, 1H), 7.85 (dd, 1H), 5.94 (br. s, 2H, NH$_2$), 4.19 (d, 1H), 3.79 (d, 1H), 1.53 (s, 6H).

Example 29

(2R,5R)-5-[3-Fluoro-6-(2-methoxy-phenylamino)-pyridin-2-yl]-2,5-dimethyl-2-trifluoromethyl-5,6-dihydro-2H-[1,4]oxazin-3-ylamine

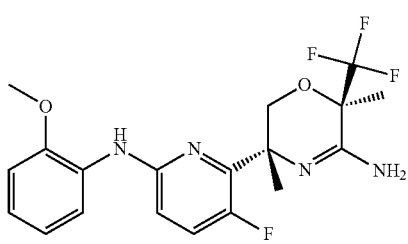 [SMILES: COc1ccccc1Nc1ccc(F)c([C@]2(C)CO[C@@](C)(C(F)(F)F)C(N)=N2)n1]

a) [(2R,5R)-5-(6-Bromo-3-fluoro-pyridin-2-yl)-2,5-dimethyl-2-trifluoromethyl-5,6-dihydro-2H-[1,4]oxazin-3-yl]-carbamic acid tert-butyl ester To a solution of (2R,5R)-5-(6-Bromo-3-fluoro-pyridin-2-yl)-2,5-dimethyl-2-trifluoromethyl-5,6-dihydro-2H-[1,4]oxazin-3-ylamine (100 mg, 0.27 mmol; CAS registry 1387561-18-3, WO 2012/095469) in DCM (2.7 ml) was added di-tert-butyl dicarbonate (62.7 μL, 0.270 mmol) followed by DIPEA (70.8 μL, 0.405 mmol). The reaction was stirred at rt for 18 h. The reaction mixture was diluted with DCM and washed with sat. aq. NaHCO$_3$ solution and brine and dried with Na$_2$SO$_4$. The residue was purified by chromatography (silica gel; eluent: CyHex/EtOAc gradient) to afford the title compound.

LCMS: Rt$_{H9}$=1.29 min; ESIMS: 470.4 [(M+H)$^+$];

$^1$H-NMR (400 MHz, CDCl$_3$): δ 11.24 (br. s, 1H, NH), 7.49 (dd, 1H), 7.36 (dd, 1H), 4.31 (d, 1H), 4.25 (d, 1H), 1.72 (s, 3H), 1.63 (s, 3H), 1.56 (s, 9H).

b) {(2R,5R)-5-[3-Fluoro-6-(2-methoxy-phenylamino)-pyridin-2-yl]-2,5-dimethyl-2-trifluoro-methyl-5,6-dihydro-2H-[1,4]oxazin-3-yl}-carbamic acid tert-butyl ester To a solution of [(2R,5R)-5-(6-bromo-3-fluoro-pyridin-2-yl)-2,5-dimethyl-2-trifluoromethyl-5,6-dihydro-2H-[1,4]oxazin-3-yl]-carbamic acid tert-butyl ester (130 mg, 0.276 mmol) in toluene (4 ml) in a microwave vial was added o-anisidine (0.037 ml, 0.332 mmol), Pd$_2$(dba)$_3$ (5.06 mg, 5.53 μmol), BINAP (6.89 mg, 0.011 mmol) and sodium tert-butoxide (37.2 mg, 0.387 mmol). The reaction mixture was degassed for 5 min, the microwave vial was sealed and stirred at 80° C. for 18 h. The reaction mixture was diluted with DCM and washed with water. The organic layer was dried with Na$_2$SO$_4$. The residue was purified by chromatography (silica gel; eluent: CyHex/EtOAc gradient) to afford the title compound.

LCMS: Rt$_{H9}$=1.38 min; ESIMS: 513.5 [(M+H)$^+$];

$^1$H-NMR (400 MHz, CDCl$_3$): δ 11.34 (br. s, 1H, NH), 8.04 (dd, 1H), 7.31 (dd, 1H), 7.07 (s, 1H, NH), 7.03-6.99 (m, 1H), 6.94-6.90 (m, 1H), 6.86-6.72 (m, 2H), 4.34 (d, 1H), 4.26 (d, 1H), 3.92 (s, 3H), 1.74 (s, 3H), 1.60 (s, 3H), 1.56 (s, 9H).

c) (2R,5R)-5-[3-Fluoro-6-(2-methoxy-phenylamino)-pyridin-2-yl]-2,5-dimethyl-2-trifluoromethyl-5,6-dihydro-2H-[1,4]oxazin-3-ylamine A mixture of {(2R,5R)-5-[3-fluoro-6-(2-methoxy-phenylamino)-pyridin-2-yl]-2,5-dimethyl-2-trifluoro-methyl-5,6-dihydro-2H-[1,4]oxazin-3-yl}-carbamic acid tert-butyl ester (95 mg, 0.148 mmol) and TFA (114 μl, 1.48 mmol) in DCM (1.48 ml) was stirred at rt for 18 h. The reaction mixture was poured onto a mixture of ice, NH$_4$OH and EtOAc. The organic layer was washed with water and brine and dried with Na$_2$SO$_4$. The crude product was purified by chromatography (silica gel; eluent:DCM/MeOH+NH$_4$OH) to afford the title compound.

LCMS: Rt$_{H9}$=0.81 min; ESIMS: 413.5 [(M+H)$^+$];

¹H-NMR (400 MHz, CDCl₃): δ 8.29 (dd, 1H), 7.29-7.22 (m, 1H), 7.04 (s, 1H, NH), 7.01-6.87 (m, 3H), 6.70 (dd, 1H), 4.31 (d, 2H), 3.92 (s, 3H), 3.89 (d, 1H), 1.66 (s, 3H), 1.51 (s, 3H).

Example 30

2-[6-((3R,6R)-5-Amino-3,6-dimethyl-6-trifluoromethyl-3,6-dihydro-2H-[1,4]oxazin-3-yl)-5-fluoro-pyridin-2-ylamino]-nicotinonitrile

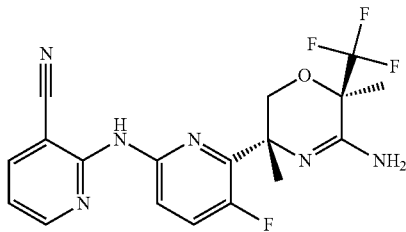 [SMILES: C[C@@]1(c2nc(Nc3ncccc3C#N)ccc2F)CO[C@@](C)(C(F)(F)F)C(N)=N1]

a) [Bis-(4-methoxy-phenyl)-phenyl-methyl]-[(2R, 5R)-5-(6-bromo-3-fluoro-pyridin-2-yl)-2,5-dimethyl-2-trifluoromethyl-5,6-dihydro-2H-[1,4]oxazin-3-yl]-amine To a solution of (2R,5R)-5-(6-bromo-3-fluoro-pyridin-2-yl)-2,5-dimethyl-2-trifluoromethyl-5,6-dihydro-2H-[1,4]oxazin-3-ylamine (500 mg, 1.35 mmol, CAS registry 1387561-18-3, WO 2012/095469) in DCM (13.5 ml) was added DMTr-Cl (0.481 g, 1.418 mmol) and triethylamine (0.374 ml, 2.70 mmol), the reaction mixture was stirred under argon at rt for 18 h. The reaction mixture was washed with NaHCO₃ saturated aqueous solution and brine. The organic layers were backextracted with DCM. The combined organic layer were dried with Na₂SO₄. The residue was purified by chromatography (eluent: CyHex/EtOAc gradient) to afford the title compound.

LCMS: Rt$_{H9}$=1.52 min; ESIMS: 674.0 [(M+H)⁺];
¹H NMR (400 MHz, CDCl₃): δ 7.44-7.37 (m, 2H), 7.35-7.30 (m, 4H), 7.26-7.16 (m, 5H), 6.87-6.76 (m, 4H), 5.44 (s, 1H, NH), 4.07 (d, 1H), 3.97 (d, 1H), 3.79 (s, 6H), 1.79 (s, 3H), 1.67 (s, 3H).

b) 2-[6-((3R,6R)-5-{[Bis-(4-methoxy-phenyl)-phenyl-methyl]-amino}-3,6-dimethyl-6-trifluoromethyl-3,6-dihydro-2H-[1,4]oxazin-3-yl)-5-fluoro-pyridin-2-ylamino]-nicotinonitrile To a solution of [bis-(4-methoxy-phenyl)-phenyl-methyl]-[(2R,5R)-5-(6-bromo-3-fluoro-pyridin-2-yl)-2,5-dimethyl-2-trifluoromethyl-5,6-dihydro-2H-[1,4]oxazin-3-yl]-amine (250 mg, 0.372 mmol) in toluene (3.72 ml) was added 2-amino-3-pyridinecarbonitrile (221 mg, 1.859 mmol), Pd₂(dba)₃ (6.81 mg, 7.43 μmol), BINAP (9.26 mg, 0.015 mmol) and sodium tert-butoxide (50 mg, 0.520 mmol). The reaction mixture was degassed for 5 min and the microwave vial was sealed and stirred at 100° C. for 9 h. The reaction mixture was diluted with DCM and washed with water. The organic layer was dried with Na₂SO₄. The residue was purified by chromatography (silica gel; eluent DCM/MeOH+NH₄OH) to afford the title compound.

LCMS: Rt$_{H10}$=1.54 min; ESIMS: 711.2 [(M+H)⁺].

c) 2-[6-((3R,6R)-5-Amino-3,6-dimethyl-6-trifluoromethyl-3,6-dihydro-2H-[1,4]oxazin-3-yl)-5-fluoro-pyridin-2-ylamino]-nicotinonitrile A mixture of [bis-(4-methoxy-phenyl)-phenyl-methyl]-{(2R,5R)-5-[3-fluoro-6-(3-methoxy-pyridin-2-ylamino)-pyridin-2-yl]-2,5-dimethyl-2-trifluoromethyl-5,6-dihydro-2H-[1,4]oxazin-3-yl}-amine (198 mg, 0.137 mmol) and TFA (105 μl, 1.36 mmol) in DCM (1.36 ml) was stirred at rt for 2.5 days. The reaction mixture was poured onto a mixture of ice, NH₄OH and EtOAc. The organic layer was washed with water and brine and dried with Na₂SO₄. The crude product was purified by chromatography (silica gel; eluent: DCM/MeOH+NH₄OH). The material was loaded on a 2.0 mm silica gel plate (20×20 cm) developed using DCM/MeOH 95:5+0.5% NH₄OH to afford the title compound.

LCMS: Rt$_{H10}$=0.76 min; ESIMS: 410.1 [(M+H)⁺];
¹H-NMR (400 MHz, DMSO-d₆): δ 9.40 (br. s, 1H) 8.51 (dd, 1H) 8.20 (dd, 1H) 7.66 (dd, 1H) 7.49 (dd, 1H) 7.13 (dd, 1H) 4.11 (d, 1H) 3.79 (d, 1H) 1.54 (s, 3H) 1.50 (s, 3H).

Example 31

The compound in Table 7 was prepared by a procedure analogous to that used to prepare Example 30.

TABLE 7

| Example | Compound | ¹H-NMR (δ; CDCl₃ or DMSO-d6) | MS [m/z; (M + H)⁺] |
|---|---|---|---|
| 31 | (2R,5R)-5-[3-Fluoro-6-(3-methoxy-pyridin-2-ylamino)-pyridin-2-yl]-2,5-dimethyl-2-trifluoromethyl-5,6-dihydro-2H-[1,4]oxazin-3-ylamine | 8.35 (dd, 1H), 7.87, (s, 1H, NH), 7.82 (dd, 1H), 7.65 (dd, 1H), 7.34 (d, 1H), 6.92 (dd, 1H), 4.17 (d, 1H), 3.93 (s, 3H), 3.86-3.71 (m, 1H), 1.55 (s, 3H), 1.51 (s, 3H). | LCMS: Rt$_{H9}$ = 0.71 min; [(M + H)⁺] = 414.2 |

Example 32

The compound listed in Table 8 was prepared by procedures analogous to those used for Example 2, using in the first step dioxane/water (1:1) instead of toluene/water, applying a reaction time of 10 min at 120° C. in a microwave and purifying by column chromatography with cyclohexane to cyclohexane/EtOAc 3:2.

TABLE 8

| Example | Compound | $^1$H-NMR (δ; DMSO-d6) | MS [m/z; (M + H)$^+$] |
|---|---|---|---|
| 32 | 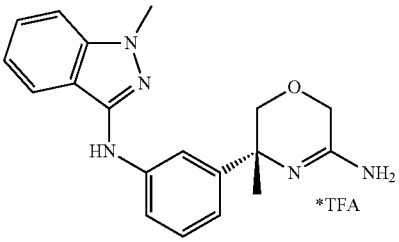 [3-((R)-5-Amino-3-methyl-3,6-dihydro-2H-[1,4]oxazin-3-yl)-phenyl]-(1-methyl-1H-indazol-3-yl)-amine trifluoroacetate | 10.54 (m, 1H), 9.11-8.99, (d, 2H), 8.57-8.42 (m, 1H), 7.96 (d, 1H), 7.81 (s, 1H), 7.67 (d, 1H), 7.52-7.46 (m, 1H), 7.40 (dd, 1H), 7.33 (t, 1H), 7.06 (t, 1H), 6.88 (d, 1H), 4.61 (s, 2H), 3.94-3.85 (m, 5H), 1.67 (s, 3H). | LCMS: Rt$_{H9}$ = 0.85 min; [(M + H)$^+$] = 336.3 |

Preparation of Heteroaryl Building Blocks

Heteroaryl 1: 3-Bromo-8-chloro-[1,7]naphthyridine a) 5-Bromo-3-methyl-pyridine-2-carboxylic acid amide

5-Bromo-3-methyl-pyridine-2-carboxylic acid ethyl ester (2.44 g, 10 mmol) was dissolved in NH$_3$/MeOH (50 ml) and heated to reflux for 3 days. The reaction mixture was concentrated to give the desired product as a pink solid (2.05 g, 9.6 mmol).

HPLC: Rt$_{H9}$=0.66 min; ESIMS [M+H]$^+$=215.1, 217.1 (1Br);

$^1$H-NMR (400 MHz, DMSO-d6): δ 8.59 (s, 1H), 8.05 (s, 1H), 7.80 (s, 1H), 7.50 (s, 1H), 2.50 (s, 3H).

b) 5-Bromo-3-methyl-pyridine-2-carboxylic acid 1-dimethylamino-meth-(E)-ylideneamine 5-Bromo-3-methyl-pyridine-2-carboxylic acid amide (2.00 g, 9.3 mmol) and dimethoxymethyl-dimethyl-amine (1.44 g, 12.09 mmol) were dissolved in toluene (50 ml) and heated to reflux overnight. The reaction mixture was concentrated to give the desired product (2.5 g, 9.25 mmol) as red/brown resin.

HPLC: Rt$_{H9}$=0.55 min; ESIMS [M+H]$^+$=270.1, 272.1 (1Br);

$^1$H-NMR (400 MHz, DMSO-d6): δ 8.58 (s, 1H), 8.49 (s, 1H), 7.97 (s, 1H), 3.19 (s, 3H), 3.03 (s, 3H), 2.38 (s, 3H).

c) 3-Bromo-7H[1,7]naphthyridin-8-one

5-Bromo-3-methyl-pyridine-2-carboxylic acid 1-dimethylamino-meth-(E)-ylideneamine (2.5 g, 9.25 mmol) was dissolved in THF (20 ml). KOtBu (1.565 g, 13.05 mmol) in THF (30 ml) was added dropwise and the reaction mixture was heated to reflux for 3 h and then cooled to rt. The pH was adjusted to 7 with concentrated HCl. The reaction mixture was concentrated. The brown solid obtained was triturated with water (10 ml). The solid thus obtained was collected by filtration (2 g, 8 mmol).

HPLC: Rt$_{H9}$=0.56 min; ESIMS [M+H]$^+$=224.8, 226.8 (1 Br);

$^1$H-NMR (400 MHz, DMSO-d6): δ 11.90 (s, 1H), 8.85 (s, 1H), 8.50 (s, 1H), 7.43 (d, 1H), 6.67 (d, 1H).

d) 3-Bromo-8-chloro-[1,7]naphthyridine

3-Bromo-7H-[1,7]naphthyridin-8-one (1.5 g, 6.67 mmol) was suspended in toluene (20 ml). DIPEA (3.5 ml, 20 mmol) and POCl$_3$ (1.8 ml, 20 mmol) were added and the reaction mixture was heated to 130° C. for 36 h. The reaction mixture was cooled to rt and partitioned between water (75 ml) and EtOAc (150 ml). The phases were separated and the aq phase was extracted twice with EtOAc (25 ml). The combined organic layer was washed with NaHCO$_3$ solution and brine, treated with MgSO$_4$ and filtered. The filtrated was concentrated to give the desired product as a beige solid (1.1 g, 4.52 mmol).

HPLC: Rt$_{H9}$=0.86 min; ESIMS [M+H]$^+$=242.8, 244.8, 246.8 (1Br, 1Cl);

$^1$H-NMR (400 MHz, DMSO-d6): δ 9.22 (d, 1H), 8.95 (2, 1H), 8.49 (d, 1H), 7.99 (d, 1H).

Heteroaryl 2: 3-(2-Methoxy-ethoxy)-7H-[1,7]naphthyridin-8-one a) 5-(2-Methoxy-ethoxy)-3-methyl-pyridine-2-carboxylic acid amide

5-Bromo-3-methyl-pyridine-2-carboxylic acid ethyl ester (3.3 g, 13.52 mmol) and CuI (0.515 g, 2.70 mmol) were dissolved in 2-methoxy-ethanol (10.29 g, 135 mmol) and DMF (2.5 ml). NaH (60%, 0.541 g, 13.52 mmol) was carefully added and the reaction mixture was warmed to 110° C. for 8 h. The reaction mixture was allowed to cool to rt and NH$_3$ in EtOH (10%, 30 ml) was added. The reaction mixture was placed in an autoclave and heated to 100° C. for 20 h. The reaction mixture was cooled to rt, concentrated and purified by column chromatography (silica gel; DCM/0-4% i-Propanol) to give the desired product (1 g, 4.52 mmol).

HPLC: Rt$_{H9}$=0.57 min; ESIMS [M+H]$^+$=211.2;

$^1$H-NMR (400 MHz, CDCl$_3$): δ 8.13 (s, 1H), 7.82 (s, 1H), 7.10 (s, 1H), 7.50 (s, 1H), 5.50 (s, 1H), 4.26 (t, 2H), 3.83 (t, 2H), 3.54 (s, 3H), 2.75 (s, 3H).

b) 5-(2-Methoxy-ethoxy)-3-methyl-pyridine-2-carboxylic acid 1-dimethylamino-meth-(E)-ylideneamine 5-(2-Methoxy-ethoxy)-3-methyl-pyridine-2-carboxylic acid amide (500 mg, 2.378 mmol) and dimethoxymethyl-dimethyl-amine (368 mg, 3.09 mmol) were dissolved in toluene (50 ml) and heated to reflux overnight. The reaction mixture was concentrated to give the desired product as a red/brown resin (600 mg, 2.26 mmol).
HPLC: $Rt_{H9}$=0.52 min; ESIMS [M+H]$^+$=266.2;
$^1$H-NMR (400 MHz, CDCl$_3$): δ 8.66 (s, 1H), 8.30 (s, 1H), 7.09 (s, 1H), 4.24 (m, 2H), 3.81 (m, 2H), 3.48 (s, 3H), 3.25 (m, 6H), 3.09 (s, 3H).

c) 3-(2-Methoxy-ethoxy)-7H-[1,7]naphthyridin-8-one 5-(2-Methoxy-ethoxy)-3-methyl-pyridine-2-carboxylic acid 1-dimethylamino-meth-(E)-ylideneamine (500 mg, 1.885 mmol) was dissolved in THF (15 ml) and heated to gentle reflux. KOtBu (317 mg, 2.83 mmol) in THF (30 ml) was added dropwise and the reaction mixture was heated to reflux for 2.5 h and then cooled to rt. The pH was adjusted to 7 with concentrated HCl. The reaction mixture was concentrated.
HPLC: $Rt_{H9}$=0.50 min; ESIMS [M+H]$^+$=221.2;

Heteroaryl 3: 4-Chloro-7-trifluoromethyl-pyrido[3,2-d]pyrimidine a) 3-Amino-5-trifluoromethyl-pyridine-2-carboxylic acid amide

To a solution of 3-nitro-5-trifluoromethyl-pyridine-2-carbonitrile (1194 g, 5500 mmol) in EtOAc (12 l) was added 450 g Pd/C (10%) and hydrogenated (1.1 bar) at ambient temperature for 7 days. The reaction mixture was filtered and concentrated. The crude product was recrystallized from heptane/DCM to give 880 g of the desired product as a yellowish solid.
HPLC: $Rt_{H9}$=0.77 min; ESIMS [M+H]$^+$=206.

b) 7-Trifluoromethyl-pyrido[3,2-d]pyrimidin-4-ol

A mixture of 3-amino-5-trifluoromethyl-pyridine-2-carboxylic acid amide (500 mg, 2.44 mmol) and tri-ethoxymethane (1.8 g, 12.2 mmol) were heated to 120° C. for 16 h. The mixture was cooled to ambient temperature and treated with low boiling PE. The reaction mixture was stirred for 10 minutes, cooled to 0° C. and the beige solid was collected by filtration (350 mg).
HPLC: $Rt_{H9}$=0.56 min; ESIMS [M+H]$^+$=215.9;
$^1$H-NMR (400 MHz, DMSO-d6): δ 12.81 (s, 1H), 9.10 (s, 1H), 8.49 (s, 1H), 8.26 (s, 1H). $^{19}$F-NMR (376 MHz, DMSO-d6): δ −61.44 (s).

c) 4-Chloro-7-trifluoromethyl-pyrido[3,2-d]pyrimidine

7-Trifluoromethyl-pyrido[3,2-d]pyrimidin-4-ol (300 mg, 1.39 mmol) was dissolved in toluene (5 ml). DIPEA (541 mg, 4.18 mmol) and POCl$_3$ (641 mg, 4.18 mmol) were added and the reaction mixture was heated to 115° C. (external temperature). The reaction was cooled to rt and partioned between water (50 ml) and EtOAc (50 ml). The phases were separated and the aq phase was extracted twice with EtOAc (25 ml). The combined organic layer was washed with NaHCO$_3$ solution and brine, treated with MgSO$_4$ and filtered. The filtrate was concentrated, redissolved in DCM and filtered over silica and again concentrated to give the desired product as a colorless solid.
HPLC: $Rt_{H9}$=0.89 min;
$^1$H-NMR (400 MHz, DMSO-d6): δ 9.10 (s, 1H), 8.49 (s, 1H), 8.27 (s, 1H).
$^{19}$F-NMR (376 MHz, DMSO-d6): δ −61.45 (s).

Heteroaryl 4: 2-Chloro-3-(2,2-difluoro-ethoxy)-pyridine

2-Chloro-pyridin-3-ol (1 g, 7.72 mmol) was dissolved in DMF, K$_2$CO$_3$ (1.387 g, 10.04 mmol) was added and the mixture was stirred at 65° C., then 1,1-difluoro-2-iodo-ethane (1.630 g, 8.49 mmol) was added and the reaction mixture was stirred at 65° C. for 16 h.

The reaction mixture was cooled to rt and partitioned between water (50 ml) and EtOAc (50 ml). The phases were separated and the aq phase was extracted twice with EtOAc (25 ml). The combined organic layer was washed with NaHCO$_3$ solution and brine, treated with MgSO$_4$, filtered and concentrated to obtain the desired product as a white solid (1.32 g, 6.48 mmol).
HPLC: $Rt_{H9}$=0.79 min; ESIMS [M+H]$^+$=194.0, 196.1 (1Cl);
$^1$H-NMR (400 MHz, CDCl$_3$): δ 8.09 (m, 1H), 7.24 (m, 2H), 6.16 (tt, 1H), 4.25 (dt, 2H).

The invention claimed is:
1. A compound of the formula (I), or a pharmaceutically acceptable salt thereof:

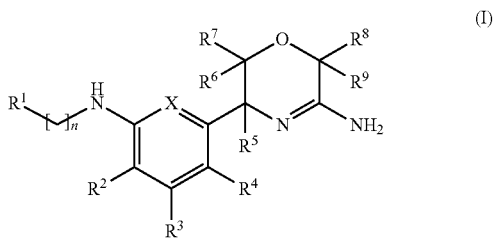

wherein
n represents 0 or 1;
X represents CH or N;
R$^1$ represents:
  phenyl, optionally substituted by 1, 2 or 3 substituents independently selected from R$^{10}$;
  a group G$_1$ selected from furan-2-yl, pyridin-2-yl, pyrimidin-2-yl, pyrimidin-4-yl and pyrazin-2-yl, wherein G$_1$ is optionally substituted by 1, 2 or 3 substituents independently selected from R$^{10}$; or
  a group G$_2$ selected from isothiazolo[4,5-b]pyridin-3-yl, isothiazolo[4,5-b]pyrazin-3-yl, benzo[d]isothiazol-3-yl, indazol-3-yl, benzo[d]isoxazol-3-yl, pyrido[3,2-d]pyrimidin-4-yl, [1,7]naphthyridin-8-yl and imidazol[1,2-a]pyrazin-8-yl, wherein G$_2$ is optionally substituted by 1, 2 or 3 substituents independently selected from R$^{11}$;
R$^2$, R$^3$ and R$^4$ independently represent hydrogen, halogen or C$_{1-3}$alkyl;
R$^5$ represents C$_{1-3}$alkyl, halogen-C$_{1-3}$alkyl or C$_{1-3}$alkoxy-C$_{1-3}$alkyl;
R$^6$ and R$^7$ independently represent hydrogen or C$_{1-3}$alkyl;

R[8] and R[9] independently represent hydrogen, $C_{1-3}$alkyl, halogen-$C_{1-3}$alkyl or $C_{1-3}$alkoxy; or R[8] and R[9] taken together are cyclopropyl;

R[10] represents halogen, cyano, hydroxy, halogen-$C_{1-3}$ alkoxy, $C_{1-3}$alkoxy, $C_{1-3}$alkoxy-$C_{1-3}$alkoxy, nitro or amino; and R[11] represents halogen, cyano, hydroxy, halogen-$C_{1-3}$ alkyl, halogen-$C_{1-3}$alkoxy, $C_{1-3}$alkoxy, $C_{1-3}$alkoxy-$C_{1-3}$ alkyl or $C_{1-3}$alkoxy-$C_{1-3}$alkoxy.

2. A compound according to claim 1, or a pharmaceutically acceptable salt thereof, wherein R[10] represents halogen, cyano, hydroxy, halogen-$C_{1-3}$alkoxy, $C_{1-3}$alkoxy or $C_{1-3}$alkoxy-$C_{1-3}$alkoxy.

3. A compound according to claim 1 of formula (Ia), or a pharmaceutically acceptable salt thereof:

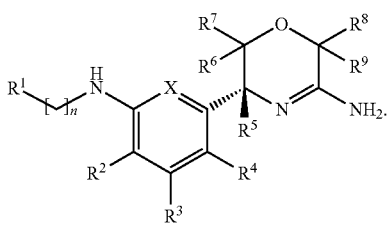

4. A compound according to claim 1, or a pharmaceutically acceptable salt thereof, wherein n represents 0.

5. A compound according to claim 1, or a pharmaceutically acceptable salt thereof, wherein X represents CH.

6. A compound according to claim 1, or a pharmaceutically acceptable salt thereof, wherein R[1] represents phenyl optionally substituted by 1 or 2 substituents independently selected from R[10].

7. A compound according to claim 1, or a pharmaceutically acceptable salt thereof, wherein R[1] represents a group $G_1$ selected from furan-2-yl, pyridin-2-yl, pyrimidin-2-yl, pyrimidin-4-yl and pyrazin-2-yl, wherein $G_1$ is optionally substituted by 1, 2 or 3 substituents independently selected from R[10].

8. A compound according to claim 1, or a pharmaceutically acceptable salt thereof, wherein R[1] represents a group $G_2$ selected from benzo[d]isothiazol-3-yl, indazol-3-yl, benzo [d]isoxazol-3-yl, pyrido[3,2-d]pyrimidin-4-yl, [1,7]naphthyridin-8-yl and imidazol[1,2-a]pyrazin-8-yl, wherein $G_2$ is optionally substituted by 1, 2 or 3 substituents independently selected from R[11].

9. A compound according to claim 1, or a pharmaceutically acceptable salt thereof, wherein R[2] represents hydrogen.

10. A compound according to claim 1, or a pharmaceutically acceptable salt thereof, wherein R[3] represents hydrogen or fluoro.

11. A compound according to claim 1, or a pharmaceutically acceptable salt thereof, wherein R[4] represents hydrogen or fluoro.

12. A compound according to claim 1, or a pharmaceutically acceptable salt thereof, wherein R[5] represents methyl, fluoromethyl or difluoromethyl.

13. A compound according to claim 1, or a pharmaceutically acceptable salt thereof, wherein R[6] and R[7] both represent hydrogen.

14. A compound according to claim 1, or a pharmaceutically acceptable salt thereof, wherein R[8] and R[9] independently represent hydrogen, methyl, fluoromethyl, difluoromethyl or trifluoromethyl.

15. A compound according to claim 1 which is selected from:

[3-(5-Amino-3-methyl-3,6-dihydro-2H-[1,4]oxazin-3-yl)-phenyl]-(6-bromo-benzo[d]isothiazol-3-yl)-amine;

[3-(5-Amino-3-methyl-3,6-dihydro-2H-[1,4]oxazin-3-yl)-phenyl]-(6-bromo-1-methyl-1H-indazol-3-yl)-amine;

[3-(5-Amino-3-methyl-3,6-dihydro-2H-[1,4]oxazin-3-yl)-phenyl]-benzo[d]isoxazol-3-yl-amine;

5-{2-Fluoro-5-[(furan-2-ylmethyl)-amino]-phenyl}-5-methyl-5,6-dihydro-2H-[1,4]oxazin-3-ylamine;

5-[5-(4-Bromo-2-chloro-benzylamino)-2-fluoro-phenyl]-5-fluoromethyl-5,6-dihydro-2H-[1,4]oxazin-3-ylamine;

5-{5-[(4-Bromo-furan-2-ylmethyl)-amino]-2-fluoro-phenyl}-5-difluoromethyl-5,6-dihydro-2H-[1,4]oxazin-3-ylamine;

3-((R)-5-Amino-3-difluoromethyl-3,6-dihydro-2H-[1,4] oxazin-3-yl)-4-fluoro-phenyl]-(7-chloropyrido[3,2-d] pyrimidin-4-yl)-amine;

[3-((R)-5-Amino-3-difluoromethyl-3,6-dihydro-2H-[1,4] oxazin-3-yl)-4-fluoro-phenyl]-(3-bromo-[1,7]naphthyridin-8-yl)-amine;

8-[3-((R)-5-Amino-3-difluoromethyl-3,6-dihydro-2H-[1,4]oxazin-3-yl)-4-fluoro-phenylamino]-[1,7]naphthyridine-3-carbonitrile;

[3-((R)-5-Amino-3-difluoromethyl-3,6-dihydro-2H-[1,4] oxazin-3-yl)-4-fluoro-phenyl]-[3-(2-methoxy-ethoxy)-[1,7]naphthyridin-8-yl]-amine;

[3-((R)-5-Amino-3-difluoromethyl-3,6-dihydro-2H-[1,4] oxazin-3-yl)-4-fluoro-phenyl]-[3-(2-chloro-ethoxy)-[1, 7]naphthyridin-8-yl]-amine;

[3-((R)-5-Amino-3-difluoromethyl-3,6-dihydro-2H-[1,4] oxazin-3-yl)-4-fluoro-phenyl]-(2-methyl-imidazo[1,2-a]pyrazin-8-yl)-amine;

[3-((R)-5-Amino-3-difluoromethyl-3,6-dihydro-2H-[1,4] oxazin-3-yl)-4-fluoro-phenyl]-imidazo[1,2-a]pyrazin-8-yl-amine;

[3-((R)-5-Amino-3-difluoromethyl-3,6-dihydro-2H-[1,4] oxazin-3-yl)-4-fluoro-phenyl]-(3-bromo-imidazo[1,2-a]pyrazin-8-yl)-amine;

(R)-5-Difluoromethyl-5-[2-fluoro-5-(3-methoxy-pyridin-2-ylamino)-phenyl]-5,6-dihydro-2H-[1,4]oxazin-3-ylamine;

(R)-5-Difluoromethyl-5-[2-fluoro-5-(pyrimidin-2-ylamino)-phenyl]-5,6-dihydro-2H-[1,4]oxazin-3-ylamine;

(R)-5-Difluoromethyl-5-[2-fluoro-5-(4-methoxy-pyrimidin-2-ylamino)-phenyl]-5,6-dihydro-2H-[1,4]oxazin-3-ylamine;

(R)-5-Difluoromethyl-5-[2-fluoro-5-(3-methoxy-pyrazin-2-ylamino)-phenyl]-5,6-dihydro-2H-[1,4]oxazin-3-ylamine;

(R)-5-Difluoromethyl-5-[5-(3-ethoxy-pyridin-2-ylamino)-2-fluoro-phenyl]-5,6-dihydro-2H-[1,4]oxazin-3-ylamine;

(R)-5-{5-[3-(2,2-Difluoro-ethoxy)-pyridin-2-ylamino]-2-fluoro-phenyl}-5-difluoromethyl-5,6-dihydro-2H-[1,4] oxazin-3-ylamine;

(R)-5-Difluoromethyl-5-[2-fluoro-5-(5-methoxy-pyrimidin-4-ylamino)-phenyl]-5,6-dihydro-2H-[1,4]oxazin-3-ylamine;

(R)-5-[5-(3-Difluoromethoxy-pyridin-2-ylamino)-2-fluoro-phenyl]-5-difluoromethyl-5,6-dihydro-2H-[1,4] oxazin-3-ylamine;

[3-((3R,6R)-5-Amino-3,6-dimethyl-6-trifluoromethyl-3,6-dihydro-2H-[1,4]oxazin-3-yl)-4-fluoro-phenyl]-(7-chloro-pyrido[3,2-d]pyrimidin-4-yl)-amine;

[3-((3R,6R)-5-Amino-3,6-dimethyl-6-trifluoromethyl-3,6-dihydro-2H-[1,4]oxazin-3-yl)-4-fluoro-phenyl]-(7-trifluoromethyl-pyrido[3,2-d]pyrimidin-4-yl)-amine;

(2R,5R)-5-[2-Fluoro-5-(3-methoxy-pyridin-2-ylamino)-phenyl]-2,5-dimethyl-2-trifluoromethyl-5,6-dihydro-2H-[1,4]oxazin-3-ylamine;

(R)-5-Difluoromethyl-5-[2-fluoro-5-(3-methoxy-5-nitro-pyridin-2-ylamino)-phenyl]-5,6-dihydro-2H-[1,4]oxazin-3-ylamine;

N*2*-[3-((R)-5-Amino-3-difluoromethyl-3,6-dihydro-2H-[1,4]oxazin-3-yl)-4-fluoro-phenyl]-3-methoxy-pyridine-2,5-diamine;

[6-((3R,6R)-5-Amino-3,6-dimethyl-6-trifluoromethyl-3,6-dihydro-2H-[1,4]oxazin-3-yl)-5-fluoro-pyridin-2-yl]-(7-trifluoromethyl-pyrido[3,2-d]pyrimidin-4-yl)-amine;

(2R,5R)-5-[3-Fluoro-6-(2-methoxy-phenylamino)-pyridin-2-yl]-2,5-dimethyl-2-trifluoromethyl-5,6-dihydro-2H-[1,4]oxazin-3-ylamine;

2-[6-((3R,6R)-5-Amino-3,6-dimethyl-6-trifluoromethyl-3,6-dihydro-2H-[1,4]oxazin-3-yl)-5-fluoro-pyridin-2-ylamino]-nicotinonitrile;

(2R,5R)-5-[3-Fluoro-6-(3-methoxy-pyridin-2-ylamino)-pyridin-2-yl]-2,5-dimethyl-2-trifluoromethyl-5,6-dihydro-2H-[1,4]oxazin-3-ylamine;

[3-((R)-5-Amino-3-methyl-3,6-dihydro-2H-[1,4]oxazin-3-yl)-phenyl]-(1-methyl-1H-indazol-3-yl)-amine; and pharmaceutically acceptable salts thereof.

16. A pharmaceutical composition comprising a compound according to claim 1, or a pharmaceutically acceptable salt thereof, as active pharmaceutical ingredient in association with at least one pharmaceutically acceptable carrier or diluent.

17. A method of treating Alzheimer's Disease or mild cognitive development, comprising administration of a compound according to claim 1, or a pharmaceutically acceptable salt thereof, to a patient in need thereof.

18. A method of treating insulin resistance, glucose intolerance, type 2 diabetes, obesity, or hypertension comprising administration of a compound according to claim 1, or a pharmaceutically acceptable salt thereof, to a patient in need thereof.

19. A combination comprising a therapeutically effective amount of a compound according to claim 1, or a pharmaceutically acceptable salt thereof, and a second drug substance, for simultaneous or sequential administration.

* * * * *